United States Patent [19]

Okita et al.

[11] Patent Number: 5,298,649

[45] Date of Patent: Mar. 29, 1994

[54] NAPHTHALENE DERIVATIVE

[75] Inventors: Makoto Okita, Tsuchiura; Hiroshi Shirota, Tsukuba; Masayuki Tanaka; Toshihiko Kaneko, both of Ushiku; Katsuya Tagami, Ibaraki; Shigeki Hibi; Yasushi Okamoto, both of Tsukuba; Seiichiro Nomoto; Takeshi Suzuki, both of Ushiku; Kenichi Chiba, Tsuchiura; Masaki Goto, Tsukuba; Ryoichi Hashida, Tsukuba; Hideki Ono, Tsukuba; Hideto Ohhara, Tsukuba; Hideki Sakurai, Tsukuba; Shigeru Souda, Ushiku; Yoshimasa Machida; Kouichi Katayama, both of Tsukuba; Isao Yamatsu, Ushiku, all of Japan

[73] Assignee: Eisai Co., Ltd., Tokyo, Japan

[21] Appl. No.: 774,237

[22] Filed: Oct. 10, 1991

Related U.S. Application Data

[62] Division of Ser. No. 451,468, Dec. 15, 1989, Pat. No. 5,134,111.

[30] Foreign Application Priority Data

Dec. 28, 1988 [JP] Japan .................. 63-331621

[51] Int. Cl.$^5$ ............................ C07C 69/76
[52] U.S. Cl. ..................... 560/56; 562/466; 564/174; 546/226; 544/389; 544/172
[58] Field of Search ............ 560/56; 562/466; 564/174; 514/532, 569, 622; 546/226; 544/389, 172

[56] References Cited

U.S. PATENT DOCUMENTS 5,134,111  7/1992  Okita .................. 562/466

OTHER PUBLICATIONS

CA74(11):53331t (1971).
CA105(25):226086f (1986).
CA88(5):37483c (1977).
CA68(13):59350w 1967.
CA93(25):239314n 1980.
CA93(25):239314n 1980 (different structures).
CA102(23):203862e 1985.
CA106(23):196242e 1986.

Primary Examiner—Paul J. Killos
Attorney, Agent, or Firm—Nixon & Vanderhye

[57] ABSTRACT

A naphthalene derivative having the formula is new and useful for medicine.

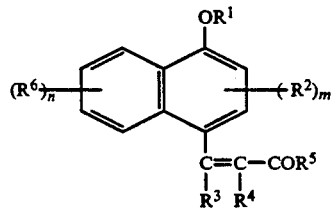

wherein $R^1$ represents a hydrogen atom, a lower alkyl group or an acyl group;

$R^2$ independently represents a hydrogen atom, a lower alkyl group, a lower alkoxy group, a halogen atom, a cycloalkyl group, a cycloalkylalkyl group, a hydroxyl group, an aryl group which may be substituted, an arylalkyl group whose aryl group may be substituted, a heteroaryl group, or a heteroarylalkyl group;

$R^3$ and $R^4$ are the same or different and represent a hydrogen atom, a lower alkyl group, a lower alkenyl group, an aryl group which may have a substituent, an arylalkyl group whose aryl group may be substituted, an arylalkenyl group whose aryl group may be substituted, a cycloalkyl group, an alkoxyalkyl group, a heteroaryl group, a heteroarylalkyl group, a carboxyl group, a carboxyalkyl group, an aminoalkyl group, or a cyano group;

$R^5$ represents a group of the formula, $-OR^7$, (wherein $R^7$ represents a hydrogen atom or a lower alkyl group), or a group of the formula,

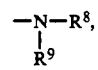

(wherein $R^8$ and $R^9$ are the same or different and represent a hydrogen atom or a lower alkyl group.

22 Claims, No Drawings

NAPHTHALENE DERIVATIVE

This is a division of application Ser. No. 07/451,468, filed Dec. 15, 1989 now U.S. Pat. No. 5,134,111.

INDUSTRIAL FIELD OF UTILIZATION

This invention relates to naphthalene derivatives. particularly, it relates to naphthalene derivatives whic a good efficacy as medicines.

BACKGROUND OF THE INVENTION AND PRIOR ART

Interleukin-1 (hereinafter referred to simply as IL a protein produced from macrophages, neutrocytes and the like and is a central factor of inflammation and immune systems. Its relation with autoimmune diseases and inflammatory diseases, typical of which is chronic articular rheumatism, is being clarified.

Especially, according to the recent report, it has been found that IL-1 is detected in rheumatoid chronica, particularly in the synovial fluid of chronic articular rhumatics, and the lymph cell emigration factor consists chiefly in IL-1 and that the peripheral hemomonocyte of rhumatics in activity is promoted in the IL-1 productivity.

We attempted to mainly suppress the production of IL-1 so that the automimmune diseases, such as chronic articular rheumatism, and diseases such as inflammatory diseases were cured and prevented.

The chronic articular rheumatism is a chronic inlflammatory disease whose cause is unknown. For medicinal therapy, non-steroid, antiphlogistic drugs have been used and their utility is not satisfactory in respect of the curing and side effects.

We have made extensive studies on compounds having the IL-1 production inhibiting action over a long period of time and found that naphthalene derivatives are excellent in the action.

Naphthalene derivatives are disclosed, for example, in Japanese Laid-open Patent Application No. 61-263943, as having the 5-lipoxigenase inhibiting action.

EMBODIMENTS AND FEATURES OF THE INVENTION

Under these circumstances in the art, studies and investigation have been made on compounds having good IL-1 production inhibiting action, with the result that it has been found that naphthalene derivatives of the following chemical structural formula can achieve this purpose.

The compounds of the invention are naphthalene derivatives of the following general formula (I), and pharmaceutically acceptable salts thereof,

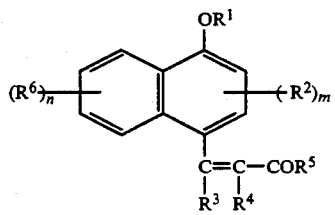

(I)

[wherein $R^1$ represents a hydrogen atom, a lower alky group or an acyl group;

$R^2$ independently represents a hydrogen atom, a lower alkyl group, a lower alkoxy group, a halogen atom, a cycloalkyl group, a cycloalkylalkyl group, a hydroxyl group, an aryl group which may be substituted, an arylalkyl group whose aryl group may be substituted, a heteroaryl group, or a heteroarylalkyl group:

$R^3$ and $R^4$ are the same or different and represent a hydrogen atom, a lower alkyl group, a lower alkenyl group, an aryl group which may have a substituent, an arylalkyl group whose aryl group may be substituted, an arylalkenyl group whose aryl group may be substituted, a cycloalkyl group, an alkoxyalkyl group, a heteroaryl group, a heteroarylalkyl group, a carboxyl group, a carboxyalkyl group, an aminoalkyl group, or a cyano group;

$R^5$ represents a group of the formula, $-OR^7$, (wherein $R^7$ represents a hydrogen atom or a lower alkyl group), or a group of the formula,

(wherein $R^8$ and $R^9$ are the same or different and represent a hydrogen atom or a lower alkyl group, or $R^8$ and $R^9$ can form, along with the nitrogen atom bonded with $R^8$ and $R^9$, a ring which may contain an oxygen atom);

$R^6$ independently represents a hydrogen atom, a halogen atom, a lower alkyl group, a lower alkoxy group, a hydroxyl group, an amino group, an arylalkyl group, or an aryl group; and m is 0 or an integer of from 1 to 2, and n is 0 or an integer of from 1 to 4.]

In the present specification, the position number of the respective carbon atoms in the naphthalene ring is determined in the following manner:

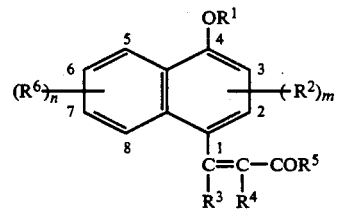

In the definitions of the compound (I) of the invention, the lower alkyl group represented by $R^1$, $R^2$, $R^3$, $R^4$, $R^6$, $R^7$, $R^8$ and $R^9$ is a linear or branched alkyl group having 1 to 6 carbon atoms and includes, for example, a methyl group, an ethyl group, a propyl group, an isopropyl group, a butyl group, an isobutyl group, a sec-butyl group, a tert-butyl group, a pentyl group (amyl group), an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,3-dimethylbutyl, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a, 1,2,2-trimethylpropyl group, a 1-ethyl-1-methylpropyl group, a 1-ethyl-2-methylpropyl group or the like. Of these, a methyl group, an ethyl group, a propyl group and an isopropyl group are preferred. Most preferably, a methyl group is used.

The lower alkenyl group defined by $R^3$ and $R^4$ is an alkenyl group derived from the above-defined lower alkyl group having from 1 to 6 carbon atoms.

The lower alkoxy group defined by $R^2$ is a lower alkoxy group derived from the above-defined lower alkyl group having from 1 to 6 carbon atoms. Preferable examples include a methoxy group, an ethoxy group, an n-propoxy group, an isopropoxy group, an n-butoxy group and the like.

The halogen atom defined by $R^2$ is chlorine, bromine, iodine or fluorine.

The cycloalkyl group defined by $R^2$ is a cycloalkyl group having from 3 to 7 carbon atoms and includes, for example, cyclopropyl, cyclobutyl, cyclopentyl, cyclohexyl, cycloheptyl or the like.

The cycloalkylalkyl group is a group derived from the above cycloalkyl group and typical examples include cyclopentylmethyl, cyclopropylmethyl, cyclohexylmethyl, cyclohexylethyl and the like groups.

The aryl group defined by $R^2$ and $R^5$ is, for example, a phenyl group, a naphthyl group or the like, which may be substituted with a lower alkyl group such as a methyl group, an ethyl group or the like, a halogen atom, a lower alkoxy group, or the like. The arylalkyl group whose aryl group may be substituted is an arylalkyl group derived from the above aryl group. Most preferably, a benzyl group, a phenetyl group or the like.

The heteroaryl group defined by $R^2$, $R^3$ and $R^4$ is a group derived from a heterocyclic ring such as a pyridyl group, a furyl group, a pyrimidyl group or the like. The heteroarylalkyl group is, for example, a pyridylmethyl group.

In the definition of the term "aryl group which may be substituted" used in $R^2$, $R^3$ and $R^4$, the substituent is, for example, a lower alkyl group such as a methyl group, an ethyl group, a propyl group or the like, a lower alkoxy group such as a methoxy group, an ethoxy group or the like, or a halogen atom. The term "an arylalkyl group whose aryl group may be substituted" is intended to mean a group derived from the aryl group which may be substituted.

The acyl group defined by $R^1$ represents residues of organic acids such as aliphatic saturated carboxylic acids, aliphatic unsaturated carboxylic acids, carbocyclic carboxylic acids or heterocyclic carboxylic acids. Specific examples include lower alkanoyl group such as formyl, acetyl, propionyl, butyryl, isobutyryl, valeryl, isovaleryl, pivaloyl and the like, aroyl groups such as benzoyl, toloyl, naphthoyl and the like, and heteroaroyl group such as furoyl, nicotinoyl, isonicotinoyl and the like.

The term "to form, along with the nitrogen atom bonded with $R^8$ and $R^9$, a ring which may contain an oxygen atom" used in the definition of $R^3$ and $R^4$ is intended to mean, for example, the following groups

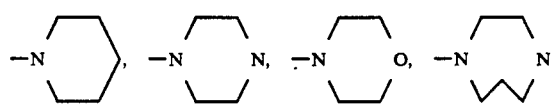

The compounds of the invention are characterized in that they have such a structure that the naphthalene ring is substituted with —$OR^1$ at the 4 position (wherein $R^1$ has the same meaning as defined before) and also with a group of the formula,

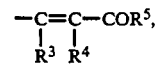

wherein $R^3$, $R^4$ and $R^5$ have, respectively, meanings as defined before).

In the above formula, $R^1$ is most preferably a hydrogen atom or an acyl group.

Most preferably, $R^3$ and $R^4$ are independently a hydrogen, atom, a lower alkyl group, an aryl group or an arylalkyl group.

In the general formula (I), the groups represented by the formula, —$(R^2)_m$, independently a hydrogen atom, a lower alkyl group, a lower alkoxy group, a halogen atom, a cycloalkyl group, a cycloalkylalkyl group, a hydroxyl group, an aryl group which may be substituted, an arylalkyl group whose aryl group may be substituted, a heteroaryl group or a heteroarylalkyl group. The term "independently" is intended to mean that when m is equal to 2, the substituents at the 2 and 3 positions of the naphthalene ring may be the same or different. More specifically, the formula (I) may be represented by the following formula (I')

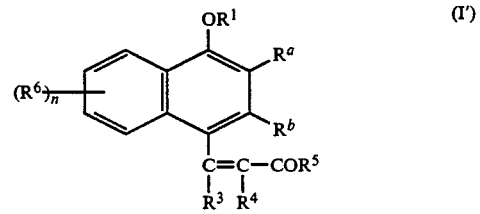

(wherein $R^1$, $R^2$, $R^3$, $R^4$, $R^5$, $R^6$ and n have, respectively, the same meanings as defined before, and $R^a$ and $R^b$ may be the same or different and represent a hydrogen atom, a lower alkyl group, a lower alkoxy group, a halogen atom, a cycloalkyl group, a cycloalkylalkyl group, a hydroxyl group, an aryl group which may be substituted, an arylalkyl group whose aryl group may be substituted, a heteroaryl group or a heteroarylalkyl group).

Preferably, m=1 and $R^2$ is at the 3 position of the naphthalene ring.

In the general formula (I), the groups represented by the formula, —$(R^6)_n$, independently a hydrogen atom, a halogen atom, a lower alkyl group, a lower alkoxy group, a hydroxyl group, an amino group, an aryl group or an arylalkyl group. The term "independently" means that when n is equal to 2, 3 or 4, the substituents at the 5 to 8 positions of the naphthalene group may be the same or different. More specifically, the general formula (I) may be represented by the following formula (I'')

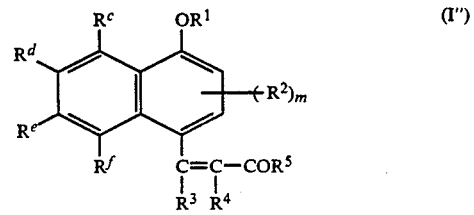

wherein $R^1$, $R^2$, $R^3$, $R^4$, $R^5$, and m have, respectively, the same meanings as defined before, and $R^o$, $R^d$, $R^e$ and $R^f$ may be the same or different and represent a hydrogen atom, a halogen atom, a lower alkyl group, a lower alkoxy group, a hydroxyl group, an amino group, an aryl group or an arylalkyl group).

In the practice of the invention, the most preferable compound group includes the naphthalene derivatives of the following general formula (A) or their pharmaceutically acceptable salts

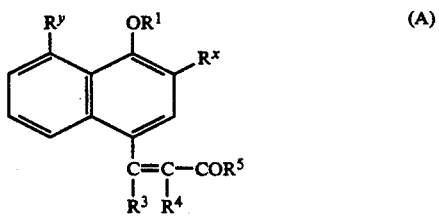

[wherein $R^1$ represents a hydrogen atom, a lower alkyl group or an acyl group;

$R^x$ represents a hydrogen atom, a lower alkyl group, a lower alkoxy group, a halogen atom, a cycloalkyl group, a cycloalkylalkyl group, a hydroxyl group, an aryl group which may be substituted, an arylalkyl group whose aryl group may be substituted, a heteroaryl group, or a heteroarylalkyl group;

$R^3$ and $R^4$ may be the same or different and represent a hydrogen atom, a lower alkyl group, a lower alkenyl group, an aryl group which may be substituted, an arylalkyl group whose aryl group may be substituted, an arylalkenyl group whose aryl group may be substituted, a cycloalkyl group, an alkoxyalkyl group, a heteroaryl group, a heteroarylalkyl group, a carboxyl group, a carboxyalkyl group, an aminoalkyl group or a cyano group;

$R^5$ represents a group of the formula, $-OR^7$, (wherein $R^7$ represents a hydrogen atom or a lower alkyl group), or a group of the formula,

(wherein $R^8$ and $R^9$ are the same or different and represent a hydrogen atom or a lower alkyl group, or $R^8$ and $R^9$ can form, along with the nitrogen atom bonded with $R^8$ and $R^9$, a ring which may contain an oxygen atom); and $R^y$ represents a hydrogen atom, a halogen atom, a lower alkyl group, a lower alkoxy group, a hydroxyl group, an amino group, an arylalkyl group or an aryl group.]

This is the case where, in the general formula (I) of the compounds of the invention, m and n are, respectively, equal to 1, $R^2$ is at the 3 position of the naphthalene ring [$R^x$ in the formula (A)], and $R^6$ is at the 5 position of the naphthalene ring [$R^y$ in the formula (A)].

In the formula (A), $R^1$ is most preferably a hydrogen atom and the second most preferably an acyl group.

$R^x$ is preferably a hydrogen atom, a lower alkyl group, a lower alkoxy group or a halogen atom, of which a lower alkoxy group is more preferred and a methoxy group is most preferred.

As preferred among the above-defined substituents, $R^3$ and $R^4$ are the same or different and represent a hydrogen atom or a lower alkyl group. Among lower alkyl groups, a methyl group and an ethyl group are most preferred.

$R^5$ is preferably a group of the formula, $-OR^7$, wherein $R^7$ is most preferably a hydrogen atom or a lower alkyl group.

$R^y$ is preferably a hydrogen atom, a lower alkyl group, a lower alkoxy group, a halogen atom, an aryl group or an arylalkyl group, of which the lower alkyl group such as a methyl group, an ethyl group or the like is most preferred.

The pharmaceutically acceptable salts used in the invention are ordinary innoxious salts such as, for example, inorganic acid salts such as hydrochlorides, hydrobromides, sulfates, phosphates and the like, organic acid salts such as acetates, maleates, tartrates, methanesulfonates, benzenesulfonates, toluenesulfonates and the like, and salts with amino acids such as alginine, aspartic acid, glutamic acid and the like.

The compounds of the invention have asymmetric carbon in the molecule and may include various steric isomers. In the practice of the invention, individual isomers and mixtures thereof are, of course, within the scope of the invention.

If hydrates are formed depending on the type of compound, such hydrates are also within the scope of the invention.

The compounds of the invention may be prepared by various processes, typical of which are the following processes.

PREPARATION PROCESSES

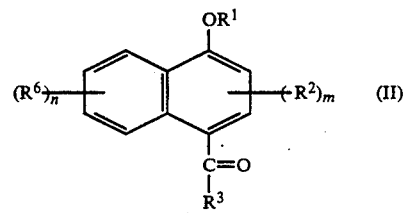

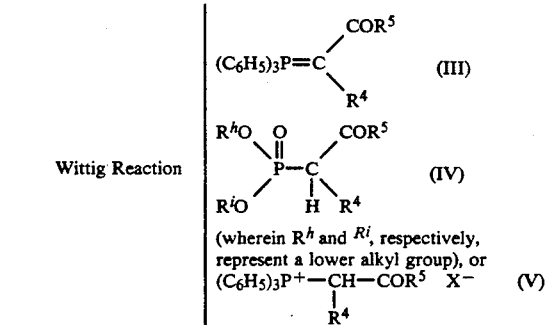

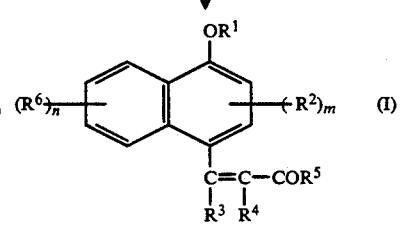

(in the above series of the formulae, $R^1$, $R^2$, $R^3$, $R^4$, $R^5$, $R^6$, m and n have, respectively, the same meanings as defined before).

More particularly, the phosphoric acid ester of the general formula (III), (IV) or (V) is caused to the Wittig reaction with the aldehyde or ketone compound of the general formula (II), thereby obtaining intended substance (I).

In the general formula (IV), $R^h$ and $R^i$, respectively, represent a lower alkyl group and most preferably an ethyl group.

Favorable results are obtained when these reactions are carried out in the presence of bases.

Examples of the base include sodium hydride, potassium hydride, sodium amide, sodium methoxide, sodium ethoxide, t-BuOK, MeLi, n-BuLi, and the like.

The reaction may be effected in solvent-free condition or in solvent. Examples of such a solvent include alcohols such as methanol, ethanol and the like, benzene, tetrahydrofuran, dimethoxyethane, dimethylformamide (DMF), dimethylsulfoxide and the like. The reaction temperature is from $-40°$ C. to the boiling point of solvent, preferably from about $0°$ to $70°$ C.

In the intended substances represented by the general formula (I), there exist trans-form products and cis-form products depending on the type of substituent. According to the above process, the product is made predominantly of the trans isomer. If it is desired to convert the trans-form product to the cis-form product, the conversion easily proceeds, for example, by subjecting the trans-form product to irradiation with light from a high pressure mercury lamp using a Pyrex filter.

As the sensitizers for the reaction, there can be mentioned acetone, propiophenone, acetophenone, benzophenone, triphenylene, 2-acetonaphthalene, 1-naphthyl phenyl ketone, 1-acetonaphthone and the like.

The solvents for the reaction include alcohols such as methanol, ethanol and the like, ketones such as acetone, methyl ethyl ketone, benzophenone and the like, benzene, acetonitrile, and the like.

The reaction temperature is from $-78°$ C. to $40°$ C., preferably from about $0°$ to $30°$ C.

The intended substances wherein $R^5$ is a hydroxyl group can be prepared according to the following procedure.

The substances of the general formula (I) are the case where $R^5$ is of the formula, $-OR^7$, (wherein $R^7$ has the same meaning as defined before), and when $R^7$ is a lower alkyl group, they are in the form of esters. The hydrolysis of the ester (VI) by a usual manner results in carboxylic acid (VII) which is one of the intended substances

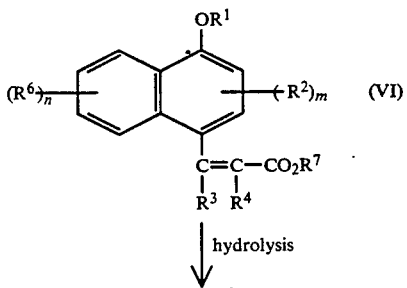
(VI)

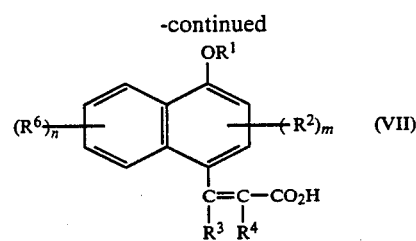
(VII)

(in the series of the formulae, $R^1$, $R^2$, $R^3$, $R^4$, $R^7$, m and n have, respectively, the same meanings as defined before).

If a trans or cis-form product is desired for the intended substance of the above formula (VII), such a product can easily be obtained by the use of a trans or cis-form compound as the starting compound (VI).

The hydrolysis reaction is carried out by a usual manner in a solvent such as water or a solvent miscible with water and selected, for example, from methanol, ethanol, tetrahydrofuran, acetonitrile, acetone and the like, in the presence of bases.

The bases include alkali metal carbonates such as sodium carbonate, potassium carbonate and the like, and alkali hydroxides such as sodium hydroxide, potassium hydroxide and the like.

The reaction temperature is about $0°$ C. or in the range of from room temperature to the boiling point of the solvent used.

The intended substance where $R^1$ is a hydrogen can be prepared according to the following procedure.

The substances of the formula (I) wherein $R^1$ is an acryl group are esters. When the ester (VIII) is hydrolyzed by a usual manner, a naphthol derivative (IX) which is one of the intended substances can be obtained.

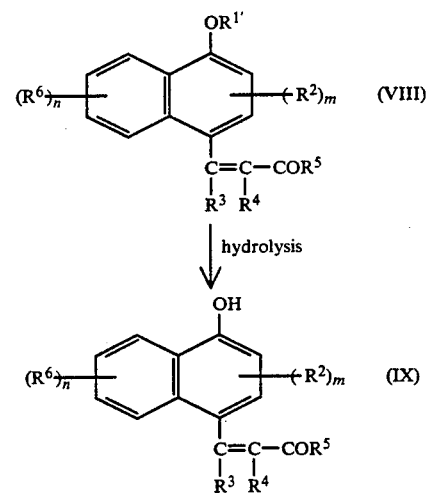

(wherein $R^2$, $R^3$, $R^4$, $R^5$, $R^6$, m and n have, respectively, the same meanings as defined before, and $R^1$ represents an acyl group).

In the substances represented by the above formula (IX), if a trans or cis-form product is desired, such a product can easily be obtained by the use of a trans or cis-form compound as the starting compound (VIII).

The reaction is carried out by a usual manner in a solvent such as water or a solvent miscible with water and selected, for example, from methanol, ethanol, tetrahydrofuran, acetonitrile, acetone and the like, in the presence of bases.

Examples of the base include alkali metal carbonates such as sodium carbonate, potassium carbonate and the like, and alkali hydroxides such as sodium hydroxide, potassium hydroxide and the like.

The reaction temperature is about 0° C. or in the range of from room temperature to the boiling point of the solvent used.

Naphthol derivatives of the general formula (I) wherein $R^5$ is a hydroxyl group and $R^1$ is a hydrogen atom may be obtained by hydrolyzing the starting substance (VI) wherein $R^1$ is a hydrogen atom, or by hydrolyzing the starting substance (VIII) wherein $R^5$ is a hydroxyl group.

The compound wherein $R^1$ is a hydrogen atom or which has a hydroxyl group at the 4 position of the naphthalene ring can be prepared according to the following procedure.

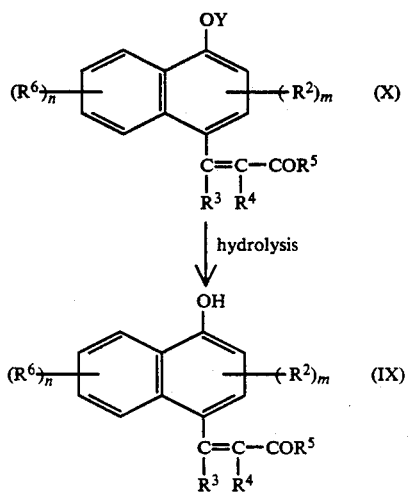

(wherein $R^2$, $R^3$, $R^4$, $R^5$, $R^6$, m and n have, respectively, the same meanings as defined before, and Y represents a protective group for the hydroxyl group).

More particularly, the compound of the general formula (X) wherein the hydroxyl group is appropriately protected with a protective group is used as a starting material and is hydrolyzed by a usual manner to obtain compound (IX) which is one of the intended substances.

The protective group includes, for example, not only a benzyl group, a p-methoxybenzyl group, a furan-2-yl group and a pyran-2-yl group, but also acetal protective groups such as a methoxymethyl group, an ethoxymethyl group, a methoxyethoxymethyl group and the like. Most preferably, a methoxymethyl group is used.

The solvents for the reaction include water, or solvents miscible with water and including, for example, ethers such as tetrahydrofuran, dioxane and the like, alcohols such as methanol, ethanol and the like, and acetone, acetonitrile and the like. In addition, esters such as ethyl acetate, and aromatic hydrocarbon groups such as benzene, toluene and the like are also usable.

The acids are, for example, hydrochloric acid, sulfuric acid, p-toluenesulfonic acid, D-10-camphorsulfonic acid, and the like.

The reaction temperature is from −40° C. to the boiling point of the solvent used, preferably from room temperature to the boiling point of the solvent.

The compound wherein $R^1$ is an acyl group or which has an acyloxy group at the 4-position of the naphthalene ring can be prepared, for example, according to the following procedure.

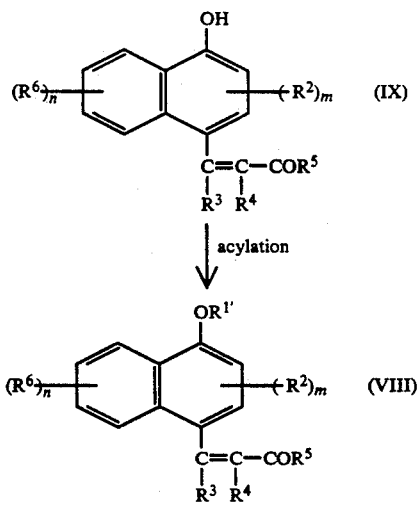

(wherein $R^2$, $R^3$, $R^4$, $R^5$, $R^6$, $R^{1'}$, m and n have, respectively, the same meanings as defined before).

More particularly, the naphthol derivatives (IX) are reacted by a usual manner with an acylating agent including, for example, a reactive acid derivative such as acetic anhydride, a desired carboxylic acid or an acid halide, or a carboxylic anhydride and a de-acidifying agent such as pyridine at a temperature of from about 0° C. to the boiling point of the solvent used, thereby readily obtaining trans-acyloxy derivatives of the general formula (VIII) which are one of the intended substances. A trans or cis-form product may be obtained depending on the type of substituent and, generally, trans-form products are obtained. For obtaining cis-form products, light from a high pressure mercury lamp using a Pyrex filter is irradiated on the trans-form products, thereby obtaining cis-acyloxy derivatives.

The sensitizers for the reaction include acetone, propiophenone, acetophenone, benzophenone, triphenylene, 2-acetonaphthone, 1-naphthyl phenyl ketone, 1-acetonaphthone and the like.

The solvents for the reaction include alcohols such as methanol, ethanol and the like, ketones such as acetone, methyl ethyl ketone, benzophenone and the like, benzene, acetonitrile, and the like.

The reaction temperature is from −78° C. to 40° C., preferably from about 0° C. to 30° C.

The compound of the general formula (II) which is the starting material for the preparation of the compounds of the invention is a novel compound and is useful as an important intermediate for the preparation of the naphthalene derivatives of the invention having good efficacy as medicines.

PREPARATION PROCESS A OF STARTING SUBSTANCES

The compound (XIV) of the general formula (II) or (X) used as the starting substance in the above preparation process can be prepared according to the following procedure

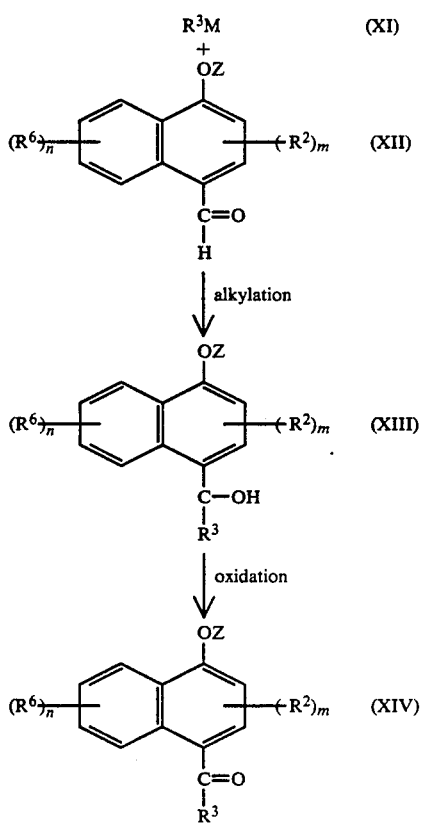

wherein the protective group for the hydroxyl group is a methoxymethyl group, m is equal to 1, and $R^2$ is a lower alkoxy group, they can be prepared according to the following procedure.

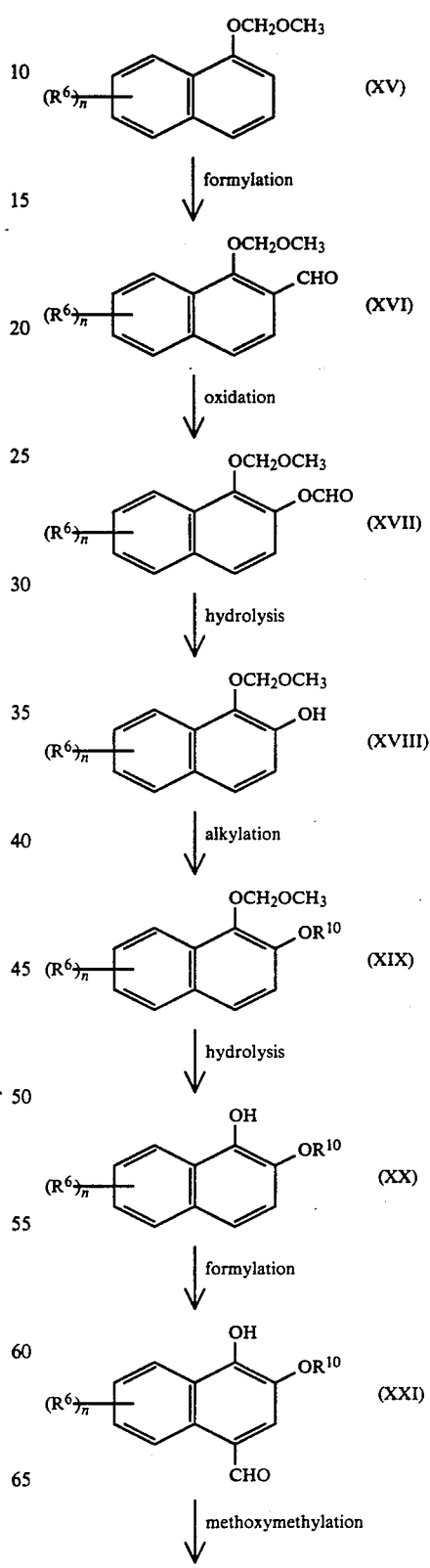

(wherein $R^2$, $R^3$, $R^6$, m and n have, respectively, the same meanings as defined before, Z represents a group represented by $R^1$, and Y represents a protective group for the hydroxyl group).

More particularly, the aldehyde derivative of the general formula (XII) and the organic metal compound of the general formula (XI) are reacted to obtain an alcohol derivative of the general formula (XIII).

The organic metal compounds are, for example, alkyl lithium, Grignard reagents, and the like.

The reaction is effected in a solvent selected, for example, from ether, tetrahydrofuran, dioxane, pentane, hexane and the like.

The reaction temperature is from −78° C. to 60° C., preferably from −78° C. to room temperature.

The alcohol derivative (XIII) thus obtained is oxidized by a usual manner to obtain a ketone derivative of the general formula (XIV).

The oxidizing agents include, for example, manganese dioxide, chromic acid, permanganates, lead tetraacetate, a halogen, N-halocarboxylic acid amides, dimethylsulfoxide and the like.

The solvents for the reaction include, for example, water and alcohols such as methanol, ethanol and the like, acetone, ether, acetonitrile, benzene, dichloromethane, chloroform, ethyl acetate, pyridine, and the like.

The reaction temperature is selected from the range of from ice-cooling conditions to the boiling point of the solvent used.

PREPARATION PROCESS B OF STARTING SUBSTANCES

For the preparation of the compounds of the general formula (XIV), in the above preparation process A,

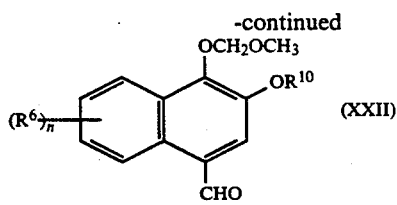

(XXII)

(wherein R⁶ and n have, respectively, the meanings as defined before, and R¹⁰ represents a lower alkyl group).

More particularly, the compound of the general formula (XV) and a strong base such as, for example, n-butyl lithium, are reacted, followed by further reaction with N,N-dimethylformamide to obtain aldehyde derivative (XVI). For the reaction, ethers such as ether, tetrahydrofuran and the like are used as the solvent and the reaction is carried out at a temperature of from −78° C. to 30° C., preferably from −30° C. to room temperature.

The aldehyde derivative (XVI) thus obtained is oxidized with an oxidizing agent such as, for example, hydrogen peroxide, peracetic acid, m-chloroperbenzoic acid or the like, thereby obtaining a formyl ester derivative (XVII). Water, dichloromethane, chloroform, acetic acid and the like are properly selected as the solvent.

The formyl ester derivative (XVII) thus obtained is subjected to alkali hydrolysis by a usual manner to obtain naphthol derivative (XVIII).

The naphthol derivative (XVIII) thus obtained is interacted with an alkyl halide by using a base including an alkali metal carbonate such as sodium carbonate, potassium carbonate or the like, or an alkali metal halide such as sodium hydride, to obtain alkoxynaphthalene (XIX). The halogen is chlorine, bromine or iodine. The solvent is, for example, a ketone such as acetone, methyl ethyl ketone or the like, N,N-dimethylformamide, dimethylsulfoxide or the like.

The alkoxynaphthalene derivative (XIX) thus obtained is subjected to acid hydrolysis by a usual manner using, for example, hydrochloric acid, sulfuric acid, p-toluenesulfonic acid or the like, thereby obtaining naphthol derivative (XX).

The naphthol derivative (XX) thus obtained is subsequently reacted, for example, with an ortho ether derivative such as ethyl orthoformate or methyl orthoformate, or dichloromethyl methyl ether to obtain the hydroxyformyl derivative of the general formula (XXI). The catalyst for the reaction includes, aluminum chloride, titanium tetrachloride or the like. Dichloromethane, chloroform and the like are used as the solvent.

The formyl derivative (XXI) thus obtained is reacted by a usual manner with chloromethyl methyl ether by the use of a base such as, for example, sodium hydride, diisopropylethylamine or the like, there by obtaining formyl derivative (XXII). The solvent is dichloromethane, chloroform, ether, tetrahydrofuran or the like compound which does not take part in the reaction. The reaction temperature if from −40° C. to 60° C., preferably from about 0° C. to room temperature.

PREPARATION PROCESS C OF STARTING SUBSTANCES

The compound (XXII) may be prepared according to the following procedure.

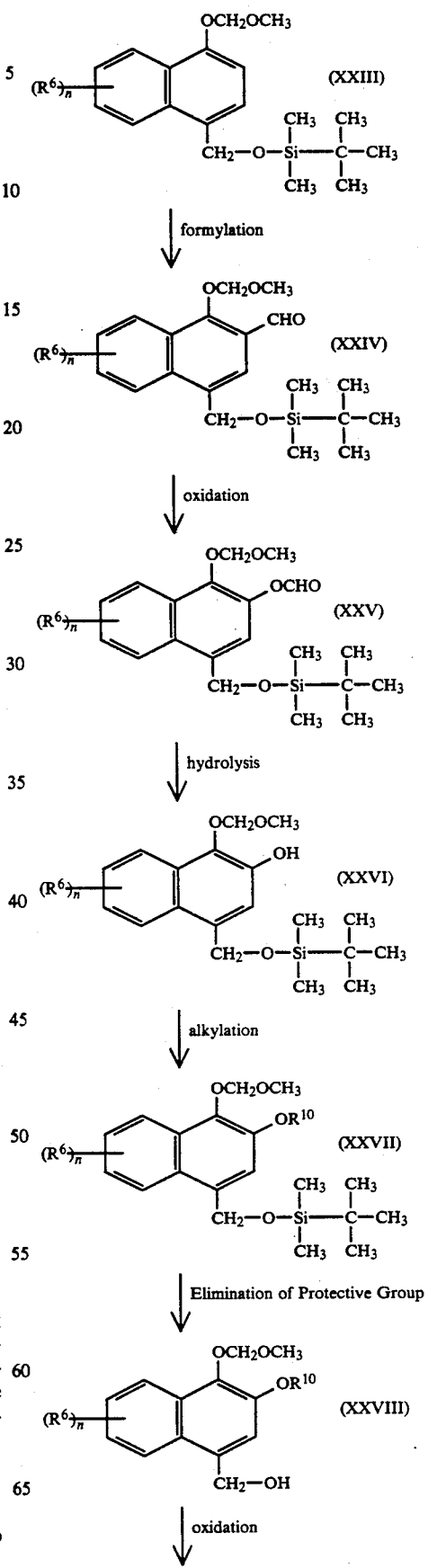

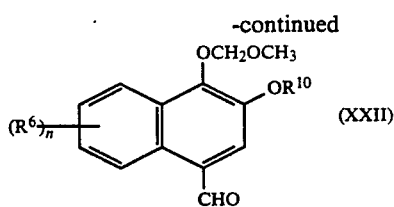

(wherein $R^6$, $R^{10}$ and n have, respectively, the same meanings as defined before).

More particularly, The naphthalene derivative of the general formula (XXIII) is subjected to formylation, oxidation, hydrolysis and alkylation according to a procedure similar to the preparation process B to obtain the naphthalene derivative of the general formula (XXVII).

The naphthalene derivative (XXVII) thus obtained is subjected to elimination of the protective group, for example, with tetra-n-butylammonium fluoride to obtain an alcohol product (XXVIII).

The alcohol product (XXVIII) thus obtained is oxidized to obtain the aldehyde derivative of the general formula (XXII).

As the oxidizing agent, there are mentioned manganese dioxide, chromic acid, permanganates, lead tetraacetate, halogens, N-halocarboxylic acid amides, dimethylsulfoxide and the like.

The solvent for the reaction includes, for example, water and alcohols such as methanol, ethanol and the like, acetone, ether, acetonitrile, benzene, dichloromethane, chloroform, ethyl acetate, pyridine, and the like.

The reaction temperature is appropriately selected from the range of from an ice-cooling condition to the boiling point of the solvent used.

PREPARATION PROCESS D OF STARTING SUBSTANCES

The compound (XXIII) used in the preparation process C can be prepared, for example, according to the following procedure.

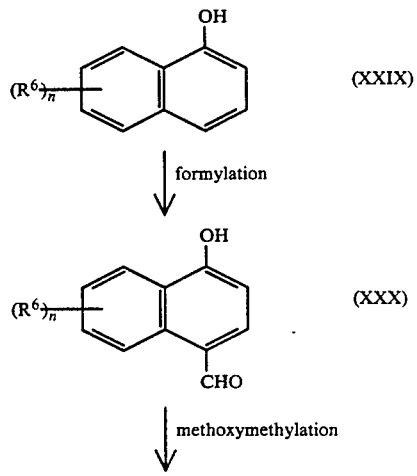

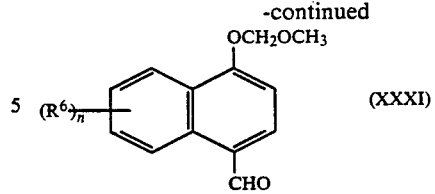

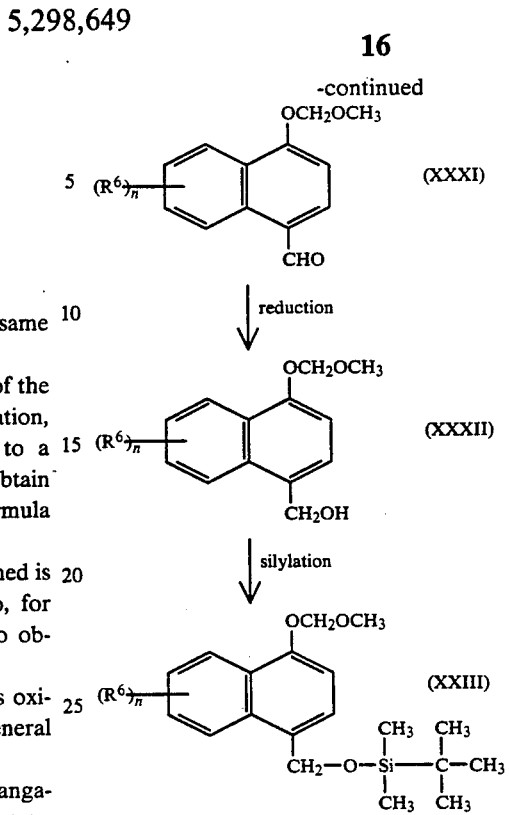

(wherein $R^6$ and n have, respectively, the same meanings as defined before).

In the above reaction sequence, the naphthol derivative of the general formula (XXIX) is reacted, for example, with an ortho-ester derivative such as methyl orthoformate or ethyl orthoformate, or dichloromethyl methyl ether, to obtain the hydroxyaldehyde derivative (XXX). Aluminum chloride, titanium tetrachloride or the like is used as the catalyst. The solvent for the reaction is, for example, dichloromethane, chloroform or the like.

The hydroxyaldehyde derivative (XXX) is reacted, by a usual manner, with chloromethyl methyl ether or the like by the use of a base such as, for example, sodium hydride, diisopropylethylamine or the like, thereby obtaining the aldehyde derivative (XXXI).

The aldehyde derivative (XXXI) thus obtained is reacted, by a usual manner, with a reducing agent such as, for example, sodium borohydride, lithium aluminium hydride or the like, thereby obtaining the alcohol derivative (XXXII).

The alcohol derivative derivative (XXXII) thus obtained is reacted, by a usual manner, with t-butyl-chlorodimethylsilane or the like by using a base such as, for example, imidazole, triethylamine or the like, to obtain the naphthalene derivative of the general formula (XXIII).

PREPARATION PROCESS E OF STARTING SUBSTANCES

As for the compound (XV) which has been used as the starting substance in the preparation process B and wherein n is equal to 1 and $R^6$ is a lower alkyl group joined at the 5 position, one of specific preparation procedures is illustrated below.

19

-continued

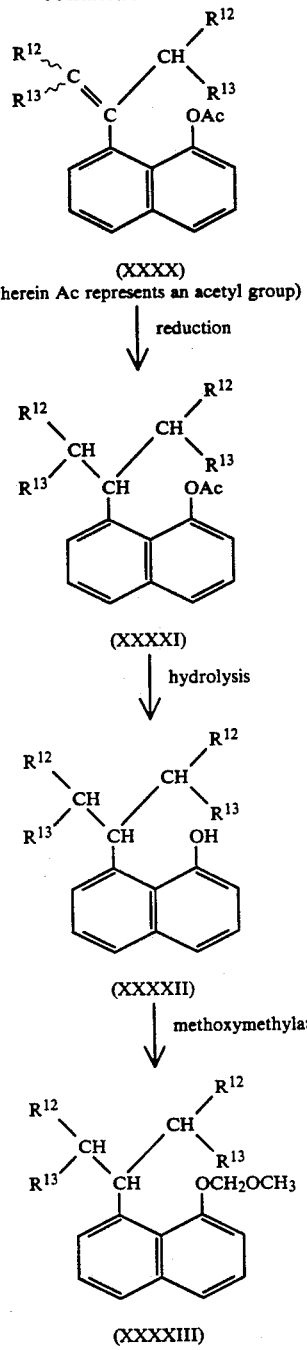

(XXXX)
(wherein Ac represents an acetyl group)

reduction (XXXXI)

hydrolysis (XXXXII)

methoxymethylation (XXXXIII)

More particularly, 1,8-naphthalenecarbolactone (XXXIII) is reaction with a Grignard reagent such as, for example, methyl magnesium bromide to obtain the diol derivative (XXXIX). The solvent for the reaction is, for example, ether, tetrahydrofuran or the like. The reaction temperature is from −70° C. to the boiling point of the solvent used, preferably from −60° C. to 0° C.

The thus obtained diol derivative (XXXIX) is heated by a usual manner along with acetic anhydride in pyridine used as a solvent at a temperature of from room temperature to 60° C. to obtain the acetate (XXXX).

The acetate (XXXX) thus obtained is catalytically hydrogenated by the use of a catalyst such as, for example, palladium-carbon to obtain reduced product

20

(XXXXI). The solvent for the reaction is, for example, alcohols such as methanol, ethanol and the like, ethyl acetate, tetrahydrofuran or the like. The reaction can proceed particularly at room temperature.

The reduced product (XXXXI) thus obtained is hydrolyzed as usual to obtain the naphthol derivative (XXXXII).

The naphthol derivative (XXXXII) thus obtained is reacted, by a usual manner, with chloromethyl methyl ether by the use of a de-acidifying agent such as, for example, sodium hydride, diisopropylethylamine or the like, thereby obtaining the naphthalene derivative (XXXXIII).

PREPARATION PROCESS G OF STARTING SUBSTANCES

The compound (XII) which has been used as the starting substance in the preparation process A and wherein n is equal to 1, $R^6$ is a lower alkyl group at the 5 position, Z is an acetyl group, m is equal to 1, and $R^2$ is a lower alkyl group at the 3 position can also be prepared by the following procedure.

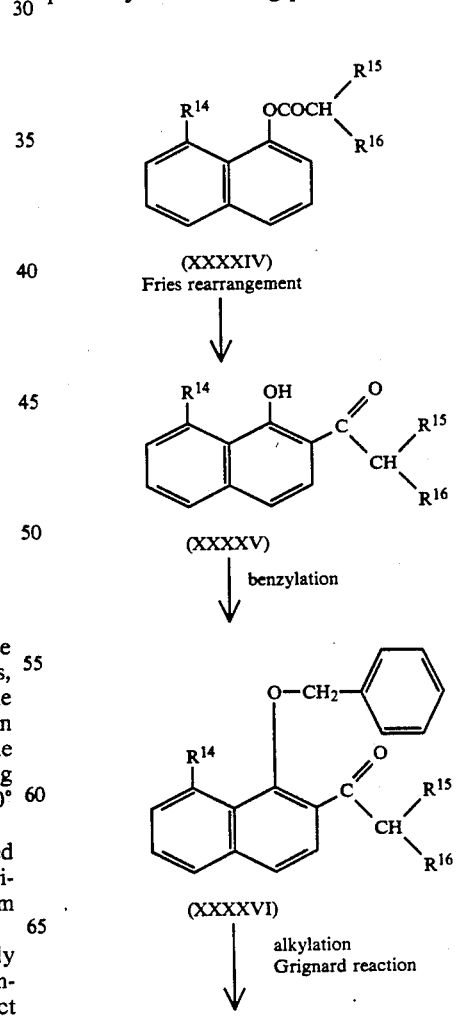

(XXXXIV)

Fries rearrangement (XXXXV)

benzylation (XXXXVI)

alkylation
Grignard reaction

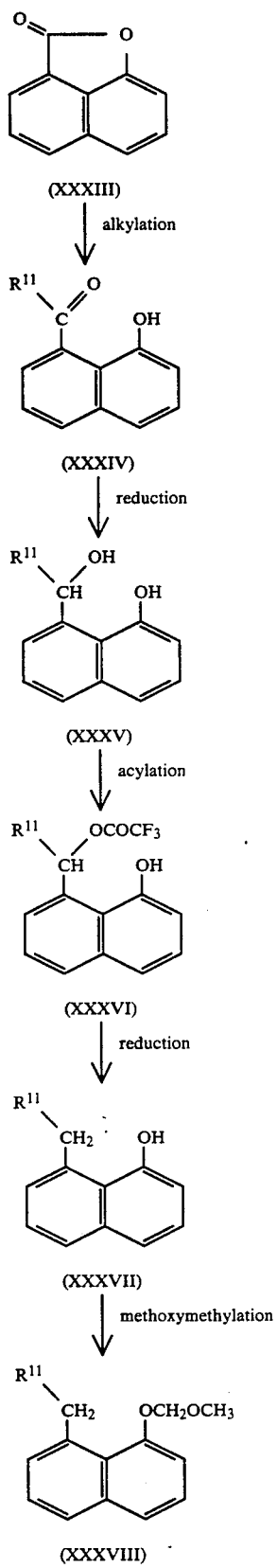

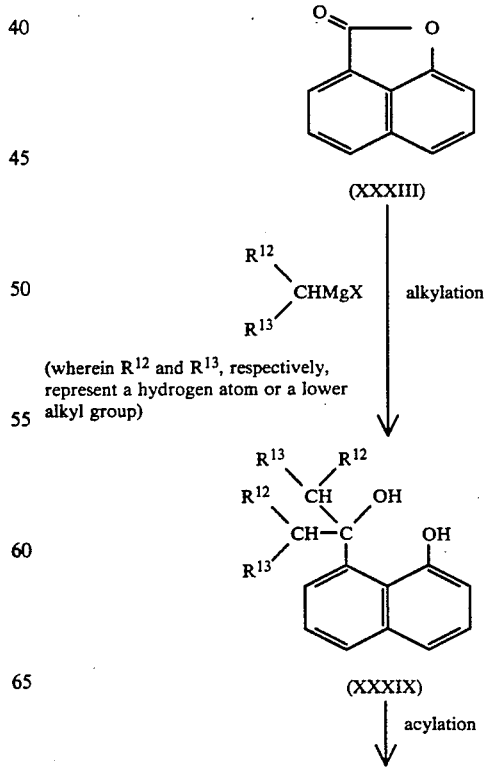

for example, an alkyl lithium, a Grignard reagent or the like to obtain the ketone derivative (XXXIV). The solvent for the reaction is, for example, ether, tetrahydrofuran, hexane or the like. The reaction temperature is from $-90°$ to $60°$ C., preferably from $-80°$ to $0°$ C.

The ketone derivative (XXXIV) thus obtained is reduced, by a usual manner, with a reducing agent such as, for example, sodium borohydride, aluminum hydride or the like to obtain the diol derivative (XXXV).

The thus obtained diol derivative (XXXV) is reacted, by a usual manner, with fluoroacetic acid by the use of a de-acidifying agent such as, for example, pyridine, at a temperature of an ice-cooling condition to room temperature, thereby obtaining the trifluoroacetate (XXXVI).

The trifluoroacetate (XXXVI) thus obtained is catalytically hydrogenated by the use of a catalyst such as, for example, palladium-carbon, thereby obtaining the naphthol derivative (XXXVII). The solvent for the reaction is, for example, alcohols such as methanol, ethanol and the like, ethyl acetate, tetrahydrofuran or the like. Room temperature may be used for the reaction.

The naphthol derivative (XXXVII) thus obtained is reacted, by a usual manner, with chloromethyl methyl ether by the use of a de-acidifying agent such as diisopropylethylamine, thereby obtaining the naphthol derivative (XXXVIII).

PREPARATION PROCESS F OF STARTING SUBSTANCES

One of preparation processes of the compound (XV), used as the starting substance in the above preparation process, wherein n is equal to 1 and $R^6$ is a lower alkyl group branched at the 5 position is described below.

(wherein $R^{12}$ and $R^{13}$, respectively, represent a hydrogen atom or a lower alkyl group)

(wherein $R^{11}$ represents a lower alkyl group).

More particularly, 1,8-naphthalenecarbolactone (XXXIII) is reacted with an alkylating agent such as, -continued

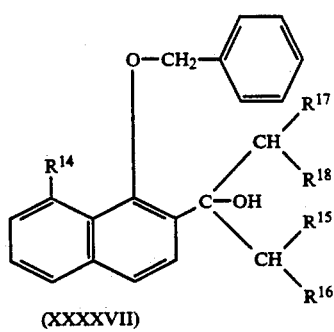

(XXXXVII)

↓ dehydration

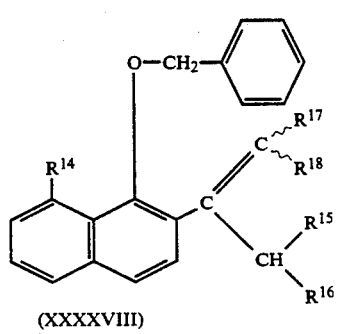

(XXXXVIII)

or

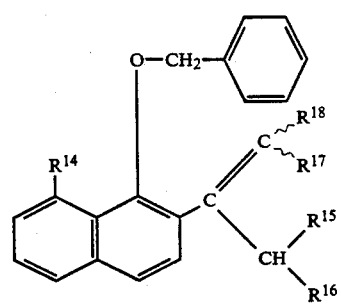

(XXXXIX)

↓ reduction

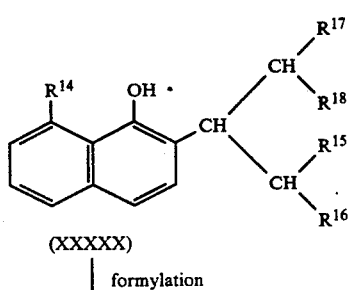

(XXXXX)

↓ formylation

-continued

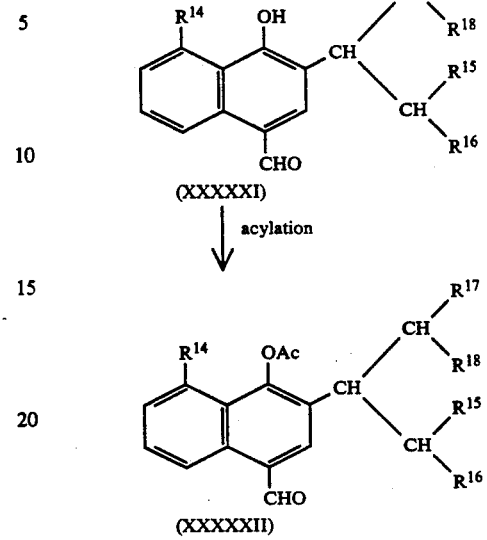

(wherein $R^{14}$ represents a lower alkyl group, $R^{15}$, $R^{16}$, $R^{17}$ and $R^{18}$ may be the same or different and represent a hydrogen atom or a lower alkyl group, and Ac has the same meaning as defined before).

More particularly, the ester derivative of the general formula (XXXXIV) is reacted as usual at 140° C. in the presence of an aluminum chloride catalyst to obtain the ketone product of the general formula (XXXXV).

Subsequently, the ketone product (XXXXV) is reacted with a benzyl halide such as benzyl chloride by the use of a de-acidifying agent such as, for example, sodium hydride, diisopropylethylamine or the like, thereby obtaining the benzyl ether derivative (XXXXVI). The solvent for the reaction is, for example, ethers such as ether, tetrahydrofuran and the like, halogenated hydrocarbons such as dichloromethane, chloroform and the like, benzene, N,N-dimethylformamide, dimethylsulfoxide, ethyl acetate or the like. The reaction temperature is appropriately selected depending on the type of reaction reagent.

The benzyl ether derivative (XXXXVI) thus obtained is reacted with an alkylating agent such as an alkyl lithium or a Grignard reagent to obtain the alcohol product (XXXXVII).

The alcohol product (XXXXVII) is heated as usual by the use of an acid catalyst such as, for example, a hydrochloric acid aqueous solution for dehydration reaction to obtain an olefin product (XXXXVIII) or (XXXXIX).

The olefin product (XXXXVIII) or (XXXXIX) thus obtained is subjected to catalytic hydrogenation using a catalyst such as, for example, palladium-carbon by a usual manner to obtain the naphthol derivative (XXXXX). The solvent for the reaction is alcohols such as methanol, ethanol and the like, ethyl acetate, tetrahydrofuran or the like. The reaction may be carried out particularly at room temperature.

The naphthol derivative (XXXX) thus obtained is reacted with an ortho ester such as methyl orthoformate or ethyl orthoformate, dichloromethyl methyl ether or the like to obtain the hydroxyaldehyde derivative (XXXXXI).

As the catalyst, there is mentioned aluminum chloride, titanium tetrachloride or the like. The solvent for the reaction is, for example, dichloromethane, chloroform or the like.

The hydroxyaldehyde derivative (XXXXXI) thus obtained is reacted, as usual, with an acylating agent such as acetic anhydride, acetyl chloride or the like by the use of a de-acidifying agent such as, for example, pyridine, triethylamine or the like, thereby obtaining the acetate (XXXXXII).

PREPARATION PROCESS H OF STARTING SUBSTANCES

The compound (XII) which has been used as the starting substance in the preparation process A and wherein Z is a methoxymethyl group, m is equal to 1, $R^2$ is a halogen atom at the 3 position of the naphthalene ring, n is equal to 1 and $R^6$ is at the 5 position of the naphthalene ring can be prepared according to the following procedure.

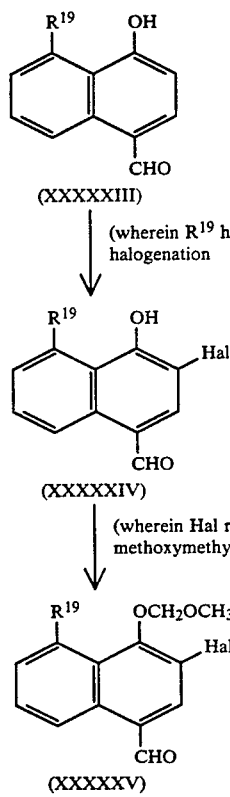

More particularly, the hydroxyaldehyde derivative (XXXXXIII) is reacted with a halogenating agent such as, for example, sulfuryl chloride, bromine or the like to obtain the halide (XXXXXIV).

The halide (XXXXXIV) thus obtained is reacted, as usual, with chloromethyl methyl ether by the use of a de-acidifying agent such as, for example, sodium hydride, diisopropylethylamine or the like to obtain the aldehyde derivative of the general formula (XXXXXV). Production process for starting material I An example of a production process is described below for the compound (XV) used as the starting material in the production process B described above in which $R^6$ is a lower alkoxyalkyl group.

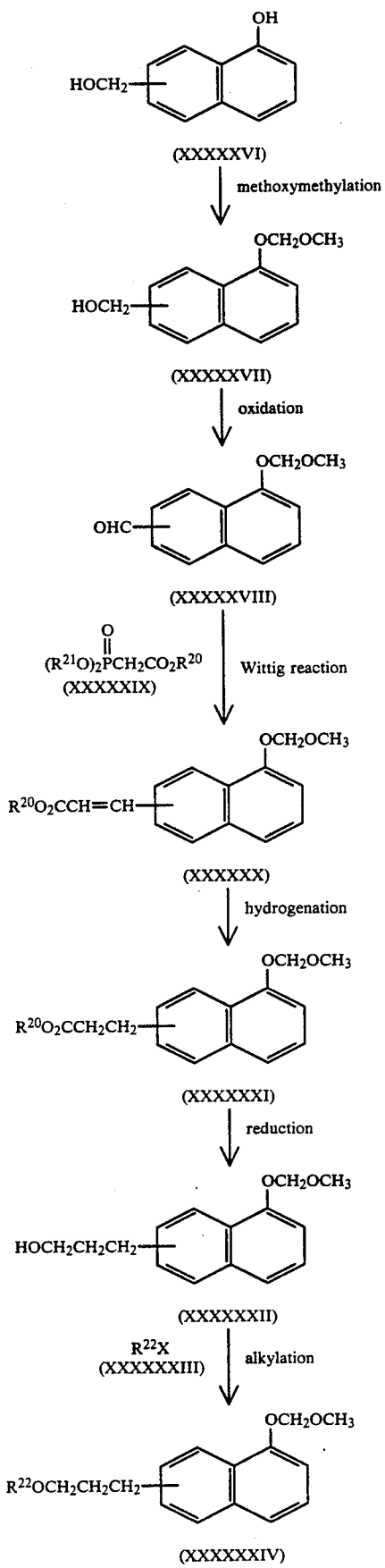

where $R^{20}$, $R^{21}$ and $R^{22}$ each represents a lower alkyl group and X represents a halogen atom.

8-hydroxymethyl-1-naphthol (XXXXXVI) is reacted with chloromethyl methyl ether in a customary manner, for example, by using potassium carbonate as an acid remover to obtain a naphthalene derivative (XXXXXVII).

The resultant naphthalene derivative (XXXXXVII) is reacted with an oxidizing agent, for example, pyridinium dichromate or pyridinium chlorochromate to obtain an aldehyde derivative (XXXXXVIII). The reaction can be conducted using dichloromethane as a reaction solvent at a room temperature.

The resultant aldehyde (XXXXXVIII) is subjected in a customary manner to a Wittig reaction with a phosphate ester (XXXXXIX) to obtain an unsaturated ester derivative (XXXXXX).

The resultant unsaturated ester derivative (XXXXXX) is catalytically hydrogenated by using a catalyst, for example, palladium carbonate to obtain a naphthalene derivative (XXXXXXI). As a reaction solvent, tetrahydrofuran, ethyl acetate, etc. may be used. Specifically, the reaction can be conducted in a hydrogen atmosphere under 1 atm at a room temperature.

The resultant naphthalene derivative (XXXXXXI) is reduced by using a reducing agent, for example, aluminum lithium hydride to obtain an alcohol (XXXXXII).

The resultant alcohol (XXXXXXII) is reacted by a customary manner with a halogenated alkyl (XXXXXXIII) by using a base, for example, sodium hydride, potassium t-butoxide, etc. to obtain an aimed naphthalene derivative (XXXXXIV).

PRODUCTION PROCESS FOR THE STARTING MATERIAL J

One of starting material, naphthalene derivative (XXXXXXVII) for the production process B can be produced by the following method:

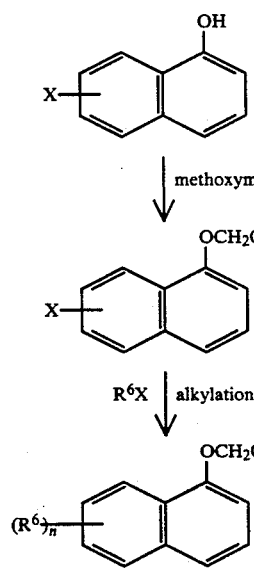

where $R^6$, X, n have the same meanings as described above.

That is, halogenated naphthol derivative (XXXXXXV) can be reacted in a customary manner with a base, for example, sodium hydride or diisopropyl ethylamine, with chloromethyl methyl ether to obtain an naphthol derivative (XXXXXXVI).

The resultant naphthol derivative (XXXXXXVI) is reacted with a strong base and, subsequently, treated with an appropriate halogenated alkyl to obtain an alkylated naphthaol derivative (XXXXXXVII). Specifically, the reaction is carried out using n-butyl lithium as a strong base, ethers such as ether or tetrahydrofuran as a solvent at a reaction temperature from −78° C. to 30° C., preferably, −78° C. to −30° C.

PRODUCTION PROCESS FOR STARTING MATERIAL K

Naphthalene carbaldehyde derivative (XXXXXXXII) as one of the starting materials for the Production Process C can be produced by the following method.

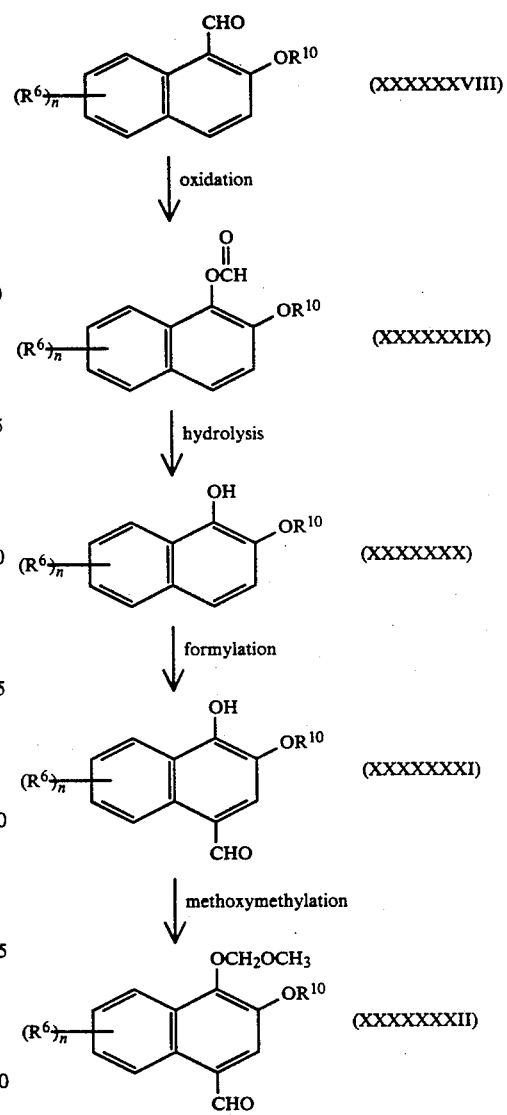

where $R^6$, $R^{10}$ and n have the same meanings as described above.

That is, an aldehyde represented by the general formula (XXXXXXVIII) is treated with hydrogen peroxide or a peracid such as peracetic acid or n-fluoro perbenzoic acid to obtain a formic acid ester derivative (XXXXXXIX). The reaction solvent can properly be selected from water, dichloromethane, chloroform, acetic acid, etc.

The resultant formic acid ester derivative (XXXXXXIX) is alkali-hydrolized by a customary method to obtain a naphthol derivative (XXXXXXX).

The resultant naphthol derivative (XXXXXXX) is reacted with an ortho-ester derivative such as ethyl o-formate or methyl o-formate or dichloromethyl methyl ether to obtain a hydroxyaldehyde derivative (XXXXXXXI). It is possible to properly select aluminum chloride, titanium tetrachloride, etc. as the catalyst, and dichloromethane, chloroform, etc. as the solvent for the reaction.

The resultant hydroxyaldehyde derivative (XXXXXXXI) can be reacted with chloromethyl methyl ether using a base, for example, sodium hydride, diisopropyl ethylamine to obtain a naphthalene carbaldehyde derivative (XXXXXXXII).

In order to describe the effects of the invention in more detail, pharmacological experimental examples of typical compounds of the invention are illustrated below.

EXPERIMENTAL EXAMPLE

Inhibiting Action Against Production of Interleukin-1 (IL-1) from Human Peripheral Blood Monocytes Venous blood was taken out from healthy male volunteers in the presence of citric acid. Mononuclear cells were obtained from the blood by the Ficoll/Paque specific gravity centrifugal method. After washing the cells three times with Hank's balanced salt solution, they were suspended in an RPMI 1640 culture solution containing 10% of an heat-inactivated autoserum at 2 to $3 \times 10^6$ cells/ml. The resulting all suspension was places in a 48-hole plate at 0.5 ml per hole and cultured at 37° C. in 5% $CO_2$/95% air for 2 hours. The culture plates was gently washed three times with RPMI 1640 to remove non-adherent cells therefrom, after which adherent cells were provided as monocytes for the following experiments.

Substances to be tested were each dissolved in ethanol and added to a medium so that the final concentration of ethanol was 0.1%. After the pre-incubation of thirty minutes, lipopolysaccharide was added at a final concentration of 1 μg/ml, followed by cultivation at 37° C., in 5% $CO_2$/95% air for 18 hours.

After completion of the cultivation, the supernatant of the culture solution was passed through a milli-pore filter for use as a measuring sample of extracellular IL-1. The culture solution was freshly added to the adherent cells and the cells were homogenized by sonication, followed by passing through a milli-pore filter for use as a measuring sample of intracellular IL1.

It will be noted that the quantitative determination of IL-1 was made according to the following procedure.

Quantitative Determination of IL-1

The quantitative determination of IL-1 was made according to a usual method wherein thymocytes of C3H/HeJ mice were used and the growth reaction with IL1 in the presence of 1 μl/mL of phytohemagglutinin (made by Difco Inc.) was carried out as an index to incorporation of [$^3$H]-thymidine.

Reference IL-1 used was recombinant human IL-1β (Genzyme Inc.) for investigation of the production of IL-1from human monocytes, and the amount of IL-1 (Unit/ml) in the measuring sample was determined based on the reference curve. The sum of extra- and intracellular IL-1 in each well was calculated, and the IL-1 production inhibiting rate of the respective substances to be tested was determined from comparison with the control.

The following data are added to Table 1. 59 in Example 33, 61 in Example 35, 51 in Example 36, 64 in Example 37 and 63 in Example 41.

TABLE 1

| Compound No. (Example No.) | Inhibiting Percent of IL-1 Production from Human Peripheral Blood Monocytes (3 μM) |
|---|---|
| Compound 1 (Example 1) | 67 |
| Compound 2 (Example 2) | 52 |
| Compound 3 (Example 3) | 72 |
| Compound 5 (Example 5) | 65 |
| Compound 7 (Example 7) | 60 |
| Compound 8 (Example 8) | 55 |
| Compound 10 (Example 10) | 74 |
| Compound 11 (Example 11) | 85 |
| Compound 12 (Example 12) | 69 |
| Compound 14 (Example 14) | 79 |
| Compound 17 (Example 17) | 61 |
| Compound 19 (Example 19) | 74 |
| Compound 21 (Example 21) | 72 |
| Compound 23 (Example 23) | 58 |
| Compound 24 (Example 24) | 60 |
| Compound 29 (Example 29) | 57 |
| Compound 32 (Example 32) | 96 |

From the results of the above experimental examples, it will be apparent that the compounds of the invention have potent inhibiting action on interleukin-1 production.

Moreover, the compounds of the invention have been found to suppress or inhibit the production or release of cytokine represented by IL-1 or various other inflammatory mediators, and these are useful as medicines based on these actions.

The compounds of the invention are effective in curing or preventing various autoimmune diseases including chronic articular rheumatism, systematic lupus erythromatodes, systematic scleroderm, Bechet's disease, periarteritis nodosa, ulcerative colitis, chronic active hepatitis, glomerulonephritis and the like, and various intractable diseases based on the morbid states of inflammatory symptoms such as arthritis deformans, gout, atherosclerosis, psoriasis, atopic dermatitis, lung diseases accompanied by granuloma and various encephalites.

Besides, the compounds are effective as curing and preventing medicines for general symptoms such as the morbid states involving fever, rise in the acute phase reactants or blood sedimentation ratio, and a certain type of diabetes.

Since it has been suggested that IL-1, particularly IL-1β, is a peptide causing hyperlagesia in the peripheral sites, the analgesic action will be expected.

When the compounds of the invention are used as curing and preventing medicines for these diseases, they may be orally dosed in the form of tablets, powder, granules, capsules, syrup and the like, or may be parenterally dosed in the form of a suppository, an injection, an endermic liniment and drops. In the practice of the invention, it is preferred to dose the compound as an oral agent.

The dosage may depend on the type of disease, the extent of symptom and the age. When it is dosed to a human being as an oral agent, the dosage is generally in the range of from 0.01 to 10 mg/kg, preferably from 0.01 to 2 mg/kg and more preferably from 0.1 to 1.5 mg/kg, which is dosed in one to four times per day.

The preparation for the oral or parenteral administration is made by a usual manner using ordinary pharmaceutically acceptable carriers.

Where injections or drops are prepared, pH adjusters, buffers, stabilizers, plasticizers and the like may be added, if necessary, to the principal ingredient and freeze-dried as required to make subcutaneous, intramuscular or intravenous injections or drip injections.

EXAMPLES

Examples are described for further illustration of the compounds and the preparation process of the invention, which should not be construed as limiting the invention thereto.

Preparation processes of starting compounds used in the examples are described as references.

Note) In NMR spectral data, any possible peaks of carboxylic acids may not be detected.

Reference 1

8-Ethyl-1-methoxymethoxynaphthalene

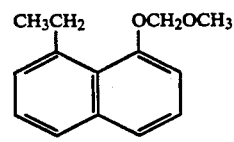

(a) Preparation of 8-(1-hydroxyethyl)-1-naphthol

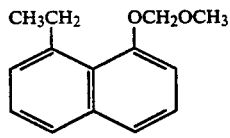

1040 g of 8'-hydroxy-1'-acetonaphthone was dissolved in 8.5 liters of ethanol, to which 131 g of sodium borohydride was added while ice-cooling in order not to allow the temperature of the reaction solution to exceed 30° C. After agitation for 30 minutes at room temperature, excess sodium borohydride was decomposed with 1 liter of acetone. The reaction solution was concentrated under reduced pressure, after which 4 liters of 1N hydrochloric acid was added, followed by extraction with ethyl acetate. The resultant organic phase was washed with a saturated saline solution to remove the excess acid. After drying with anhydrous magnesium sulfate, the solvent was distilled off and a small amount of hexane was added to the resultant residue for crystallization. The crystals were collected by filtration to obtain 1000 g of the captioned compound as light brown crystals.

Melting point: 89°–90° C.

$^1$H-NMR(90 MHz, CDCl$_3$)δ: 1.64(d,J=7.2 Hz,3H), 3.7(br.s,1H), 5.31(q,J=7.2 Hz,1H), 6.94–7.83(m,6H), 10.40(Br.s,1H)

(b) Preparation of 7-ethyl-1-methoxymethoxynaphthalene

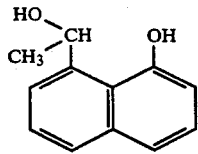

270 g of 8-(1-hydroxyethyl)-1-naphthol was dissolved in 500 ml of tetrahydrofuran and 170 ml of pyridine, followed by dropping 357 g of anhydrous trifluoroacetic acid under ice-cooling conditions in 45 minutes. The reaction solution was agitated under ice-cooling conditions for 0.5 hours, after which 2 liters of ethyl acetate was added. After washing with a saturated saline solution, 1N hydrochloric acid, a saturated saline solution and a sodium hydrogencarbonate saturated aqueous solution in this order, the reaction solution was dried with anhydrous magnesium sulfate. Insoluble matters were removed by filtration and 3.75 liters of tetrahydrofuran was added to the resultant filtrate. 37.5 g of 10% palladium-carbon (water content: 50%) was further added, followed by violent agitation in an atmosphere of hydrogen at 1 atm., for 6 hours. After removal of the palladium-carbon by filtration, the filtrate was concentrated to half in volume. The resultant residue was added under agitation to a saturated sodium hydrogencarbonate aqueous solution, followed by extraction with ethyl acetate. The resultant organic phase was washed with a saturated saline solution. After drying with anhydrous magnesium sulfate, the solvent was distilled off and the resultant residue was dissolved in 1 liter of N,N-dimethylformamide. 69 g of 60% sodium hydride was gently added to the solution under ice-cooling conditions, followed by agitation for further 20 minutes. 160 g of chloromethyl methyl ether was dropped in the resultant reaction solution so that the inner temperature did not exceed 20 C. After further agitation at room temperature for 30 minutes, the reaction solution was poured into iced water and extracted with ethyl acetate. The organic phase was washed with a saturated saline solution and dried with anhydrous magnesium sulfate. The solvent was distilled off, followed by purification by silica gel column chromatography (hexane), thereby obtaining 259 g of the captioned compound as a light yellow oily substance.

$^1$H-NMR(90 MHz, CDCl$_3$)δ: 1.30(d,J=7 Hz,3H), 3.28(q,J=7 Hz,2H), 3.46(s,3H), 5.24(s,2H), 6.90–7.60(m,6H)

Reference 2

1-Methoxy-8-propylnaphthalene

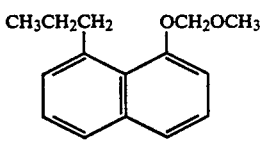

(a) Preparation of 8'-hydroxy-1'-propiononaphthone

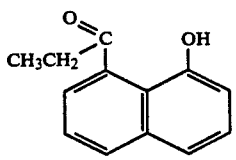

460 g of 1,8-naphthalenecarbolactone was dissolved in 4.2 liters of tetrahydrofuran in a stream of nitrogen and cooled down to −78° C. 900 ml of a diethyl ether solution of 3M ethylmagnesium bromide was dropped in the solution so that the temperature was maintained at −40° C. to −50° C. After the dropping, the solution was returned gently to room temperature. Again, the solution was cooled down to 0° C., to which a saturated ammonium chloride aqueous solution was added, followed by extraction with ethyl acetate. After washing the resultant organic phase with a saturated saline solution, it was dried with anhydrous magnesium sulfate and concentrated under reduced pressure. The resultant residue was purified by silica gel column chromatography (15% ethyl acetate/hexane) to obtain 176 g of the captioned compound as yellow needle crystals.

Melting point: 114°–117° C.

$^1$H-NMR(90 MHz, CDCl$_3$)δ: 1.21(t, J=7 Hz,3H), 3.00(q,J=7 Hz,2H), 7.92(dd,J=3.6 Hz,6 Hz,1H), 7.12–7.68(m,4H), 7.82(dd,J=1.8 Hz,7 Hz,1H), 8.66(br.s,1H)

(b) Preparation of 8-(1-hydroxy-1-propyl)-1-napthol

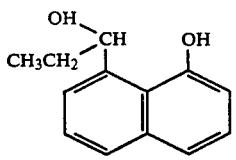

1270 g of 8'-hydroxy-1'-propiononaphthone was dissolved in 15 liters of ethanol and cooled to 10° C. on an ice bath. 143.9 g of sodium borohydride was added to the solution at not higher than 30° C. After agitation for 30 minutes, 1 liter of acetone was gently added, followed by removal of the solvent by distillation under reduced pressure. The concentrated solution was added to 1N hydrochloric acid at 0° C. and extracted with ethyl acetate. The resultant organic phase was washed with a saturated saline solution to an extent of the pH of 6. It was dried with anhydrous magnesium sulfate and concentrated under reduced pressure. Hexane was added to the resultant residue for crystallization, followed by washing with hexane to obtain 1126 g of the captioned compound as light brown crystals.

Melting point: 94°–95° C.

$^1$H-NMR(90 MHz, CDCl$_3$)δ: 0.85(t,J=7 Hz,3H), 1.60–2.32(m,2H), 4.86(t,J=7 Hz,1H) 6.76–7.44(m,5H), 7.66(dd,J=3 Hz,7 Hz,1H)

(c) Preparation of 1-methoxymethoxy-8-propylnaphthalene

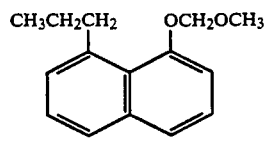

1.9 g of 8-(1-hydroxy-1-propyl)-1-naphthol was dissolved in 34 ml of tetrahydrofuran, to which 8.2 ml of pyridine was added, followed by cooling to 10° C. on an ice bath. 4.4 ml of anhydrous trifluoroacetic acid was added to the solution in 30 minutes, followed by reaction at room temperature for 30 minutes. Ethyl acetate and water were added to the reaction solution for extraction and the resultant organic phase was washed with 1N hydrochloric acid, a saturated sodium hydrogencarbonate aqueous solution and a saturated saline solution in this order and dried with anhydrous magnesium sulfate. The insoluble matters were removed by filtration and 0.36 g of 10% palladium-carbon (water content of 50%) was added to the filtrate, followed by hydrogenation at normal temperatures and pressures for 4 hours. After removal of the palladium-carbon by filtration, the solution was concentrated under reduced pressure to an extent of ⅓ of the total volume. The residual solution was charged into a saturated sodium hydrogencarbonate aqueous solution and extracted with ethyl acetate. The resultant organic phase was washed with a saturated saline solution and dried with anhydrous magnesium sulfate, after which it was concentrated under reduced pressure to obtain 2.3 g of a residue as a brown oily substance. This was dissolved in 20 ml of N,N-dimethylformamide without purification, to which 0.55 g of 60% sodium hydride was added at 0° C. After reaction at room temperature for 10 minutes, the solution was again cooled down to 0° C., followed by addition of 1.43 ml of chloromethyl methyl ether. After further reaction at room temperature for 1 hour, water was added, followed by extraction with ethyl acetate. The resultant organic phase was washed with a saturated saline solution, dried with anhydrous magnesium sulfate and concentrated under reduced pressure. The resultant residue was purified by silica gel column chromatography (2% ethyl acetate/hexane) to obtain 1.9 g of the captioned compound as a brown oily substance.

$^1$H-NMR(90 MHz, CDCl$_3$)δ: 1.02(t,J=7 Hz,3H), 1.40–1.96(m,2H), 3.12–3.36(m,2H) 3.53(s,3H), 5.31(s,2H), 6.96–7.68(m,6H)

Reference 3

5-Ethyl-3-methoxy-4-methoxymethoxy-1-naphthalenecarbaldehyde

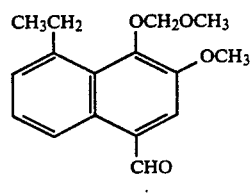

(a) Preparation of 8-ethyl-1-methoxymethoxy-2-naphthalenecarbaldehyde

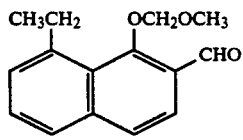

300 g of 8-ethyl-1-methoxymethoxynaphthalene was dissolved in 2.2 liters of absolute ether, in which 1.3 liters of a hexane solution of 1.6M n-butyl lithium was gently dropped at −20° C. in a stream of nitrogen. After the dropping, the solution was raised to room temperature and agitated for 2 hours. It was again cooled down to −40° C., to which 215 ml of N,N-dimethylformamide was added. After agitation for 30 minutes, 100 ml of water was added and the resultant organic phase was washed with a saturated saline solution. After drying with anhydrous magnesium sulfate, the solvent was distilled off and the residue was purified by silica gel column chromatography (5% ethyl acetate/hexane) to obtain 253 g of the captioned compound as colorless crystals.

Melting point: 41.5°-42.5° C.

$^1$H-NMR(90 MHz, CDCl$_3$)δ: 1.31(t,J=7 Hz,3H), 3.30(q,J=7 Hz,2H), 3.53(s,3H), 5.09(s,2H), 7.21-7.87(m,5H), 10.46(s,1H)

(b) Preparation of 8-ethyl-2-methoxy-1-methoxymethoxynaphthalene

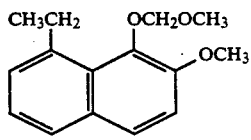

220 g of 8-ethyl-1-methoxymethoxy-2-naphthalenecarbaldehyde was dissolved in 1540 ml of dichloromethane, to which 186 g of 80 to 85% m-chloroperbenzoic acid was added portion by portion. The reaction solution generated heat and was gently refluxed. The reaction solution was ice-cooled, to which 200 ml of a saturated sodium thiosulfate aqueous solution was added. The precipitated insoluble matters were removed by filtration and washed with dichloromethane. The filtrate was washed with a saturated sodium hydrogencarbonate aqueous solution and a saturated saline solution and dried with anhydrous magnesium sulfate. After removal of the solvent by distillation, 254 g of the resultant residue was dissolved in 500 ml of methanol, to which 89 g of potassium hydroxide preliminarily dissolved in 200 ml of water was added, followed by refluxing for 20 minutes. The reaction solution was poured into 700 mo of cooled 2N hydrochloric acid and extracted with ethyl acetate. The resultant organic phase was washed with a saturated saline solution and dried with anhydrous magnesium sulfate, from which the solvent was distilled off. 278 g of the resultant residue was dissolved in 600 ml of N,N-dimethylformamide, to which 500 g of anhydrous potassium carbonate and 256 g of methyl iodide were added, followed by agitation at 60° C. for 2 hours. The insoluble matters were filtered off and washed with ethyl acetate. Water was added to the resultant filtrate, which was extracted with ethyl acetate. The resultant organic phase was washed with a saturated saline solution and dried with anhydrous magnesium sulfate. After removal of the solvent by distillation, the resultant residue was purified by silica gel column chromatography to obtain 166 g of the caption compound as a yellow oily substance.

$^1$H-NMR(90 MHz, CDCl$_3$)δ: 1.32(t,J=7 Hz,3H), 3.36(q,J=7 Hz,2H), 3.58(s,3H), 3.95(s,3H), 5.16(s,2H), 7.16-7.70(m,5H)

(c) Preparation of 5-ethyl-4-hydroxy-3-methoxy-1-naphthalenecarbaldehyde

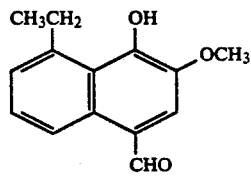

200 g of 8-ethyl-2-methoxy-1-methoxymethoxynaphthalene was dissolved in 1 liter of acetone, to which dilute hydrochloric acid (concentrated hydrochloric acid 81 ml/water 200 ml) was added under ice-cooling conditions, after which the ice bath was removed, followed by agitation at room temperature for 5 hours. The reaction solution was poured into iced water and extracted with ethyl acetate. The resultant organic phase was washed with a saturated saline solution and dried with anhydrous magnesium sulfate. After removal of the solvent by distillation, 178 g of the resultant oily substance was dissolved in dichloromethane, to which 178 ml of titanium tetrachloride was gently added under ice-cooling conditions. After agitation for 30 minutes, 121 ml of dichloromethyl methyl ether was gradually added and agitated for 30 minutes. Iced water was gently added to the reaction solution, followed by extraction with ethyl acetate. The resultant organic phase was washed with a saturated saline solution and dried with anhydrous magnesium sulfate. After removal of the solvent by distillation, the resultant residue was washed with a mixture of hexane/isopropyl ether (1:1) to obtain 110 g of the caption compound as yellowish brown crystals.

Melting point: 114°-115° C.

$^1$H-NMR(90 MHz, CDCl$_3$)δ: 1.33(t,J=7 Hz,3H), 3.37(q,J=7 Hz,2H), 4.09(s,3H), 7.05(s,1H), 7.20-7.56(m,2H), 7.77(s,1H), 8.97(dd,J=1.6 Hz,8 Hz,1H), 10.39(s,1H)

(d) Preparation of 5-ethyl-3-methoxy-4-methoxymethoxy-1-naphthalenecarbaldehyde

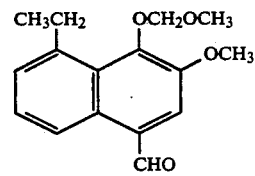

324 g of 5-ethyl-4-hydroxy-3-methoxy-1-naphthalenecarbaldehyde was dissolved in 1 liter of N,N-dimethylformaldehyde, to which 68 g of 60% sodium hydride was gently added under ice-cooling conditions. After agitation for 10 minutes, 128 ml of chloromethyl methyl ether was gradually added so that the reaction temperature did not exceed 15° C. After agitation at room temperature for 20 minutes, the reaction solution was poured into iced water and extracted with ethyl acetate. The resultant organic phase was washed with a saturated saline solution and dried with anhydrous magnesium sulfate. The solvent was distilled off and the resultant residue was purified by silica gel column chromatography (5% ethyl acetate/hexane) to obtain 288 g of the captioned compound as a brown oily substance.

¹H-NMR(90 MHz, CDCl₃)δ: 1.30(t,J=7 Hz,3H), 3.36(q,J=7 Hz,2H), 3.55(s,3H), 4.00(s,3H), 5.31(s,2H), 7.20–7.50(m,2H), 7.76(s,1H), 8.90(dd,J=2.6 Hz,7 Hz,1H), 10.36(s,1H)

Reference 4
3-Methoxy-4-methoxymethoxy-5-propyl-1-naphthalenecarbaldehyde

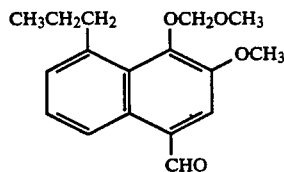

(a) Preparation of 1-methoxymethoxy-8-propyl-2-naphthalenecarbaldehyde

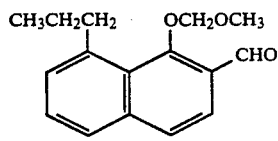

350 g of 1-methoxymethoxy-8-propylnaphthalene was dissolved in 3 liters of absolute ether and cooled down to −35° C. 1.43 liters of a hexane solution of 1.6M n-butyl lithium was added to the solution at a temperature not higher than −30° C., followed by gradually raising the temperature and reaction at room temperature for further 1 hour. The reaction solution was again cooled down to −40° C., to which 222 ml of N,N-dimethylformamide was added in 15 minutes. The mixture was slowly raised to 10° C., to which water was added portion by portion, followed by extraction with ethyl acetate. The resultant organic phase was washed with a saturated saline solution and dried with anhydrous magnesium sulfate, after which it was concentrated under reduced pressure to obtain 460 g of a black reside. This residue was purified by silica gel column chromatography (5% ethyl acetate/hexane) to obtain 326 g of the captioned compound as a brown oily substance.

¹H-NMR(90 MHz, CDCl₃)δ: 0.96(t,J=7 Hz,3H), 1.40–1.92(m,2H), 3.04–3.30(m,2H), 3.52(s,3H), 5.06(s,2H), 7.16–7.88(m,5H), 10.48(s,1H)

(b) Preparation of 2-methoxy-1-methoxymethoxy-8-propylnaphthalene

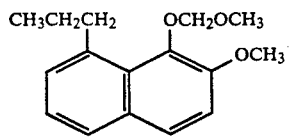

1.6 g of 1-methoxy-8-propyl-2-naphthalenecarbaldehyde was dissolved in 16 ml of dichloromethane, to which 1.6 g of 80 to 85% m-chloroperbenzoic acid was add, followed by heating under reflux for 30 minutes. The reaction solution was returned to room temperature and the organic phase (?) was washed with a sodium thiosulfate aqueous solution, a saturated sodium hydrogencarbonate aqueous solution and a saturated saline solution in this order and dried with anhydrous magnesium sulfate. Thereafter, it was concentrated under reduced pressure. 1.6 g of the resultant brown oily residue was dissolved in 5.2 ml of methanol without purification, to which a potassium hydroxide aqueous solution (potassium hydroxide 0.52 g/water 5.2 ml) was added, followed by reaction at 60° C. for 15 minutes. The reaction solution was returned to room temperature and rendered acidic by means of dilute hydrochloric acid, and was extracted with ethyl acetate. The resultant organic phase was washed with a saturated sodium hydrogencarbonate aqueous solution and a saturated saline solution in this order and dried with anhydrous magnesium sulfate, after which it was concentrated under reduced pressure. 1.5 g of the resultant black oily residue was dissolved in 15 ml of N,N-dimethylformamide without purification, to which 3.7 g of methyl iodide and 4.6 g of anhydrous potassium carbonate were added, followed by reaction at 60° C. for 1 hour. After removal of the solid matters by filtration, water was added, followed by extraction with ethyl acetate. The organic phase was washed with a saturated saline solution and dried with anhydrous magnesium sulfate, after which it was concentrated under reduced pressure. The resultant reside was purified by silica gel column chromatography (2% ethyl acetate/hexane) to obtain 1.3 g of the captioned compound as a brown oily substance.

¹H-NMR(90 MHz, CDCl₃)δ: 0.96(t,J=7 Hz,3H), 1.68(m,2H), 3.08–3.40(m,2H), 3.56(s,3H), 3.92(s,3H), 5.14(s,2H), 7.06–7.26(m,3H), 7.38–7.62(m,2H)

(c) Preparation of 4-hydroxy-3-methoxy-5-propyl-1-naphthalenecarbaldehyde

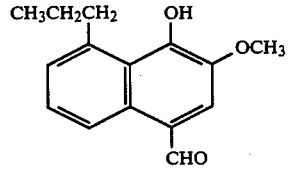

206 g of 2-methoxy-1-methoxymethoxy-8-propylnaphthalene was dissolved in 1160 ml of acetone and cooled to 0° C. Diluted hydrochloric acid (concentrated hydrochloric acid 84 ml/water 206 ml) was added to the solution in 15 minutes, which was returned to room temperature at which the reaction was effected at 20° C. for 5 hours, followed by addition of water and extraction with ethyl acetate. The resultant organic phase was washed with a saturated saline solution to neutrality, dried with anhydrous magnesium sulfate, and concentrated under reduced pressure. 173 g of the resultant brown oily substance was dissolved in 1350 g of dichloromethane without purification and cooled down to 0° C. 176.3 ml of titanium tetrachloride was dropped in the solution at 5° C. or below, to which 114.3 ml of dichloromethyl methyl ether was added at 5° C. or below at which the reaction was carried out for 10 minutes. The reaction solution was slowly added to iced water and extracted with ethyl acetate. The resultant organic phase was washed with a a saturated sodium hydrogencarbonate aqueous solution and a saturated saline solution in this order and dried with anhydrous magnesium sulfate, and was concentrated under reduced pressure. The resultant crystals were washed with a 30% isopropyl ether/hexane solution to obtain 103 g of the captioned compound as yellowish brown crystals.

Melting point: 128°–129° C.

1H-NMR(90 MHz, CDCl3)δ: 1.00(t,J=7 Hz,3H), 1.46–1.92(m,2H), 3.14–3.36(m,2H), 4.06(s,3H), 7.16–7.54(m,2H), 7.74(s,1H), 8.96(dd,J=1.8 Hz,9 Hz,1H), 10.38(s,1H)

(d) Preparation of 3-methoxy-4-methoxymethoxy-5-propyl-1-naphthalenecarbaldehyde

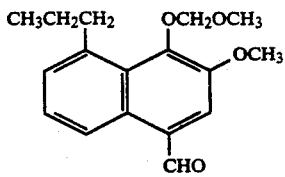

322 g of 4-hydroxy-3-methoxy-5-propyl-1-naphthalenecarbaldehyde was dissolved in 1.3 liters of N,N-dimethylformamide and cooled to 10° C. 63.3 g of 60% sodium hydride was added to the solution at 30° C. or below and agitated for 20 minutes. The reaction solution was cooled to 5° C., to which 190 ml of chloromethyl methyl ether was added. After agitation at room temperature for 2 hours, the solution was poured into iced water and extracted with ethyl acetate. The resultant organic phase was washed with a saturated saline solution, after which it was dried with anhydrous magnesium sulfate and concentrated under reduced pressure. The resultant residue was purified by silica gel column chromatography (10% ethyl acetate/hexane) to obtain 294.5 g of the captioned compound as a brown oily substance.

1H-NMR(90 MHz, CDCl3)δ: 0.96(t,J=7 Hz,3H), 1.42–1.90(m,2H), 3.12–3.42(m,2H), 3.54(s,3H), 4.00(s,3H), 5.28(s,2H), 7.14–7.48(m,2H), 7.76(s,1H), 8.99(dd,J=1.8 Hz,7 Hz,1H), 10.45(s,1H)

Reference 5

3-Ethoxy-5-ethyl-4-methoxymethoxy-1-naphthalenecarbaldehyde

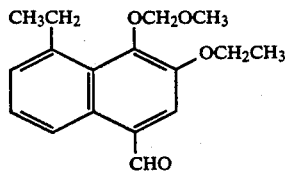

In Reference 3(b), ethyl iodide was used instead of methyl iodide, followed by the procedures of References 3(c) and 3(d), thereby obtaining the captioned compound as a yellowish brown oily substance.

1H-NMR(90 MHz, CDCl3)δ: 1.28(t,J=7.7 Hz,3H), 1.50(t,J=7.7 Hz,2H), 3.36(q,J=7.7 Hz,2H), 3.52(s,3H), 4.20(q,J=7.7 Hz,2H), 5.32(s,2H), 7.18–7.48(m,2H), 7.72(s,1H), 8.88(dd,J=2.6 Hz,7.7Hz,1H), 10.30(s,1H)

Reference 6

5'-Ethyl-3'-methoxy-4'-methoxymethoxy-1'-acetonaphthone

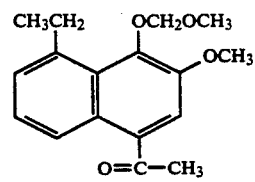

2 g of 5-ethyl-3-methoxy-4-methoxymethoxy-1-naphthalenecarbaldehyde was dissolved in 20 ml of absolute tetrahydrofuran, to which 11.5 ml of an ethyl solution of 1.12M methyl lithium was added at −78° C. After 30 minutes, an ammonium chloride aqueous solution was added to the solution and extracted with ethyl acetate. The resultant organic phase was dried with anhydrous magnesium sulfate and the solvent was distilled off to obtain 2.1 g of a brown oily substance. This substance was dissolved in 20 ml of dichloromethane without isolation and purification, to which 30 g of manganese dioxide was added, followed by agitation at room temperature for 20 hours. The insoluble matters were removed by filtration and the filtrate was concentrated, followed by purification by silica gel column chromatography (10% ethyl acetate/hexane) to obtain 1.3 g of the captioned compound as a yellow oily substance.

1H-NMR(90 MHz, CDCl3)δ: 1.27(t,J=7 Hz,3H), 2.70(s,3H), 3.34(q,J=7.5 Hz,2H), 3.53(s,3H), 3.96(s,3H), 5.21(s,2H), 7.20–7.31(m,2H), 8.21–8.37(m,1H)

Reference 7

5'-Ethyl-3'-methoxy-4'-methoxymethoxy-1'-valeronaphthone

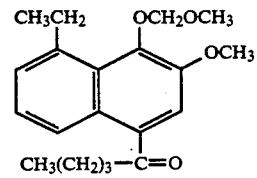

5-Ethyl-3-methoxy-4-methoxymethoxy-1-naphthalenecarbaldehyde and a hexane solution of 1.6M n-butyl lithium were used and treated in the same manner as in Reference 6 to obtain the captioned compound as a yellow oily substance.

1H-NMR(90 MHz, CDCl3)δ: 0.80–1.60(m,3H), 1.12–1.92(m,7H), 2.96(t,J=7 Hz,2H) 3.34(q,J=7 Hz,2H), 3.54(s,3H), 3.96(s,3H), 5.18(s,2H), 7.16–7.32(m,2H), 7.42(s,1H), 7.92–8.10(m,1H)

Reference 8

1-(t-Butyldimethylsilyl)oxymethyl-4-methoxymethoxy-5-methylnaphthalene

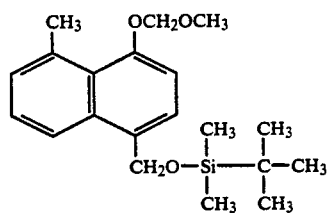

(a) Preparation of 4-hydroxy-5-methyl-1-naphthalenecarbaldehyde

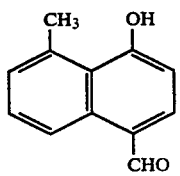

101.9 g of 8-methyl-1-naphthol was dissolved in 815 ml of dichloromethane, in which 141.6 ml of titanium tetrachloride was gradually dropped under ice-cooling conditions. Thereafter, 93.7 ml of dichloromethyl methyl ether was gradually dropped under ice-cooling conditions. After agitation for 10 minutes, 200 ml of water was gently dropped under ice-cooling conditions. The reaction solution was extracted with ethyl acetate and the resultant organic phase was washed with water. After drying with anhydrous magnesium sulfate, the solvent was distilled off and the resultant crystals were washed with chloroform to obtain 80 g of the captioned compound as brown crystals.

Melting point: 208° C. (decomposed)
$^1$H-NMR(90 MHz, DMSO-$d_6$)δ: 2.88(s,3H), 6.98(d,J=7 Hz,1H), 7.10–7.60(m,2H), 7.84(d,J=7 Hz,1H), 9.06(br.d,J=7 Hz,1H), 10.02(s,1H) 11.24(s,1H)

(b) Preparation of 4-methoxymethoxy-5-methyl-1-naphthalenecarbaldehyde

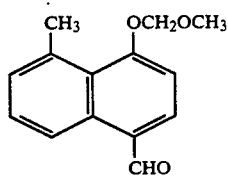

18 g of 4-hydroxy-5-methyl-1-naphthalenecarbaldehyde and 15 g of N,N-diisopropylethylamine were dissolved in 200 ml of dichloromethane, in which 9.3 g of chloromethyl methyl ether was gradually dropped under ice-cooling conditions. After agitation at room temperature overnight, the reaction solution was washed with water and dried with anhydrous magnesium sulfate. The solvent was distilled off and the residue was purified by silica gel column chromatography (10% ethyl acetate/hexane) to obtain 16.8 g of the captioned compound as light brown crystals.

Melting point: 42°–43° C.
$^1$H-NMR(90 MHz, CDCl$_3$)δ: 2.90(s,3H), 3.54(s,3H), 5.36(s,3H), 7.06(d,J=7.7 Hz,1H), 7.20–7.56(m,2H), 7.78(d,J=7.7 Hz,1H), 9.16(br.d,J=7.7 Hz,1H), 10.10(s,1H)

(c) Preparation of 1-hydroxymethyl-4-methoxymethoxy-5-methylnaphthalene

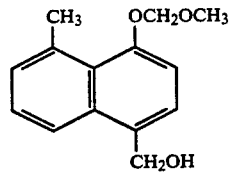

1.23 g of sodium borohydride was added to an ethanol (100 ml) solution of 15 g of 4-methoxymethoxy-5-methyl-1-naphthalenecarbaldehyde at room temperature and agitated for 30 minutes. Water was added to the reaction solution and the resultant crystals were collected by filtration and dried to obtain 14 g of the captioned compound as light brown crystals.

Melting point: 91°–93° C.
$^1$H-NMR(90 MHz, CDCl$_3$)δ: 1.78(br.t,J=5 Hz,1H), 2.91(s,3H), 3.51(s,3H), 4.96(br,d,J=5 Hz,2H), 5.26(s,2H), 6.92(d,J=7 Hz,1H), 7.10–7.42(m,3H), 7.87(m,1H)

(d) Preparation of 1-(t-butyldimethylsilyl)oxymethyl-4-methoxymethoxy-5-methylnaphthalene

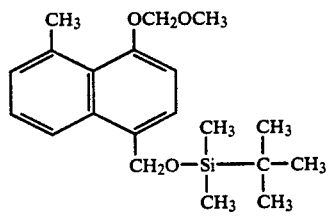

13.7 g of t-butylchlorodimethylsilane was added to an N,N-dimethylaminopyridine (100 ml) solution of 14 g of 1-hydroxymethyl-4-methoxymethoxy-5-methylnaphthalene, 6.64 g of imidazole, and 0.4 g of 4-dimethylaminopyridine and agitated at room temperature overnight. Water was added to the reaction solution, followed by extraction with ethyl acetate. Thereafter, the resultant organic phase was washed with water and then with a saturated saline solution. After drying with anhydrous magnesium sulfate, the solvent was distilled off and the residue was purified by silica gel column chromatography (5% ethyl acetate/hexane) to obtain 19 g of the captioned compound as a light brown oily substance.

$^1$H-NMR(90 MHz, CDCl$_3$)δ: 0.10(s,6H), 0.93(s,9H), 2.89(s,3H), 3.49(s,3H), 5.01(s,2H), 5.25(s,2H), 6.95(d,J=7 Hz,1H), 7.06–7.40(m,3H), 7.72(m,1H)

Reference 9

3-Methoxy-4-methoxymethoxy-5-methyl-1-naphthalenecarbaldehyde

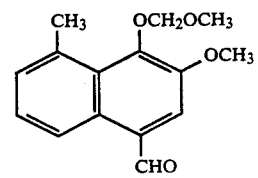

(a) 1-(t-butyldimethylsilyl)oxymethyl-4-methoxymethoxy-5-methyl-3-naphthalenecarbaldehyde

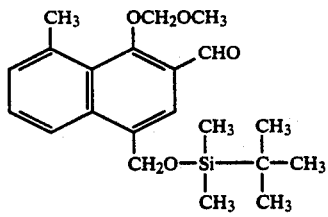

52 ml of a hexane solution of 1.6M n-butyl lithium was dropped in an absolute ether (110 ml) solution of 19 g of 1-(t-butyldimethylsilyl)oxymethyl-4-methoxymethoxy-5-methylnaphthalene and agitated for 1 hour. After ice cooling, 8.5 ml of N,N-dimethylformamide was dropped in the reaction solution and the ice bath was removed, followed by agitation for 1 hour until room temperature was reached. Iced water was added to the reaction solution, followed by extraction with ethyl acetate. The resultant organic phase was washed with a saturated saline solution and dried with anhydrous magnesium sulfate. After removal of the solvent by distillation, the residue was purified by silica gel column chromatography (2% ethyl acetate/hexane) to obtain 14.1 g of the captioned compound as a brown oily substance.

$^1$H-NMR(90 MHz, CDCl$_3$)δ:
0.11(s,6H), 0.93(s,9H), 2.89(s,3H), 3.51(s,3H), 5.04(s,2H), 7.18–7.52(m,2H), 7.75–7.91(m,2H), 10.38(s,1H)

(b) Preparation of 1-(t-butyldimethylsilyl)oxymethyl-3-methoxy-4-methoxymethoxy-5-methylnaphthalene

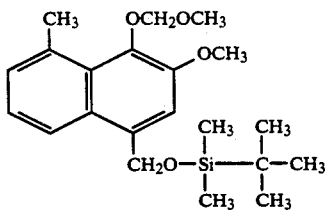

10.8 g of 80 to 85% m-chloroperbenzoic acid was added to a dichloromethane (130 ml) solution of 10 g of 1-(t-butyldimethylsilyl)oxymethyl-4-methoxymethoxy-5-methyl-3-naphthalenecarbaldehyde and heated for 1 hour under reflux. The reaction solution was washed with a sodium thiosulfate aqueous solution, after which it was further washed with water, a saturated sodium hydrogencarbonate aqueous solution and a saturated saline solution in this order and dried with anhydrous magnesium sulfate, followed by removal of the solvent by distillation. 9.3 g of the resultant brown oily substance and 2.1 g of sodium hydride were suspended in 21 ml of methanol and 21 ml of water and refluxed for 15 minutes. After cooling, the suspension was rendered acidic by means of dilute hydrochloric acid, followed by extraction with ethyl acetate. After washing with a saturated saline solution, the extract was dried with anhydrous magnesium sulfate, from which the solvent was distilled off. 5 ml of methyl iodide was added to an N,N-dimethylformamide (100 ml) solution of 8.5 g of the resultant brown oily substance and 22.1 g of potassium carbonate, followed by reaction at 60° to 70° C. for 1 hour. The insoluble matters were removed by filtration and the resultant filtrate was diluted with ether. After washing with water, the diluted filtrate was washed with a saturated saline solution and dried with magnesium sulfate. After removal of the solvent by distillation, the residue was purified by silica gel column chromatography (5% ethyl acetate/hexane) to obtain 7.3 g of the captioned compound as a brown oily substance.

$^1$H-NMR(90 MHz, CDCl$_3$)δ:
0.14(s,6H), 0.98(s,9H), 2.92(s,3H), 3.57(s,3H), 3.94(s,3H), 5.11(s,4H), 7.10–7.66(m,4H)

(c) Preparation of 1-hydroxymethyl-3-methoxy-4-methoxymethoxy-5-methylnaphthalene

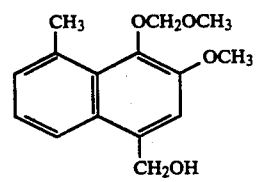

32 ml of a tetrahydrofuran solution of 1M tetra-n-butylammonium fluoride was added to a tetrahydrofuran (150 ml) solution of 7.3 g of 1-(t-butyldimethylsilyl)oxymethyl-3-methoxy-4-methoxy-methoxy-5-methylnaphthalene and agitated for 1 hour. Water was added to the reaction solution and extracted with ethyl acetate, and the resultant organic phase was washed with water and a saturated saline solution, followed by drying with anhydrous magnesium sulfate and removal of the solvent by distillation to obtain the captioned compound as an oily substance. This compound was used for subsequent reaction without purification.

$^1$H-NMR(90 MHz, CDCl$_3$)δ:
2.28(s,1H), 2.92(s,3H), 3.56(s,3H), 3.88(s,3H), 5.01(s,2H), 5.11(s,2H), 7.14–7.36(m,3H), 7.75(m,1H)

(d) Preparation of 3-methoxy-4-methoxymethoxy-5-methyl-1-naphthalenecarbaldehyde

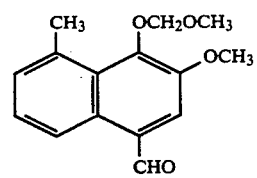

37 g of manganese dioxide was added to a dichloromethane (150 ml) solution of 1-hydroxymethyl-3-methoxy-4-methoxymethoxy-5-methylnaphthalene and agitated at room temperature overnight. The reaction suspension was filtered through Celite and the resultant filtrate was concentrated under reduced pressure, followed by purification by silica gel column chromatography (5% ethyl acetate/hexane) to obtain 3.8 g of the captioned compound as light yellowish brown crystals.

Melting point: 48°–50° C.

$^1$H-NMR(90 MHz, CDCl$_3$)δ: 2.94(s,3H), 3.55(s,3H), 3.99(s,3H), 5.29(s,2H), 7.18–7.48(m,2H), 7.77(s,1H9, 8.90(m,1H9, 10.43(s,1H)

Reference 10

3,5-Dimethoxy-4-methoxymethoxy-1-naphthalenecarbaldehyde

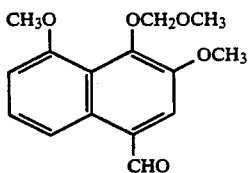

4-Hydroxy-5-methoxy-1-naphthalenecarbaldehyde was treated in the same manner as in References 8, 9 to obtain the captioned compound as a yellow oily substance.

¹H-NMR(90 MHz, CDCl₃)δ: 3.66(s,3H), 3.97(s,3H), 4.01(s,3H), 5.20(s,2H), 6.90(m,1H), 7.42(t,J=8.2 Hz,1H), 7.80(s,1H), 8.66(m,1H)

Reference 11

8-Isopropyl-1-methoxymethoxynaphthalene

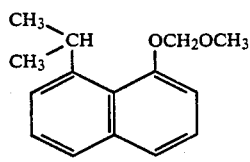

(a) Preparation of 8-(1-hydroxy-1-methyl-1-ethyl)-1-naphthol

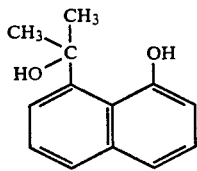

20.0 g of 1,8-naphthalenecarbolactone was dissolved in 200 ml of absolute tetrahydrofuran and cooled down to −60° C. In the solution was dropped 140 ml of a diethyl ether solution of 3.0M methylmegnesium bromide so that the inside of the system was −30° C. or below. After agitation at −30° C. for 1 hour, a saturated ammonium chloride aqueous solution was added, followed by extraction with ethyl acetate. The resultant organic phase was dried with anhydrous magnesium sulfate and the resulting filtrate was concentrated under reduced pressure. The residue was purified by silica gel column chromatography (10% ethyl acetate/hexane) to obtain 14.3 g of the captioned compound as white crystals.

Melting point (°C.):

¹H-NMR(90 MHz, CDCl₃)δ: 1.81(s,6H), 6.91–7.42(m,5H), 7.66(dd,J=1.8 Hz,7.7 Hz,1H)

(b) Preparation of 8-isopropenyl-1-naphthyl acetate

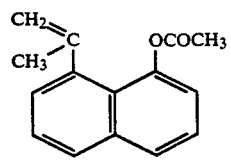

11.3 g of 8-(1-hydroxy-1-methyl-1-ethyl)-1-naphthol was dissolved in 24 ml of pyridine, to which 12 ml of anhydrous acetic acid was added. The solution was raised in temperature to 60° C. and heated for 6 hours under agitation. Water was added to the reaction solution, followed by extraction with ethyl acetate. The resulting organic phase was washed with a 2N hydrochloric acid aqueous solution, water and a saturated saline solution in this order, dried with anhydrous magnesium sulfate, and concentrated under reduced pressure. The resultant residue was purified by silica gel column chromatography (10% ethyl acetate/hexane) to obtain 3.6 g of the captioned compound as an oily substance. ¹H-NMR(90 MHz, CDCl₃)δ: 2.16(t,J=0.6 Hz,3H), 2.27(s,3H), 4.81(m,1H), 5.06(m,1H), 6.98–7.80(m,6H)

(c) Preparation of 8-isopropyl-1-naphthyl acetate

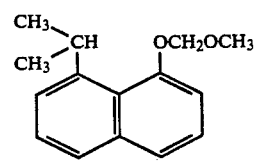

3.6 g of 8-isopropenyl-1-naphthyl acetate was dissolved in 100 ml of ethanol, to which 0.2 g of 10% palladium-carbon (water content of 50%) was added, followed by hydrogenation at normal temperatures and normal pressure for 20 hours. After removal of the palladium-carbon by filtration, the resulting filtrate was concentrated under reduced pressure. The residue was purified by silica gel column chromatography (3% ethyl acetate/hexane) to obtain 1.72 g of the captioned compound as an oily substance.

¹H-NMR(90 MHz, CDCl₃)δ: 1.36(d,J=6.7 Hz,6H), 2.40(s,3H), 3.85–4.16(m,1H), 7.0–7.8(m,6H)

(d) Preparation of 8-isopropyl-1-methoxymethoxy naphthalene

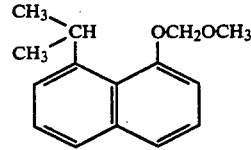

8.40 g of 8-isopropyl-1-naphthyl acetate was dissolved in 50 ml of methanol, to which 2.2 g of sodium methoxide was added at room temperature, followed by agitation for 10 minutes as it is. Water was added to the solution, which was rendered acidic by the use of 1N hydrochloric acid, followed by extraction with ethyl acetate. The resultant organic phase was washed with a saturated saline solution and dried with anhydrous magnesium sulfate, from which the solvent was distilled off. The resulting residue was dissolved in 30 ml of dimethylformamide without purification, to which 1.94 g of 60% sodium hydride was added at room temperature.

After 10 minutes, it was cooled down to 0° C., to which 5.96 g of chloromethyl methyl ether was added, followed by agitation for 15 minutes as it is. Water was added to the solution which was extracted with ethyl acetate, and th resultant organic phase was washed with a saturated saline solution and dried with anhydrous magnesium sulfate, from which the solvent was distilled off. The resultant residue was purified by silica gel column chromatography (3% ethyl acetate/hexane) to obtain 8.13 g of the captioned compound as a light yellow oily substance.

$^1$H-NMR(90 MHz, CDCl$_3$)δ: 1.36(d,J=6.7 Hz,6H), 3.54(s,3H), 4.29–4.65(m,1H), 5.32(s,2H), 7.00–7.64(m,6H)

Reference 12

5-Isopropyl-3-methoxy-4-methoxymethoxy-1-naphthalenecarbaldehyde

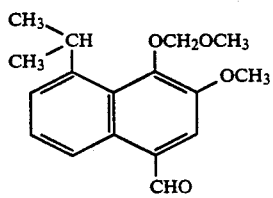

8-Isopropyl-1-methoxymethoxynaphthalene was treated in the same manner as in Reference 3, thereby obtaining the captioned compound as a light yellow oily substance.

$^1$H-NMR(90 MHz, CDCl$_3$)δ: 1.34(d,J=6.7 Hz,6H), 3.53(s,3H), 3.98(s,3H), 4.43–4.77(m,1H), 5.26(s,2H), 7.30–7.57(m,2H), 7.76(s,1H), 8.93(dd,J=2.0 Hz,6.9 Hz,1H), 10.45(s,1H)

Reference 13

3-Methoxy-4-methoxymethoxy-1-naphthalenecarbaldehyde

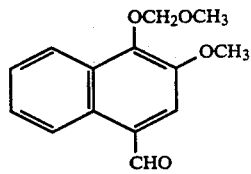

4-Hydroxy-1-naphthalenecarbaldehyde was treated in the same manner as in References 8,9, thereby obtaining the captioned compound as light yellow crystals.

Melting point: 68°–68.5° C.

$^1$H-NMR(90 MHz, CDCl$_3$)δ: 3.59(s,3H), 4.00(s,3H), 5.40(s,2H), 7.37–7.60(m,2H), 7.76(s,1H), 8.10–8.32(m,1H), 8.86–9.10(m,1H), 10.33(s,1H)

Reference 14

4-Methoxymethoxy-3-methyl-1-naphthalenecarbaldehyde

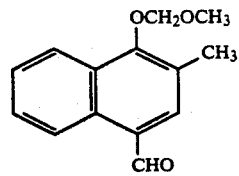

4-Hydroxy-3-methyl-1-naphthalenecarbaldehyde was treated in the same manner as in Reference 3(d), thereby obtaining the captioned compound as a light yellow oily substance.

$^1$H-NMR(90 MHz, CDCl$_3$)δ: 2.51(s,3H), 3.63(s,3H), 5.16(s,2H), 7.40–7.64(m,2H), 7.74(s,1H), 7.96–8.16(m,1H), 9.04–9.24(m,1H), 10.16(s,1H)

Reference 15

3-Chloro-5-ethyl-4-methoxymethoxy-1-naphthalenecarbaldehyde

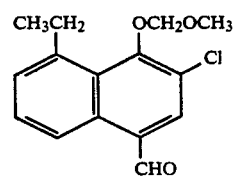

(a) Preparation of 5-ethyl-4-hydroxy-1-naphthalenecarbaldehyde

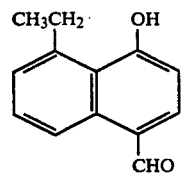

24.0 g of 8-ethyl-1-naphthol was dissolved in 200 ml of dichloromethane, in which 30.6 ml of titanium tetrachloride was gradually dropped under ice-cooling conditions. Thereafter, 20.3 ml of dichloromethyl methyl ether was gradually dropped under ice-cooling condition. After agitation for 10 minutes, 50 ml of water was gradually dropped under ice-cooling conditions. The reaction solution was extracted with ethyl acetate and the organic phase was washed with water. After drying with anhydrous magnesium sulfate, the solvent was distilled off and the resultant crystals were washed with a mixed solvent of chloroform and isopropyl ether (1:1) to obtain 15.9 g of the captioned compound as yellowish brown crystals.

Melting point: 193°–194° C.

$^1$H-NMR(90 MHz, DMSO-d$_6$)δ: 1.26(d,J=7 Hz,3H), 3.32(q,J=7 Hz,2H), 7.04(d,J=8 Hz,1H), 7.33(dd,J=1.4 Hz,8 Hz,1H) 7.56((t,J=8 Hz,1H), 7.94(d,J=8 Hz,1H), 9.17(dd,J=1.4 Hz,8 Hz,1H), 10.07(s,1H), 11.40(s,1H)

(b) Preparation of 3-chloro-5-ethyl-4-hydroxy-1-naphthalenecarbaldehyde

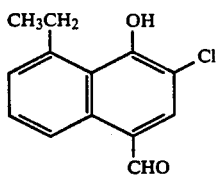

0.81 g of 5-ethyl-4-hydroxy-1-naphthalenecarbaldehyde and 0.49 ml of sulfuryl chloride were heated in 30 ml of benzene under reflux for 30 minutes. The reaction solution was returned to room temperature and poured into water, followed by extraction with ethyl acetate. The resultant organic phase was washed with a saturated saline solution and dried with anhydrous magnesium sulfate, followed by concentration under reduced pressure. The resultant crystals were washed with isopropyl ether to obtain 0.8 g of the captioned compound as yellowish brown crystals.

Melting point: 139°–142° C.

$^1$H-NMR(90 MHz, DMSO-d$_6$)δ: 1.28(t,J=7 Hz,3H), 3.36(q,J=7 Hz,2H), 7.40(dd,J=1.8 Hz,7 Hz,1H) 7.60((t,J=7 Hz,1H), 8.12(s,1H) 9.11(dd,J=1.8 Hz,7 Hz,1H), 10.12(s,1H)

(c) Preparation of 3-chloro-5-ethyl-4-methoxymethoxy-1-naphthalenecarbaldehyde

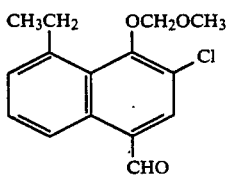

1.0 g of 3-chloro-5-ethyl-4-hydroxy-1-naphthalenecarbaldehyde, 0.91 ml of chloromethyl methyl ether and 3.5 ml of N,N-diisopropylethylamine were dissolved in 10 ml of dichloromethane, and reacted at room temperature for 4 hours. The reaction solution was concentrated under reduced pressure and the resultant residue was purified by silica gel column chromatography (5% ethyl acetate/hexane) to obtain 0.74 g of the captioned compound as a brown oily substance.

$^1$H-NMR(90 MHz, CDCl$_3$)δ:
1.27(t,J=7 Hz,3H), 3.34(q,J=7 Hz,2H), 3.60(s,3H) 5.24(s,2H), 7.20–7.64(m,2H), 7.88(s,1H), 9.02(dd,J=1.8 Hz,10.8 Hz,1H), 10.20(s,1H)

Reference 16

4-Acetoxy-3-isopropyl-5-methyl-1-naphthalenecarbaldehyde

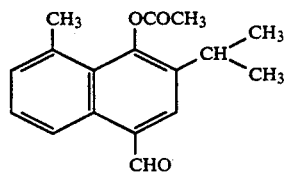

(a) Preparation of 1'-hydroxy-8'-methyl-2'-acetonaphthone

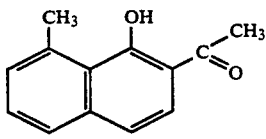

13 g of 8-methyl-1-naphthyl acetate and 13.8 g of aluminum chloride were reacted at 140° C. for 4 hours. Water, concentrated hydrochloric acid and ethyl acetate were added to the reaction mixture to dissolve all solid matters, followed by extraction with ethyl acetate. The organic phase was washed with a saturated saline solution, dried with anhydrous magnesium sulfate and concentrated under reduced pressure. The resultant residue was purified by silica gel column chromatography (7% ethyl acetate/hexane) to obtain 5.5 g of the captioned compound as a yellow oily substance.

$^1$H-NMR(90 MHz, CDCl$_3$)δ: 2.51(s,3H), 2.63(s,3H), 7.04–7.72(m,5H), 8.20(s,1H)

(b) Preparation of 1'-benzyloxy-8'-methyl-2'-acetonaphthone

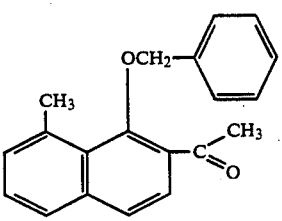

5.5 g of 1'-hydroxy-8'-methyl-2'-acetonaphthone was dissolved in 50 ml of N,N-dimethylformamide, to which 1.7 g of 60% sodium hydride was added, followed by agitation at 50° C. for 10 minutes. The reaction solution was returned to room temperature, in which 5.5 ml of benzyl chloride was dropped, followed by heating again to 70° C. for reaction for 1 hour. After returning to room temperature, water was added to the solution, which was extracted with ethyl acetate. The resultant organic phase was washed with a saturated saline solution, dried with anhydrous magnesium sulfate and concentrated under reduced pressure. The resultant reside was purified by silica gel column chromatography (15% ethyl acetate/hexane) to obtain 4.8 g of the captioned compound as a brown oily substance.

$^1$H-NMR(90 MHz, CDCl$_3$)δ: 2.52(s,3H), 2.68(s,3H), 5.08(s,2H), 7.04–8.04(m,10H)

(c) Preparation of 1-(1-benzyloxy-8-methyl-2-naphthyl)-1-methyl-1-ethanol

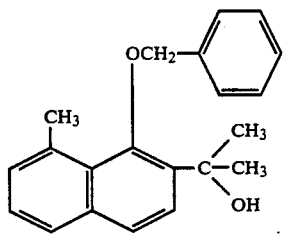

4.8 g of 1'-benzyloxy-8'-methyl-2'-acetonaphthone was dissolved in 200 ml of tetrahydrofuran and cooled down to −78° C. At the temperature, 28 ml of a tetrahydrofuran solution of 1M methylmagnesium bromide was added, followed by returning to room temperature. It was agitated at room temperature for 72 hours and was further reacted at 80° C. for 2 hours. The reaction solution was cooled down to 0° C., to which a saturated ammonium chloride aqueous solution was added portion by portion, followed by extraction with ethyl acetate. The resultant organic phase was washed with a saturated saline solution, dried with anhydrous magnesium sulfate and concentrated under reduced pressure. The residue was purified by silica gel column chromatography (10% ethyl acetate/hexane) to obtained 1.8 g of the captioned compound as a brown oily substance.

$^1$H-NMR(90 MHz, CDCl$_3$)δ: 1.61(s,3H), 1.68(s,3H), 2.48(s,3H), 5.12(s,2H), 6.74–8.14(m,10H)

(d) Preparation of 1-benzyloxy-2-isopropenyl-8methylnaphthalene

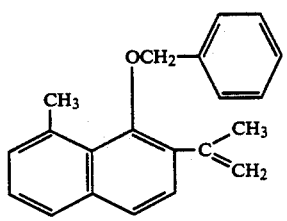

1.8 g of 1-(1-benzyloxy-8-methyl-2-naphthyl)-1-methyl-1-ethanol was dissolved in 20 ml of tetrahydrofuran, to which 30 ml of 3N hydrochloric acid was added, followed by refluxing for 2 hours. The reaction solution was returned to room temperature, to which water was added, followed by extraction with ethyl acetate. The resultant organic phase was washed with a saturated saline solution, dried with anhydrous magnesium sulfate and concentrated under reduced pressure. The residue was purified by silica gel column chromatography (4% ethyl acetate/hexane) to obtain 1.0 g of the captioned compound as a yellowish green oily substance.

$^1$H-NMR(90 MHz, CDCl$_3$)δ: 2.25(s,3H), 2.49(s,3H), 4.97(s,2H), 5.17–5.33(m,2H), 6.95–7.97(m,10H)

(e) Preparation of 2-isopropyl-8-methyl-1-naphthol

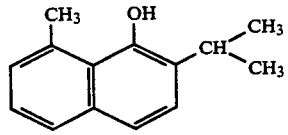

1.0 g of 1-benzyloxy-2-isopropenyl-8-methylnaphthalene and 0.1 g of 10% palladium-carbon (water content of 50%) were added to 40 ml of ethanol and hydrogenated at normal temperatures and normal pressures. The palladium-carbon was filtered through Celite, after which the filtrate was concentrated under reduced pressure to obtain 0.65 g of the captioned compound as a black oily substance.

$^1$H-NMR(90 MHz, CDCl$_3$)δ: 1.32(d,J=7 Hz,6H), 2.51(s,3H), 3.31(m,1H), 5.24(br.s,1H), 7.03–8.25(m,5H)

(f) Preparation of 3-isopropyl-4-hydroxy-5-methyl-1-naphthalenecarbaldehyde

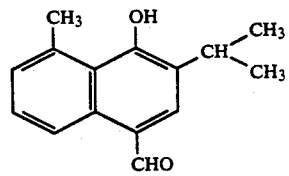

0.65 g of 2-isopropyl-8-methyl-1-naphthol was dissolved in 50 ml of dichloromethane and cooled down to 0° C. 1.3 ml of titanium tetrachloride was gradually dropped in the solution for reaction at 0° C. for 5 minutes, after which 0.9 ml of dichloromethyl methyl ether was gradually dropped and reacted at 0° C. for 1 hour. Water was added to the reaction solution, which was extracted with ethyl acetate. The resultant organic phase was washed with a saturated saline solution, dried with anhydrous magnesium sulfate and concentrated under reduced pressure. The resulting crystals were collected by filtration to obtain 0.7 g of the captioned compound as black crystals.

Melting point: 125°–128° C.

$^1$H-NMR(90 MHz, CDCl$_3$)δ: 1.38(d,J=7 Hz,6H), 2.55(s,3H), 3.36(m,1H), 7.03–7.71(m,2H), 7.71–8.03(m,2H), 9.16(m,1H), 10.38(s,1H)

(g) Preparation of 4-acetoxy-3-isopropyl-5-methyl-1-naphthalenecarbaldehyde

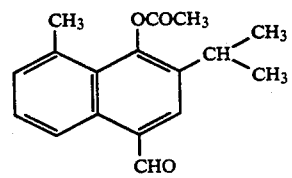

0.7 g of 3-isopropyl-4-hydroxy-5-methyl-1-naphthalenecarbaldehyde and 10 ml of acetic anhydride were dissolved in 10 ml of pyridine and reacted at room temperature for 1 hour. The reaction solution was poured into water and extracted with ethyl acetate. The organic phase was washed with dilute hydrochloric acid, a saturated sodium hydrogencarbonate aqueous solution and a saturated saline solution in this order, dried with anhydrous magnesium sulfate and concentrated under reduced pressure, thereby obtaining 0.5 g of the captioned compound as a black oily substances.

$^1$H-NMR(90 MHz, CDCl$_3$)δ: 1.32(d,J=7 Hz,6H), 2.52(s,6H), 3.18(m,1H), 6.80–7.52(m,2H), 7.84(s, 1H), 9.02(m,1H), 10.26(s,1H).

REFERENCE EXAMPLE 17

5-ethyl-4-methoxymethoxy-3-pentyloxy-1-naphthalene carbaldehyde

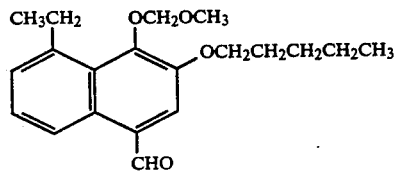

The above-captioned compound can be obtained as a yellow-brown oily product in the same procedures as those in Reference Examples 3(c) and (d) by using pentyl bromide instead of methyl iodide in Reference Example 3(b).

¹H-NMR(90 MHz, CDCl₃)δ; 0.80~1.10(m,3H), 1.14~1.62(m,7H), 1.68~2.04(m,2H), 3.38(q,J=7 Hz,2H), 3.54(s,3H), 4.14(t,J=7 Hz,2H), 5.32(s,2H), 7.18~7.50(m,2H), 7.74(s,1H), 8.90(dd,J=2.6 Hz, 7 Hz,1H), 10.44(s,1H)

REFERENCE EXAMPLE 18

5-ethyl-3-methoxyethoxy-4-methoxymethoxy-1-naphthalene carbaldehyde

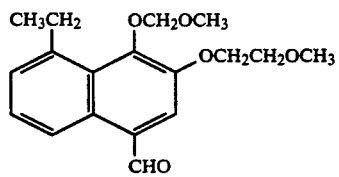

The above-captioned compound can be obtained as a yellow-brown oily product in the same procedures as those in Reference Examples 3(c) and (d) by using 2-bromoethyl methyl ether instead of methyl iodide in Reference Example 3(b).

¹H-NMR(90 MHz, CDCl₃)δ; 1.30(t,J=7 Hz,3H), 3.38(q,J=7 Hz,2H), 3.42(s,3H), 3.52(s,3H), 3.68~3.86 (m,2H), 4.16~4.34(m,2H), 5.36(s,2H), 7.20~7.52(m,2H), 7.76(s,1H), 8.92 (dd,J=2.6 Hz,7 Hz,1H), 10.32(s,1H) (dd,J=2.6 Hz,7 Hz,1H), 10.28(s,1H)

REFERENCE EXAMPLE 19

1-(t-butyldimethylsilyl)oxymethyl-5-ethyl-4-methoxymethoxy naphthalene

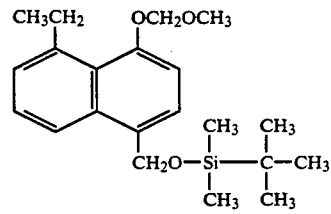

The above-captioned compound can be obtained as a yellow oily product by treating 8-ethyl-1-naphthol in the same procedures as those in Reference Example 6.

¹H-NMR(90 MHz, CDCl₃)δ; 0.12(s,6H), 0.94(s,9H), 1.32(t,J=7 Hz, 3H), 3.30(q,J=7 Hz,2H), 3.52(s,3H), 5.04(s,2H), 5.28(s,2H), 7.00(d,J=7 Hz, 1H), 7.10~7.40(m,3H), 7.72(dd,J=2.6 Hz,7 Hz)

Reference Example 20

3-benzyloxy-5-ethyl-4-methoxymethoxy-1-naphthalene carbaldehyde

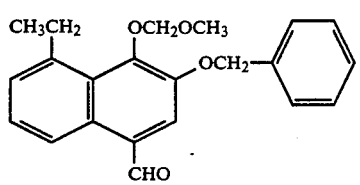

The above-captioned compound was obtained as a yellow oily product by processing 1-(t-butyldimethylsilyl)oxymethyl-5-ethyl-4-methoxymethoxy naphthalene obtained in Reference Example 19 by using benzyl bromide instead of methyl iodide.

¹H-NMR(90 MHz, CDCl₃) δ; 1.30(t,J=7 Hz,3H), 3.38(q,J=7 Hz,2H), 3.46(s,3H), 5.20(s,2H), 5.32(s,2H), 7.18~7.54(m,7H), 7.80(s,1H), 8.92 (dd,J=2.6 Hz,7 Hz,1H), 10.28(s,1H)

REFERENCE EXAMPLE 21

1-methoxymethoxy-8-(3-methoxypropyl)naphthalene (a) Synthesis of 8-methoxymethoxy-1-naphthalene carbaldehyde

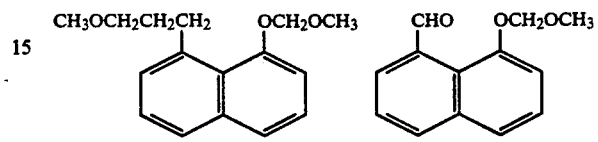

9.5 g of 8-hydroxy-1-naphthol was dissolved in 210 ml of acetone, to which 22.7 g of hydrous potassium carbonate and 5.43 ml of chloromethyl methyl ether were added and refluxed for one hour under heating. The reaction solution was filtered and the filtrate was concentrated. 12.2 g of thus obtained yellow oily product was dissolved with no further purification into 250 ml of dichloromethane, to which 4.3 g of pyridinium trifluoro acetate and 18.3 g of pyridinium dichromate were added and stirred at a room temperature for 12 hours. After filtering off insoluble matters, the filtrate was concentrated and then purified on silica gel column chromatography (10% ethyl acetatemexane), to obtain in 5.1 g of the above-captioned compound as colorness crystals.

m.p.; 56°~57° C.

¹H-NMR(90 MHz, CDCl₃)δ; 3.50(s,3H), 5.35(s,2H), 7.16~8.00(m,6H), 11.11(s,1H)

(b) Synthesis of ethyl 3-(8-methoxymethoxy-1-naphthyl) propenoate

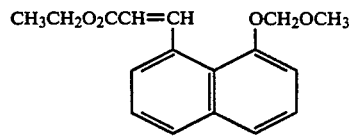

A liquid suspension of 1.36 g of 60% sodium hydride in 50 ml of 1,2-dimethoxyethane was incorporated with 7.63 g of triethylphosphono acetate under ice cooling and stirred for 5 min. A solution of 4.9 g of 8-methoxymethoxy-1-naphthalene carbaldehyde in 30 ml of 1,2-dimethoxy ethane was dropped to the resultant clear solution and stirred for 10 min. After the reaction was over, water was added and extracted with ethyl acetate, the organic layer was washed with a saturated aqueous solution of sodium chloride and then dried over anhydrous magnesium sulfate. When the residue obtained by distilling off the solvent was purified on silica gel column chromatography (10% ethyl acetate-hexane), 6.4 g of the above-captioned compound was obtained as pale brown oily product.

¹H-NMR(90 MHz, CDCl₃)δ; 1.36(t,J=7 Hz,3H), 3.54(s,3H), 4.28(q,J=7 Hz,2H), 5.32(s,2H), 6.14(d,J=15 Hz,1H), 7.08~7.87(m, 6H), 8.93(d,J=15 Hz,1H)

(c) Synthesis of 8-(3-hydroxypropyl)-2-methoxymethoxy naphthalene

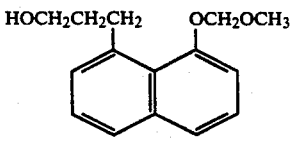

6.4 g of ethyl 2-(8-methoxymethoxy)propenoate was dissolved in 60 ml of tetrahydrofuran, to which 0.6 g of 10% palladium carbon (50% hydrous product) and hydrogenated at normal temperature and normal pressure for 4 hours. After the reaction was over, palladium carbon was removed by filtration and the filtrate was concentrated. The resultant colorless oily product was dissolved in 20 liter of tetrahydrofuran and dropped under ice cooling to 0.62 g of aluminum lithium hydride previously suspended in 20 ml of tetrahydrofuran. After stirring at a room temperature for one hour after dropping, it was cooled again with ice and water and 1N-hydrochloric acid was added. The reaction solution was extracted with ethyl acetate, washed with saturated aqueous solution of sodium chloride and then dried over anhydrous magnesium sulfate. When the residue obtained by distilling off the solvent was purified on silica gel column chromatography (30% ethyl acetate-hexane), 5.2 g of the above-captioned compound was obtained as a colorless oily product.

$^1$H-NMR(90 MHz, CDCl$_3$)δ; 1.51(br,s,1H), 1.82~2.15(m,2H), 3.37(m,2H), 3.56(s,3H), 3.72(t,J=7 Hz,2H), 5.34(s,2H), 7.03~7.72(m,6H)

(d) 2-methoxymethoxy-8-(3-methoxypropyl) naphthalene

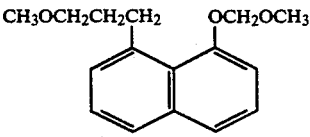

5.1 g of 8-(3-hydroxypropyl)-1-methoxymethoxy naphthalene was dissolved in 40 ml of N,N-dimethyl formamide, to which 1.4 g of 55% sodium hydride was added under ice cooling. Then, 1.93 ml of methyl iodide was added and stirred at a room temperature for 2 hours. After adding water to the reaction solution and extracting with ethyl acetate, the organic layer was washed with water and then with a saturated aqueous solution of sodium chloride successively and then dried over magnesium sulfate. After distilling off the solvent, when it was purified on silica gel column chromatography (10% ethyl acetate-hexane), 5.3 g of the above-captioned compound was obtained as a colorless oily product.

$^1$H-NMR(90 MHz, CDCl$_3$)δ; 1.89~2.13(m,2H), 3.22~3.54(m,4H), 3.35(s,3H), 3.54(s,3H), 5.34(s,2H), 7.04~7.72(m,6H)

REFERENCE EXAMPLE 22

3-methoxy-4-methoxymethoxy-5-(3-methoxypropyl) naphthalene carbaldehyde

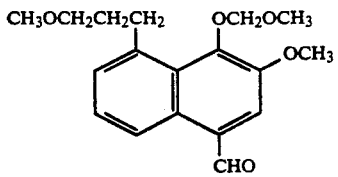

The above-captioned compound was obtained as a pale yellow oily product from 1-methoxymethoxy-8-(3-methoxypropyl)naphthalene by the same procedures as those in Reference Example 3.

$^1$H-NMR(90 MHz, CDCl$_3$)δ; 1.85~2.11(m,2H), 3.28~3.57(m,4H), 3.34(s,3H), 3.55(s,3H), 4.02(s,3H), 5.34(s,2H), 7.30~7.54(m,2H), 7.82(s,1H), 8.98(dd,J=2.6 Hz,7 Hz, 1H), 10.44(s,1H)

REFERENCE EXAMPLE 23

5-ethyl-1-methoxymethoxy naphthalene (a) Synthesis of 5-bromo-1-methoxymethoxy naphthalene

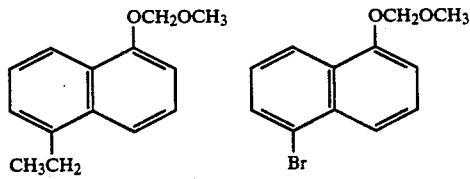

6.0 g of 5-bromo-1-naphthol was dissolved in 50 ml of N,N-dimethylformamide, to which 1.2 g of 60% sodium hydride was added. After stirring at a room temperature for 10 min, it was cooled to 0° C., to which 3.5 ml of chloromethyl methyl ether was added and stirred for 10 min. Water was added to the reaction solution, which was extracted with ethyl acetate. The extract was washed with a saturated aqueous solution of sodium chloride, dried over anhydrous magnesium sulfate and then the solvent was distilled off. When the resultant residue was purified on silica gel column chromatography (10% ethyl acetate/hexane), 7.2 g of the above-captioned compound was obtained as red acicular crystals.

m.p.: 49°-50° C.

$^1$H-NMR(90 MHz, CDCl$_3$)δ; 3.51(s,3H), 5.34(s,2H), 7.09(br,d,J=7 Hz,1H), 7.20~7.36(m,1H), 7.42(t,J=7 Hz,1H), 7.73(br.d,J=7 Hz,1H), 7.78(t,J=7 Hz,1H), 8.21(br.d,J=7 Hz,1H)

(b) Synthesis of 5-ethyl-1-methoxymethoxy naphthalene

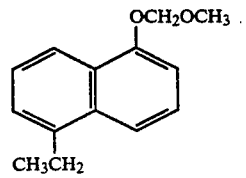

6.9 g of 5-bromo-1-methoxymethoxy naphthalene was dissolved in 100 ml of anhydrous tetrahydrofuran and cooled to −60° C. 21.3 ml of a hexane solution containing 1.6M of n-butyl lithium was gradually added to the solution. After stirring at −40° C.−−60° C. for one hour, the reaction solution was cooled to −65° C. and 4.2 ml of ethyl iodide was slowly dropped. After the dropping, the temperature was warmed upto the room temperature, water was added and the solution was extracted with ethyl acetate. After washing the extract with an aqueous saturated solution of sodium chloride and drying over anhydrous magnesium sulfate, the solvent was distilled off. When the residue was purified on silica gel column chromatography (7% ethyl acetate/hexane), 5.5 g of the above-captioned compound was obtained as a pale yellow oily product.

¹H-NMR(90 MHz, CDCl₃)δ; 1.35(t,J=7 Hz,3H), 3.06(q,J=7 Hz,2H), 3.51(s,3H), 5.33(s,2H), 6.92~7.08(m,1H), 7.11~7.47(m,3H), 7.51~7.61(m,1H), 7.92~8.40(m,1H)

REFERENCE EXAMPLE 24

7-ethyl-3-methoxy-4-methoxymethoxy-1-naphthalene carbaldehyde

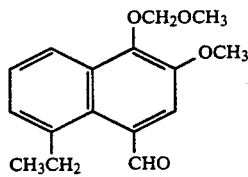

When 5-ethyl-1-methoxymethoxy naphthalene was treated in the same procedures as those in Reference Example 3, the above-captioned compound was obtained as a colorless oily product.

¹H-NMR(90 MHz, CDCl₃)δ; 1.38(t,J=7 Hz,3H), 3.08(q,J=7 Hz,2H), 3.58(s,3H), 3.93(s,3H), 5.36(s,2H), 7.30~7.58(m,2H), 7.82(s,1H), 8.17(dd,J=3.6 Hz,7 Hz,1H), 10.75(s,1H)

REFERENCE EXAMPLE 25

7-ethyl-3-methoxy-4-methoxymethoxy-1-naphthalane carbaldehyde

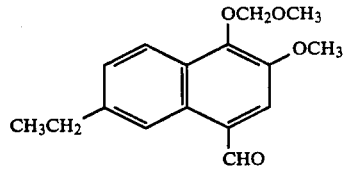

(a) Synthesis of 6-ethyl-2-methoxy-naphthol

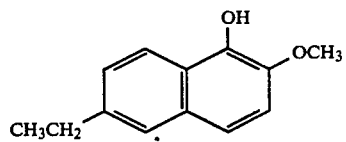

4.4 g of 6-ethyl-3-methoxy-1-naphthalene carbaldehyde and 4.9 g of 80-85% m-chloroperbenzoic acid were dissolved in 40 ml of dichloromethane and then refluxed under heating for 30 min. The solution was cooled to 0° C. and after adding an aqueous saturated solution of sodium thiosulfate and stirring for 20 min, insoluble matters were removed by filtration and then the filtrate was extracted with ethyl acetate. The extract was washed with a saturated aqueous solution of sodium chloride and then dried over anhydrous magnesium sulfate.

7.0 g of a brown oily product obtained by distilling off the solvent was dissolved into 20 ml of methanol with no further purification. Then, an aqueous solution of potassium hydroxide (potassium hydroxide 2.0 g/water 10 ml) was added and refluxed under heating for 30 min. The reaction solution was cooled to 0° C., rendered acidic with addition of diluted hydrochloric acid, and extracted with ethyl acetate. After washing the extract with an aqueous saturated solution of sodium chloride, it was dried over anhydrous magnesium sulfate. When the residue obtained by distilling off the solvent was purified on silica gel column chromatography (10% ethyl acetate/hexane), 3.3 g of the above-captioned compound was obtained as pale brown plate-like crystals.

m.p.: 68°-69° C.

¹H-NMR(90 MHz, CDCl₃)δ; 1.31(t,J=7 Hz,3H), 2.77(q,J=7 Hz,2H), 3.96(s,3H), 6.97(br,s,1H), 7.08~7.40(m,3H), 7.49(br.s,1H), 8.06(d,J=7 Hz,1H)

(b) 7-ethyl-hydroxy-3-methoxy-1-naphthalene carbaldehyde

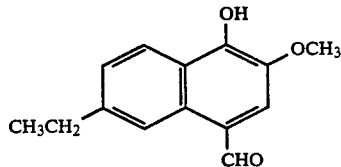

3.3 g of 6-ethyl-2-methoxy-1-naphthol was dissolved in 25 ml of dichloromethane and cooled to 0° C. 3.65 ml of titanium tetrachloride and 2.4 ml of dichloromethyl methyl ether were added successively at that temperature and stirred for 10 min. After the reaction was over, water was added and the solution was extracted with ethyl acetate. After washing the extract with an aqueous saturated solution of sodium chloride, it was dried over anhydrous magnesium sulfate. When the solvent was distilled off and deposited crystals were washed with isopropyl ether, 2.5 g of the above-captioned compound was obtained as brown crystals.

m.p.: 114°-116° C.

¹H-NMR(90 MHz, CDCl₃)δ; 1.34(t,J=7 Hz,3H), 2.83(q,J=7 Hz,2H), 3.04(s,3H), 6.59(s,1H), 7.36(dd,J=3 Hz, 9 Hz,1H), 7.79(s,1H), 8.11(d,J=9 Hz,1H), 8.83(m,1H), 10.35(s,1H)

(c) Synthesis of 7-ethyl-3-methoxy-4-methoxymethoxy 1-naphthalene carbaldehyde

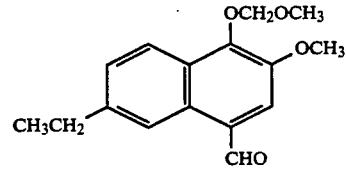

2.5 g of 7-ethyl-4-hydroxy-3-methoxy-1-naphtalane carbaldehyde was dissolved in 20 ml of N,N-dimethylformamide, to which 0.52 g of 60% sodium hydride was added and stirred for 10 min. The reaction solution was cooled to 0° C., to which 1.3 ml of chloromethyl methyl ether was slowly dropped. After stirring for 10 min at a room temperature, water was added and the solution was extracted with ethyl acetate. After washing the extract with a saturated aqueous solution of sodium chloride, it was dried over anhydrous magnesium sulfate. When the residue obtained by distilling off the solvent on silica gel chromatography (10% ethyl acetate/hexane), 2.8 g of the above-captioned compound was obtained as a yellow oily product.

$^1$H-NMR(90 MHz, CDCl$_3$)δ; 1.32(t,J=7 Hz,3H), 3.82(q,J=7 Hz,2H), 3.57(s,3H), 3.96(s,3H), 5.38(s,2H), 7.38(dd,J=3 Hz,9 Hz,1H), 7.71(s,1H), 8.15(d,J=9 Hz,1H), 8.82(m,1H), 10.37(s,1H)

EXAMPLE 1

(E)-3-(5-ethyl-4-hydroxy-3-methoxy-1-naphthyl)-2-methylpropenoic acid

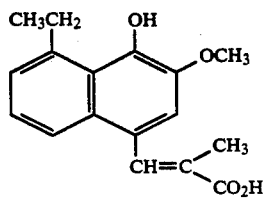

(a) Preparation of ethyl (E)-3-(5-ethyl-3-methoxy-4-methoxymethoxy-1-naphthyl)-2-methylpropenoate

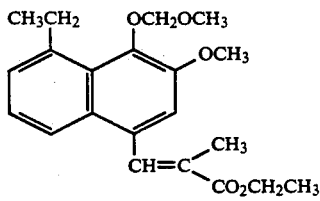

36 g of 60% sodium hydride was suspended in 500 ml of N,N-dimethylformamide and 268 g of triethyl 2-phosphonopropionate was added at ice bath temperature. After stirring at room temperature for 1 hour, a solution of 206 g of 5-ethyl-3-methoxy-4-methoxymethoxy-1-naphthalenecarbaldehyde was added. After stirring at room temperature for 15 minutes, ice cooled water was gradually added at ice bath temperature. The mixture was extracted with ethyl acetate and the combined organic layer was washed with brine. After drying over anhydrous magnesium sulfate, the solvent was evaporated and the residue was purified by silica gel column chromatography (10% ethyl acetate/hexane) to obtain 262.4 g of the titled compound as a yellow oil (containing a small amount of Z isomer).

$^1$H-NMR(90 MHz, CDCl$_3$)δ: 1.30(t,J=7 Hz,3H), 1.38(t,J=7 Hz,3H), 1.96(d,J=1.3 Hz,3H), 3.34(q,J=7 Hz,2H), 3.57(s,3H), 3.91(s,3H), 4.28(q,J=7 Hz,2H), 5.17(s,2H), 7.04–7.31(m,3H), 7.60(m,1H), 8.03(br.s,1H).

(b) (E)-3-(5-ethyl-3-methoxy-4-methoxymethoxy-1-naphthyl)-2-methylpropenoic acid

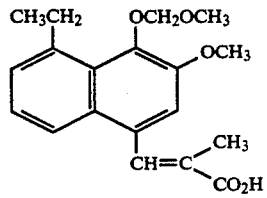

28 g of ethyl (E)-3-(5-ethyl-3-methoxy-4-methoxymethoxy-1-naphthyl)-2-methylpropenoate was dissolved in 240 ml of ethanol and a potassium hydroxide aqueous solution (potassium hydroxide 28 g/water 55 ml) was added, followed by refluxing for 1 hour. 280 ml of 2N hydrochloric acid was added to the reaction mixture at ice bath temperature to make it acidic, followed by extraction with ethyl acetate. The organic layer was washed with brine, dried over anhydrous magnesium sulfate, and evaporated. Diisopropyl ether was added to the resultant residue and the resultant crystals were filtered to obtain 23 g of the titled compound as pale yellow crystals.

Melting point: 127°–128° C.

$^1$H-NMR(90 MHZ,CDCl$_3$)δ:
1.28(t,J=7 Hz,3H), 2.00(d,J=1.8 Hz,3H), 3.35(q,J=7 Hz,2H), 3.56(s,3H), 3.93(s,3H), 5.19(s,2H), 7.17–7.29(m,3H), 7.61–7.71(m,1H), 8.26(s,1H).

(c) (E)-3-(5-ethyl-4-hydroxy-3-methoxy-1-naphthyl)-2-methylpropenoic acid

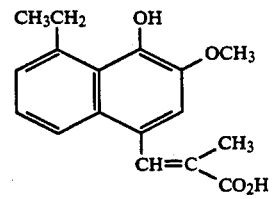

23 g of (E)-3-(5-ethyl-3-methoxy-4-methoxymethoxy-1-naphthyl)-2-methylpropenoic acid was dissolved in 230 ml of acetone and 15 ml of concentrated hydrochloric acid was added slowly at room temperature. After stirring at room temperature for 1.5 hours, the reaction mixture was gradually poured into 3.5 liters of water. The resultant crystals were filtered, washed with water and dried to obtain 19 g of the titled compound as pale yellow crystals.

Melting point: 194°–195° C.

$^1$H-NMR(90 MHz, CDCl$_3$)δ: 1.33(t,J=7 Hz,3H), 2.04(d,J=1.3 Hz,3H), 3.34(q,J=7 Hz,2H), 3.97(s,3H), 6.47(s,1H), 7.12–7.35(m,3H), 7.52–7.75(m,1H), 8.27(s,1H).

EXAMPLE 2

(Z)-3-(5-ethyl-4-hydroxy-3-methoxy-1-naphthyl)-2-methylpropenoic acid

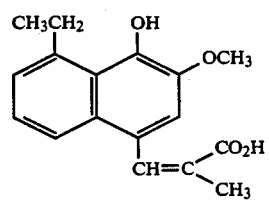

(a) Ethyl (Z)-3-(5-ethyl-3-methoxy-4-methoxymethoxy-1-naphthyl)-2-methylpropenoate

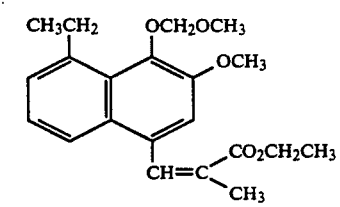

15.6 g of ethyl (E)-3-(5-ethyl-3-methoxy-4-methoxymethoxy-1-naphthyl)-2-methylpropenoate was dissolved in 300 ml of acetone and irradiated for 2 hours with light from a high pressure mercury lamp through a Pyrex filter. The solvent was evaporated and the resultant residue was purified by silica gel column chromatography (3% ethyl acetate/hexane) to obtain 6.6 g of the titled compound as a yellow oil. At the same time, 9.0 g of a mixture of E and Z isomers was obtained.

$^1$H-NMR(90 MHz, CDCl$_3$)δ: 0.75(t,J=7 Hz,3H), 1.28(t,J=7 Hz,3H), 2.19(d,J=1.8 Hz,3H), 3.34(q,J=7 Hz,2H), 3.57(s,3H), 3.83(q,J=7 Hz,2H), 3.89(s,3H), 5.13(s,2H), 7.01-7.31(m,4H), 7.53-7.74(m,1H).

(b) Preparation of (Z)-3-(5-ethyl-3-methoxy-4-methoxymethoxy-1-naphthyl)-2-methylpropenoic acid

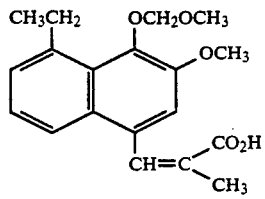

71.2 g of ethyl (Z)-3-(5-ethyl-3-methoxy-4-methoxymethoxy-1-naphthyl)-2-methylpropenoate was dissolved in 600 ml of ethanol and a potassium hydroxide aqueous solution (potassium hydroxide 71 g/water 140 ml) was added, followed by refluxing for 1 hour. The reaction mixture was cooled on an ice bath, after which 700 ml of 2N hydrochloric acid was added to make it acidic, followed by extraction with ethyl acetate. The organic layer was washed with brine, dried over anhydrous magnesium sulfate. The solvent was evaporated to obtain 66 g of the titled compound as a yellow oil.

$^1$H-NMR(90 MHz, CDCl$_3$)δ: 1.24(t,J=7 Hz,3H), 2.16(d,J=1.8 Hz,3H), 3.32(q,J=7 Hz,2H), 3.52(s,3H), 3.81(s,3H), 5.15(s,2H), 7.08-7.32(m,4H), 7.44-7.68(m,1H).

(c) Preparation of (Z)-3-(5-ethyl-4-hydroxy-3-methoxy-1-naphthyl)-2-methylpropenoic acid

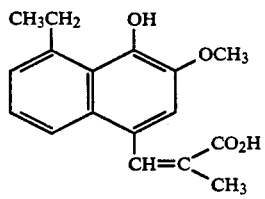

66 g of (Z)-3-(5-ethyl-3-methoxy-4-methoxymethoxy-1-naphthyl)-2-methylpropenoic acid was dissolved in 700 ml of acetone in which nitrogen has been preliminarily bubbled, and 43 ml of concentrated hydrochloric acid was gradually added while stirring at room temperature in a stream of nitrogen under light-shielded conditions. After stirring at room temperature for 1.5 hours, the reaction mixture was gradually poured into water to crystalize. The crystals were filtered, washed with water and dried to obtain 50.0 g of the titled compound as yellow crystals.

Melting point: 190°-191° C.

$^1$H-NMR(90 MHz, CDCl$_3$)δ: 1.31(t,J=7 Hz,3H), 2.16(d,J=1.5 Hz,3H), 3.31(q,J=7 Hz,2H), 3.76(s,3H), 6.34(br.s,1H), 7.04-7.32(m,4H), 7.42-7.64(m,1H).

EXAMPLES 3-8

The 5-ethyl-3-methoxy-4-methoxymethoxy-1-naphthalenecarbaldehyde and suitable Witting reagents were reacted, followed by treatment in the same manner as in Examples 1 and 2 to obtain compounds of Examples 3 to 8 indicated in Table 2.

TABLE 2

| No. | NMR data | (90 MHz) |
|---|---|---|
| 3 | 1.32(t, J=7Hz, 3H), 3.34(q, J=7Hz, 2H), 4.02(s, 3H), 6.36(d, J=15Hz, 1H), 6.86(br.s, 1H), 7.08~7.36(m, 2H), 7.50(s, 1H), 7.92(dd, J=2.6Hz, 7.7Hz, 1H), 8.46(d, J=15Hz, 1H) | (CDCL$_3$-DMSO-d$_6$) |
| 4 | 1.06(t, J=7Hz, 3H), 1.15(t, J=7Hz, 3H), 2.16~2.50(m, 2H), 3.10~3.45(m, 2H), 3.90(s, 3H), 7.08~7.64(m, 4H), 7.91(s, 1H), 9.12(s, 1H), 12.51(br.s, 1H) | (DMSO-d$_6$) |
| 5 | 1.16(t, J=7Hz, 3H), 1.25(t, J=7Hz, 3H), 2.28~2.60(m, 2H), 3.08~3.48(m, 2H), 3.83(s, 3H), 7.01(m, 1H), 7.04~7.32(m, 2H), 7.63(m, 1H), 8.89(s, 1H), 12.35(m, 1H) | (DMSO-d$_6$) |
| 6 | 1.22(t, J=7Hz, 3H), 3.13~3.40(m, 2H), 3.31(s, 3H), 6.74(s, 1H), 7.04~7.39(m, 7H), 7.83(m, 1H), 8.32(s, 1H), 9.18(s, 1H), 12.69(m, 1H) | (DMSO-d$_6$) |
| 7 | 1.30(t, J=7Hz, 3H), 3.32(q, J=7Hz, 2H), 3.50(s, 3H), 3.86(s, 2H), 6.40(br.s, 1H), 7.00~7.40(m, 8H), 7.68(dd, J=2.6Hz, 7.7Hz, 1H), 8.50(s, 1H) | (CDCl$_3$) |
| 8 | 1.30(t, J=7Hz, 3H), 3.30(q, J=7Hz, 2H), 3.72(s, 3H), 3.80(s, 2H), 6.36(br.s, 1H), 7.0~7.58(m, 10H) | (CDCl$_3$) |

| Example No. | Intended Compounds Structural Formula Name of Compound | Appearance | NMR Spectrum (90 MHz) | Melting Point (°C.) |
|---|---|---|---|---|
| 3 | (E)-3-(5-ethyl-4-hydroxy-3-methoxy-1-naphthyl)propenoic acid | yellow crystals | | over 185 (decomposed) |
| 4 | (E)-2-ethyl-3-(5-ethyl-4-hydroxy-3-methoxy-1-naphthyl)-propenoic acid | pale yellow crystals | | 171-173 |
| 5 | (Z)-2-ethyl-3-(5-ethyl-4-hydroxy-3-methoxy-1-naphthyl)propenoic acid | yellow crystals | | 134-136 |
| 6 | (E)-3-(5-ethyl-4-hydroxy-3-methoxy-1-naphthyl)-2-phenylpropenoic acid | yellow crystals | | 180-181 |
| 7 | (E)-2-benzyl-3-(5-ethyl-4-hydroxy-3-methoxy-1-naphthyl)propenoic acid | pale yellow crystals | | 174-176 |
| 8 | (Z)-2-benzyl-3-(5-ethyl-4-hydroxy-3-methoxy-1-naphthyl)propenoic acid | yellow crystals | | 129-131 |

(formulae of the example compounds)

TABLE 2-continued

| | |
|---|---|
| 4 | 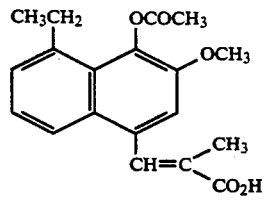 |
| 5 | (structure: CH₃CH₂, OH, OCH₃ naphthyl with CH=C(CO₂H)(CH₂CH₃)) |
| 6 | (structure: CH₃CH₂, OH, OCH₃ naphthyl with CH=C(C₆H₅)(CO₂H)) |
| 7 | (structure: CH₃CH₂, OH, OCH₃ naphthyl with CH=C(CH₂C₆H₅)(CO₂H)) |
| 8 | (structure: CH₃CH₂, OH, OCH₃ naphthyl with CH=C(CO₂H)(CH₂C₆H₅)) |

EXAMPLE 9

(Z)-3-(4-acetoxy-5-ethyl-3-methoxy-1-naphthyl)-2-methylpropenoic acid

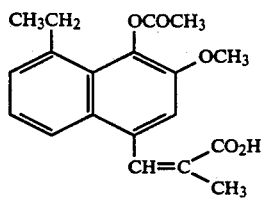

(a) Preparation of (E)-3-(4-acetoxy-5-ethyl-3-methoxy-1-naphthyl)-2-methylpropenoic acid 440 mg of (E)-3-(5-ethyl-4-hydroxy-3-methoxy-1-naphthyl)-2-methylpropenoic acid was dissolved in 2.4 ml of pyridine and 0.42 ml of acetic anhydride was added, followed by stirring at room temperature for 1 hour. The reaction mixture was poured into water and extracted with ethyl acetate. The organic layer was washed with dilute hydrochloric acid and water in this order, dried over anhydrous magnesium sulfate and concentrated in vacuo. The resultant crystals were washed with hexane to obtain 390 mg of the titled compound as colorless crystals.

Melting point: 195°-196° C.

¹H-NMR(90 MHz, CDCl₃)δ: 1.34(t,J=7 Hz,3H), 2.01(d,J=1.5 Hz,3H), 2.41(s,3H), 3.12(q,J=7 Hz,2H), 3.91(s,3H), 7.14-7.36(m,3H), 7.56-7.73(m,1H), 8.22(m,1H).

(b) Preparation of (Z)-3-(4-acetoxy-5-ethyl-3-methoxy-1-naphthyl)-2-methylpropenoic acid

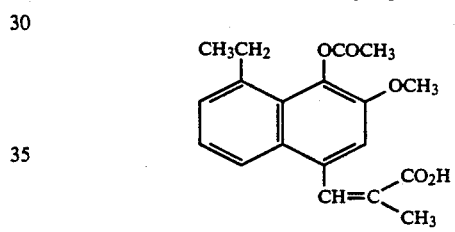

1.15 g of (E)-3-(4-acetoxy-5-ethyl-3-methoxy-1-naphthyl)-2-methylpropenoic acid was dissolved in 200 ml of acetone and irradiated with light from a high pressure mercury lamp through a Pyrex filter at room temperature for 3 hours. The reaction mixture was concentrated in vacuo and purified by silica gel column chromatography (3% methanol/chloroform) to obtain 470 mg of the titled compound as colorless crystals.

Melting point: 148°-150° C.

¹H-NMR(90 MHz, CDCl₃)δ: 1.31(t,J=7 Hz,3H), 2.16(d,J=1.5 Hz,3H), 2.39(s,3H), 3.08(q,J=7 Hz,2H), 3.80(s,3H), 7.08-7.32(m,4H), 7.50-7.69(m,1H), 8.60(br.s,1H).

EXAMPLE 10

(E)-3-(4-hydroxy-3-methoxy-5-propyl-1-naphthyl)-2-methylpropenoic acid

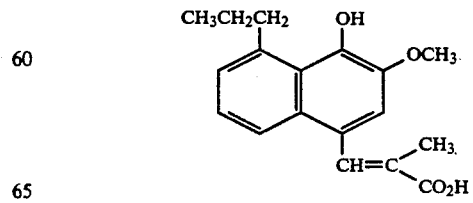

(a) Preparation of ethyl (E)-3-(3-methoxy-4-methoxymethoxy-5-propyl-1-naphthyl)-2-methylpropenoate

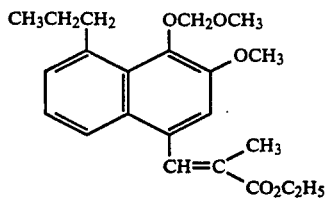

45 g of 60% sodium hydride was suspended in 650 ml of N,N-dimethylformamide and cooled to 10° C. 355 g of triethyl 2-phosphonopropionate was added to the solution to make a clear solution. A solution of 270 g of 3-methoxy-4-methoxymethoxy-5-propyl-1-naphthalenecarbaldehyde in N,N-dimethylformamide (250 ml) was dropped in the solution and stirred at room temperature for 1 hour. The reaction mixture was poured into brine and extracted with ethyl acetate. The organic layer was washed with brine, dried over anhydrous magnesium sulfate and concentrated in vacuo. The residue was purified by silica gel column chromatography (8% ethyl acetate/hexane) to obtain 325.3 g of the titled compound as a pale yellow oil (containing a small amount of Z isomer).

$^1$H-NMR(90MHz, CDCl$_3$)δ: 0.98(t,J=7 Hz,3H), 1.38(t,J=7 Hz,3H), 1.44–1.92(m,2H), 1.96(d,J=1.8 Hz,3H), 3.12–3.38(m,2H), 3.58(s,3H), 3.92(s,3H), 4.29(q,J=7 Hz,2H), 5.16(s,2H), 7.04–7.32(m,2H), 7.24(s,1H), 7.48–7.72(m,1H), 8.04(br.s,1H).

(b) Preparation of (E)-3-(3-methoxy-4-methoxymethoxy-5-propyl-1-napthyl)-2-methylpropenoic acid

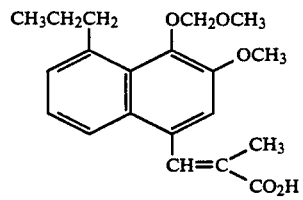

2.2 g of ethyl (E)-3-(3-methoxy-4-methoxymethoxy-5-propyl-1-naphthyl)-2-methylpropenoate was dissolved in 50 ml of ethanol. A sodium hydroxide aqueous solution (sodium hydroxide 1.4 g/water 50 ml) was added, followed by stirring at 60° C. for 30 minutes. After cooling to room temperature, dilute hydrochloric acid was added to make the reaction mixture acidic, and extracted with ethyl acetate. The organic layer was washed with brine, dried over anhydrous magnesium sulfate and concentrated in vacuo. The resultant crystals were filtered to obtain 1.9 g of the titled compound as pale yellow crystals.

Melting point: 128°–129° C.

$^1$H-NMR(90 MHz, CDCl$_3$)δ: 0.98(t,J=7 Hz,3H), 1.44–1.92(m,2H), 2.02(d,J=1.8 Hz,3H), 3.08–3.40(m,2H), 3.58(s,3H), 3.94(s,2H), 5.18(s,2H), 7.04–7.36(m,3H), 7.48–7.72(m,1H), 8.00(br.s,1H), 8.22(br.s,1H).

(c) Preparation of (E)-3-(4-hydroxy-3-methoxy-5-propyl-1-naphthyl)-2-methylpropenoic acid 1.9 g of (E)-3-(3-methoxy-4-methoxymethoxy-5-propyl-1-naphthyl)-2-methylpropenoic acid was dissolved in 80 ml of acetone and 40 ml of water and 3 ml of concentrated hydrochloric acid was added, followed by stirring at 50° C. for 2 hours. After cooling to room temperature the reaction mixture was poured into water, and the resultant crystals were filtered and washed with hexane. 1.5 g of the titled compound was obtained as pale yellow crystals.

Melting point: 170°–172° C.

$^1$H-NMR(90 MHz, DMSO-d$_6$)δ: 0.94(t,J=7 Hz,3H), 1.66(m,2H), 1.94(br.s,3H), 2.98–3.50(m,2H), 3.90(s,3H), 7.02–7.78(m,4H), 8.00(br.s,1H), 9.14(br.s,1H), 12.45(br.s,1H).

EXAMPLE 11

(Z)-3-(4-hydroxy-3-methoxy-5-propyl-1-naphthyl)-2-methylpropenoic acid

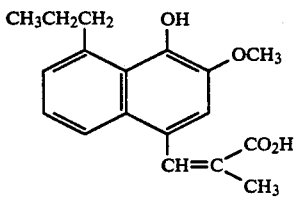

(a) Preparation of ethyl (Z)-3-(3-methoxy-4-methoxymethoxy-5-propyl-1-naphthyl)-2-methylpropenoate

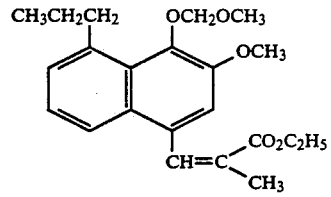

196.5 g of ethyl (E)-3-(3-methoxy-4-methoxymethoxy-5-propyl-1-naphthyl)-2-methylpropenoate was dissolved in 2.6 liters of acetone and irradiated with light from a high pressure mercury lamp through a Pyrex filter for 2.5 hours. The reaction mixture was concentrated in vacuo and purified by silica gel column chromatography (3% ethyl acetate/hexane) to obtain 59.2 g of the titled compound as a pale yellow oil. At the same time, 136.4 g of a mixture of the E and Z isomers was recovered.

$^1$H-NMR(90 MHz, CDCl$_3$)δ: 0.74(t,J=7 Hz,3H), 0.96(t,J=7 Hz,3H), 1.42–1.90(m,2H), 2.18(d,J=1.8 Hz,3H), 3.10–3.38(m,2H), 3.56(s,3H), 3.82(q,J=7 Hz,2H), 3.90(s,3H), 5.12(s,2H), 6.98–7.28(m,3H), 7.20(s,1H), 7.50–7.72(m,1H).

(b) Preparation of (Z)-3-(3-methoxy-4-methoxymethoxy-5-propyl-1-naphthyl)-2-methylpropenoic acid

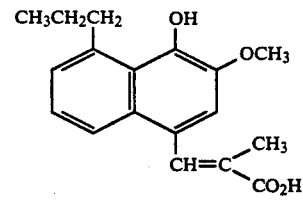

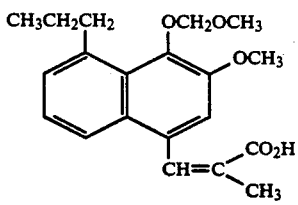

170 g of ethyl (Z)-3-(3-methoxy-4-methoxymethoxy-5-propyl-1-naphthyl)-2-methylpropenoate was dissolved in 850 ml of ethanol and a potassium hydroxide aqueous solution (potassium hydroxide 60 g/water 120 ml) was added, followed by refluxing for 1 hour. After cooling to 10° C., 2.5N hydrochloric acid was added to make it pH~5, followed by extraction with ethyl acetate. The organic layer was washed with brine, dried over anhydrous magnesium sulfate and concentrated in vacuo. The resultant crystals were filtered to obtain 151 g of the titled compound as yellow crystals.

Melting point: 67°–68° C.

$^1$H-NMR(90 MHz, CDCl$_3$)δ: 0.96(t,J=7 Hz,3H), 1.40–1.90(m,2H), 2.16(d,J=1.8 Hz,3H), 3.08–3.36(m,2H), 3.52(s,3H), 3.80(s,3H), 5.12(s,2H), 7.00–7.36(m,3H), 7.20(s,1H), 7.40–7.68(m,1H).

(c) Preparation of (Z)-3-(4-hydroxy-3-methoxy-5-propyl-1-naphthyl)-2-methylpropenoic acid

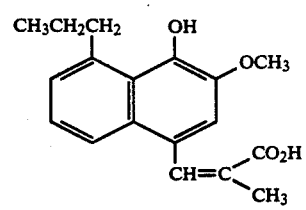

2.2 g of (Z)-3-(3-methoxy-4-methoxymethoxy-5-propyl-1-naphthyl)-2-methylpropenoic acid was dissolved in 40 ml of acetone, to which 2.5 ml of concentrated hydrochloric acid was added under light-shielding conditions, followed by stirring in a stream of nitrogen at room temperature for 2 hours. The reaction mixture was poured into water, and the resultant crystals were filtered, washed with hexane and dried in vacuo to obtain 1.7 g of the titled compound as yellow crystals.

Melting point: 170°–172° C.

$^1$H-NMR(90 MHz, CDCl$_3$)δ: 0.98(t,J=7 Hz,3H), 1.42–1.94(m,2H), 2.18(d,J=1.8 Hz,3H), 3.08–3.34(m,2H), 3.90(s,3H), 4.68(br.s,1H), 6.98–7.30(m,4H), 7.62(dd,J=1.8 Hz,7 Hz,1H).

EXAMPLES 12–15

The 3-methoxy-4-methoxymethoxy-5-propyl-1-naphthalenecarbaldehyde obtained in Reference 4 and suitable Witting reagents were reacted, followed by treatment in the same manner as in Examples 10 and 11 to obtain compounds of Examples 12 to 15 indicated in Table 3.

TABLE 3

| Example No. | Structural Formula Name of Compound | Appearance | NMR Spectrum (90 MHz) | Melting Point (°C.) |
|---|---|---|---|---|
| 12 | (E)-3-(4-hydroxy-3-methoxy-5-propyl-1-naphthyl)-propenoic acid | yellow crystals | | 187–189 |
| 13 | (E)-2-ethyl-3-(4-hydroxy-3-methoxy-5-propyl-1-naphthyl)propenoic acid | pale yellow crystals | | 175–176 |
| 14 | (Z)-2-ethyl-3-(4-hydroxy-3-methoxy-5-propyl-1-naphthyl)propenoic acid | pale yellow crystals | | 134–136 |
| 15 | (Z)-2-benzyl-3-(4-hydroxy-3-methoxy-5-propyl-1-naphthyl)propenoic acid | yellow crystals | | 104–106 |

| No. | chemical formula | NMR data | (90 MHz) |
|---|---|---|---|
| 12 | (structure: 8-propyl-1-hydroxy-2-methoxy-naphthyl with CH=CH-CO$_2$H) | 0.94(t, J=7Hz, 3H), 1.36~1.88(m, 2H), 3.00~3.40(m, 2H), 3.95(s, 3H), 6.49(d, J=15Hz, 1H), 6.92~7.36(m, 2H), 7.64~7.96(m, 2H), 8.26(d, J=15Hz, 1H), 9.46(br.s, 1H), 12.27(br.s, 1H) | (DMSO-d$_6$) |
| 13 | (structure: 8-propyl-1-hydroxy-2-methoxy-naphthyl with CH=C(CH$_2$CH$_3$)-CO$_2$H) | 0.95(t, J=7Hz, 3H), 1.07(t, J=7Hz, 3H), 1.53~1.80(m, 2H), 2.20~2.50(m, 2H), 3.13~3.36(m, 2H), 3.90(s, 3H), 7.05~7.32(m, 2H), 7.53(m, 1H), 7.93(s, 1H), 9.10(s, 1H) | (DMSO-d$_6$) |

TABLE 3-continued

| 14 | 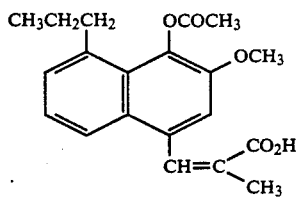 | 0.94(t, J=7Hz, 3H), 1.16(t, J=7Hz, 3H), 1.4~1.9(m, 2H), 2.3~2.6(m, 2H), 3.1~3.4(m, 2H), 3.82(s, 3H), 6.98(m, 1H), 7.0~7.25(m, 3H), 7.60(m, 1H), 8.85(s, 1H), 12.37(br.s, 1H) | (DMSO-$d_6$) |
|---|---|---|---|
| 15 | 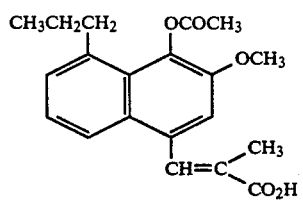 | 0.98(t, J=7Hz, 3H), 1.44~1.92(m, 2H), 3.04~3.32(m, 2H), 3.66(s, 3H), 3.76(s, 2H) 6.32(br.s, 1H), 7.00~7.36(m, 8H), 7.46(dd, J=3.6Hz, 7Hz, 1H), 7.82(br.s, 1H) | (CDCl$_3$) |

EXAMPLE 16

(Z)-3-(4-acetoxy-3-methoxy-5-propyl-1-naphthyl)-2-methylpropenoic acid

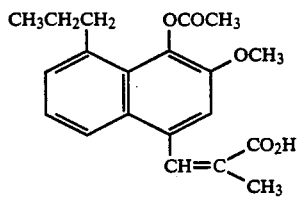

(a) Preparation of (E)-3-(4-acetoxy-3-methoxy-5-propyl-1-naphthyl)-2-methylpropenoic acid

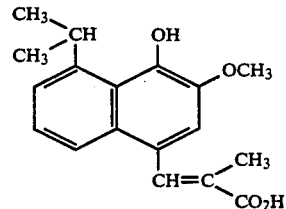

7.1 g of (E)-3-(4-hydroxy-3-methoxy-5-propyl-1-naphthyl)-2-methylpropenoic acid was dissolved in 20 ml of pyridine and 2 ml of acetic anhydride was added, followed by stirring at room temperature overnight. The reaction mixture was concentrated in vacuo and the resultant crystals were filtered and washed with ethyl acetate to obtain 7.5 g of the titled compound as colorless crystals.

Melting point: 207°–208° C.

$^1$H-NMR(90 MHz, CDCl$_3$-DMSO-$d_6$)δ: 1.04(t,J=7 Hz,3H), 1.60–1.90(m,2H), 1.97(d,J=2 Hz,3H), 2.43(s,3H), 2.91–3.16(m,2H), 3.93(s,3H), 7.12–7.38(m,3H), 7.72(m,1H), 8.11(m,1H).

(b) Preparation of (Z)-3-(4-acetoxy-3-methoxy-5-propyl-1-naphthyl)-2-methylpropenoic acid 7.4 g of (E)-3-(4-acetoxy-3-methoxy-5-propyl-1-naphthyl)-2-methylpropenoic acid was dissolved in 1.3 liters of acetone, and irradiated with light from a high pressure mercury lamp through a Pyrex filter at room temperature for 3 hours. The reaction mixture was concentrated in vacuo and purified by silica gel column chromatography (3% methanol/chloroform) to obtain 2.7 g of the titled compound as colorless crystals.

Melting point: 164°–165° C.

$^1$H-NMR(90 MHz, CDCl$_3$)δ: 1.01(t,J=7 Hz,3H), 1.44–1.92(m,2H), 2.16(d,J=1.8 Hz,3H), 2.38(s,3H), 2.80–3.12(m,2H), 3.79(s,3H), 6.37(br.s,1H), 7.01–7.32(m,4H), 7.44–7.70(m,1H).

EXAMPLE 17

(E)-3-(4-hydroxy-5-isopropyl-3-methoxy-1-naphthyl)-2-methylpropenoic acid

The 5-isopropyl-3-methoxy-4-methoxymethoxy-1-naphthalenecarbaldehyde obtained in Reference 12 and triethyl 2-phosphonopropionate were reacted in the same manner as in Example 1 to obtain the titled compound as yellow crystals.

Melting point: 198°–200° C.

$^1$H-NMR(90 MHz, CDCl$_3$)δ: 1.37(d,J=6.7 Hz,6H), 1.98(d,J=1.4 Hz,3H), 3.97(s,3H), 4.38–4.77(m,1H), 6.52(br.s,1H), 7.11(s,1H), 7.20–7.48(m,2H), 7.63(dd,J=2.0 Hz,7.8 Hz,1H), 8.11(s,1H).

EXAMPLE 18

(Z)-3-(4-hydroxy-5-isopropyl-3-methoxy-1-naphthyl)-2-methylpropenoic acid

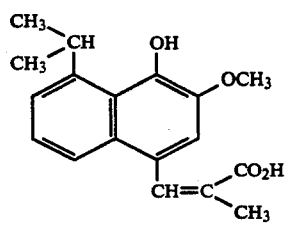

The ethyl (E)-3-(5-isopropyl-3-methoxy-4-methoxymethoxy-1-naphthyl)-2-methylpropenoate obtained in Example 17 were reacted in the same manner as in Example 2 to obtain the titled compound as yellow crystals.

Melting point: 195°–196° C.

$^1$H-NMR(90 MHz, CDCl$_3$)δ: 1.35(d,J=6.9 Hz,6H), 2.18(d,J=2.0 Hz,3H), 3.81(s,3H), 4.37–4.70(m,1H), 6.46(br.s,1H), 7.10–7.40(m,4H), 7.56(dd,J=2.0 Hz,7.7 Hz,1H).

EXAMPLE 19–25

The aldehydes obtained in References 14, 15, 13, 9, 12 and 5 and triethyl phosphonoacetate were, respectively, reacted in the same manner as in Example 1 to obtain compounds of Examples 19 to 25 indicated in Table 4.

TABLE 4

| Example No. | Structural Formula Name of Compound | Appearance | NMR Spectrum (90 MHz) | Melting Point (°C.) |
|---|---|---|---|---|
| 19 | (E)-3-(4-hydroxy-3-methyl-1-naphthyl)-propenoic acid | yellow crystals | | 194 to 196 |
| 20 | (E)-3-(3-chloro-5-ethyl-4-hydroxy-1-naphthyl)propenoic acid | yellow crystals | | over 200 (decomposed) |
| 21 | (E)-(4-hydroxy-3-methoxy-1-naphthyl)-propenoic acid | pale yellow crystals | | 178–180 |
| 23 | (E)-3-(4-hydroxy-3-methoxy-5-methyl-1-naphthyl)propenoic acid | yellow crystals | | 194–195 |
| 24 | (E)-3-(4-hydroxy-5-isopropyl-3-methoxy-1-naphthyl)propenoic acid | yellow crystals | | 188–189 |
| 25 | (E)-3-(3-ethoxy-5-ethyl-4-hydroxy-1-naphthyl)propenoic acid | yellow crystals | | 179–180 |

| No. | chemical formula | NMR data | (90 MHz) |
|---|---|---|---|
| 19 | | 2.40(s, 3H), 6.42(d, J=17.5Hz, 1H), 7.32~7.64(m, 2H), 7.76(s, 1H), 7.96~8.44(m, 3H) | (DMSO-d$_6$) |
| 20 | | 1.26(t, J=7Hz, 3H), 3.31(q, J=7Hz, 2H), 6.43(d, J=15Hz, 1H), 7.12~7.56(m, 2H), 7.68~8.00(m, 2H), 8.16(d, J=15Hz, 1H), 10.14(br.s, 1H), 12.42(br.s, 1H) | (DMSO-d$_6$) |
| 21 | | 3.98(s, 3H), 6.43(d, J=15.4Hz, 1H), 7.20~7.50(m, 2H), 7.64(s, 1H), 7.90~8.22(m, 2H), 8.42(d, J=15.4Hz, 1H) | (CD$_3$OD) |
| 22 | | 3.90(s, 3H), 4.14(s, 3H), 6.35(d, J=15.4Hz, 1H), 6.85–7.97(m, 4H), 8.26(d, J=15.4Hz, 1H) | (400MHz, DMSO-d$_6$) |

TABLE 4-continued

| | | |
|---|---|---|
| 23 | 2.86(s, 3H), 3.93(s, 3H), 6.48(d, J=16Hz, 1H), 7.02~7.30(m, 2H), 7.68~7.92(m, 2H), 8.23(d, J=16Hz, 1H), 9.30(s, 1H), 12.3(br.s, 1H) | (DMSO-$d_6$) |
| 24 | 1.36(d, J=6.7Hz, 6H), 4.00(s, 3H), 4.40~4.80(m, 1H), 6.32(d, J=15.4Hz, 1H), 7.21~7.43(m, 3H), 7.49(s, 1H), 7.91(dd, J=2.0Hz, 7.7Hz, 1H), 8.44(d, J=15.4Hz, 1H) | (CDCl$_3$) |
| 25 | 1.32(t, J=7Hz, 3H), 1.50(t, J=7Hz, 3H), 3.32(q, J=7Hz, 2H), 4.22(q, J=7Hz, 2H), 6.34(d, J=15.4Hz, 1H), 7.12~7.40(m, 2H), 7.48(s, 1H), 7.90(dd, J=2.6Hz, 7.7Hz, 1H), 8.50(d, J=15.4Hz, 1H) | (CDCl$_3$—CD$_3$OD) |

EXAMPLE 26

(E)-3-(5-ethyl-4-hydroxy-3-methoxy-1-naphthyl)-2-butenoic acid

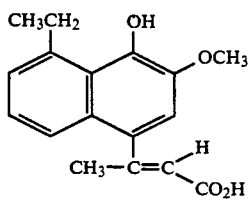

(a) Preparation of ethyl (E) and (Z)-3-(5-ethyl-3-methoxy-4-methoxymethoxy-1-naphthyl)-2-butenoate

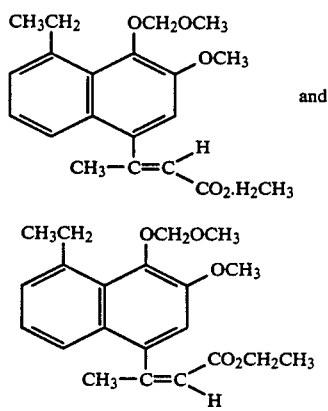

420 mg of 60% sodium hydride was suspended in 10 ml of N,N-dimethylformamide, to which 3.9 g of triethyl phosphonoacetate was added at room temperature. After stirring for 15 minutes, a solution of 1.0 g of 5'-ethyl-3'-methoxy-4'-methoxy-methoxy-1'-acetonaphthone in N,N-dimethylformamide (5 ml) was added. The reaction mixture was stirred at 90° C. for 3 hours. After cooling to room temperature, ice cooled water was added, followed by extraction with ethyl acetate. The organic layer was washed with water, dried with anhydrous magnesium sulfate and evaporated. The resultant residue was purified by silica gel column chromatography (5% ethyl acetate/hexane) to obtain 470 mg of the E isomer as colorless crystals and 290 mg of the Z isomer as a yellow oil.

(E product)
Melting point: 80°-81° C.
$^1$H-NMR(90 MHz, CDCl$_3$)δ: 1.30(t,J=7 Hz,6H), 2.59(d,J=1.8 Hz,3H), 3.36(q,J=7 Hz,2H), 3.56(s,3H), 3.93(s,3H), 4.21(q,J=7 Hz,2H), 5.15(s,2H), 5.94(d,J=1.8 Hz,1H), 7.04(s,1H), 7.08-7.28(m,2H), 7.44-7.68(m,1H).

(Z product)
$^1$H-NMR(90 MHz, CDCl$_3$)δ: 0.74(t,J=7 Hz,3H), 1.29(t,J=7 Hz,3H), 2.23(d,J=1.8 Hz,3H), 3.34(q,J=7 Hz,2H), 3.57(s,3H), 3.75(q,J=7 Hz,2H), 3.89(s,3H), 5.12(s,2H), 6.11(d,J=1.8 Hz,1H), 6.90(s,1H), 7.00-7.28(m,2H), 7.37-7.54(m,1H).

(b) (E)-3-(5-ethyl-3-methoxy-4-methoxymethoxy-1-naphthyl)-2-butenoic acid

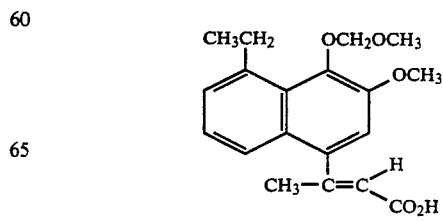

470 mg of ethyl (E)-3-(5-ethyl-3-methoxy-4-methoxymethoxy-1-naphthyl)-2-butenoate was dissolved in 5 ml of ethanol and 5 ml of tetrahydrofuran, to which 350 mg of potassium hydroxide and 2 ml of water were added, followed by refluxing for 1 hour. The reaction mixture was neutralized with 1N hydrochloric acid and extracted with ethyl acetate. The organic layer was washed with water, dried over anhydrous magnesium sulfate, and evaporated to obtain 280 mg of the titled compound as pale yellow crystals.

Melting point: 114°–115° C.

$^1$H-NMR(90 MHz, CDCl$_3$)δ: 1.31(t,J=7 Hz,3H), 2.62(br.s,3H), 3.37(q,J=7 Hz,2H), 3.59(s,3H), 3.96(s,3H), 5.17(s,2H), 6.00(m,1H), 7.05(s,1H), 7.16–7.36(m,2H), 7.48–7.72(m,1H).

(c) Preparation of (E)-3-(5-ethyl-4-hydroxy-3-methoxy-1-naphthyl)-2-butenoic acid

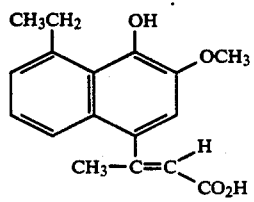

280 mg of (E)-3-(5-ethyl-3-methoxy-4-methoxymethoxy-1-naphthyl)-2-butenoic acid was dissolved in 8 ml of acetone, to which 1 ml of concentrated hydrochloric acid was added at room temperature. After stirring for 1 hour, 30 ml of water was added, followed by extraction with ethyl acetate. The organic layer was washed with water, dried over magnesium sulfate, and evaporated to obtain 177 mg of the titled compound as pale yellow crystals.

Melting point: 148°–150° C.

$^1$H-NMR(90 MHz, CDCl$_3$)δ: 1.34(t,J=7 Hz,3H), 2.61(br.s,3H), 3.34(q,J=7 Hz,2H), 3.98(s,3H), 6.00(br.s,1H), 6.40(br.s,1H), 6.98–7.34(m,3H), 7.42–7.70(m,1H).

EXAMPLE 27

(Z)-3-(5-ethyl-4-hydroxy-3-methoxy-1-naphthyl)-2-butenoic acid

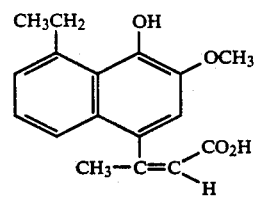

(a) Preparation of (Z)-3-(5-ethyl-3-methoxy-4-methoxymethoxy-1-naphthyl)-2-butenoic acid

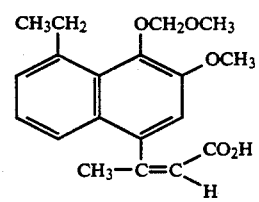

In the same manner as in Example 1(b), 180 mg of the title compound was obtained, as pale yellow crystals, from 290 mg of the ethyl (Z)-3-(5-ethyl-3-methoxy-4-methoxymethoxy-1-naphthyl)-2-butenoate.

Melting point: 116°–117° C.

$^1$H-NMR(90 MHz, CDCl$_3$)δ: 1.28(t,J=7 Hz,3H), 2.20(d,J=1.5 Hz,3H), 3.10–3.56(m,2H), 3.44(s,3H), 3.84(s,3H), 5.12(s,2H), 6.02(d,J=1.5 Hz,1H), 6.84(s,1H), 7.00–7.44(m,3H).

(b) Preparation of (Z)-3-(5-ethyl-4-hydroxy-3-methoxy-1-naphthyl)-2-butenoic acid

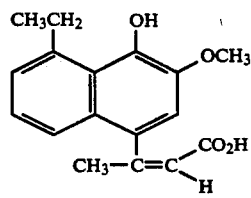

In the same manner as in Example 1(c), 125 mg of the titled compound was obtained, as pale yellow crystals, from 180 mg of (Z)-3-(5-ethyl-3-methoxy-4-methoxymethoxy-1-naphthyl)-2-butenoic acid.

Melting point: 185°–188° C.

$^1$H-NMR(90 MHz, CDCl$_3$-DMSO-d$_6$)δ: 1.33(t,J=7 Hz,3H), 2.21(d,J=1.8 Hz,3H), 3.31(q,J=7 Hz,2H), 3.93(s,3H), 6.13(m,1H), 6.44(br.s,1H), 6.93(s,1H), 7.04–7.57(m,3H).

EXAMPLE 28

(E)-3-(5-ethyl-4-hydroxy-3-methoxy-1-naphthyl)-2-heptenoic acid

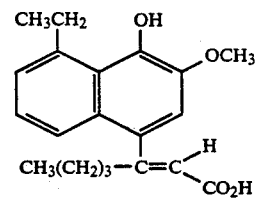

The 5'-ethyl-3'-methoxy-4'-methoxymethoxy-1'-valeronaphthone obtained in Reference 7 was reacted in the same manner as in Example 26 to obtain the titled compound as pale yellow crystals.

Melting point: 139°–140° C.

$^1$H-NMR(90 MHz, CDCl$_3$)δ: 0.68–0.96(m,3H), 1.12–1.56(m,6H), 2.88–3.20(m,2H), 3.32(q,J=7 Hz,2H), 3.96(s,3H), 5.88(s,1H), 6.36(br.s,1H), 6.96(s,1H), 7.04–7.30(m,2H), 7.40–7.64(m,1H).

EXAMPLE 29

(E)-3-(3-isopropyl-4-hydroxy-5-methyl-1-naphthyl)-propenoic acid

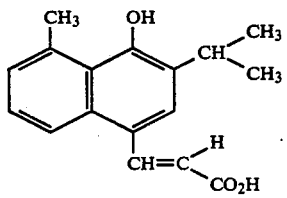

(a) Preparation of ethyl (E)-3-(4-acetoxy-3-isopropyl-5-methyl-1-naphthyl)propenoate

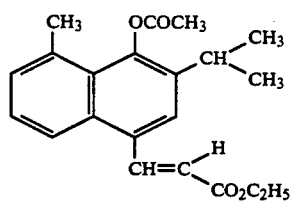

0.5 g of 4-acetoxy-3-isopropyl-5-methyl-1-naphthalenecarbaldehyde and 11 g of (carbethoxymethylene)triphenylphosphorane were dissolved in 50 ml of tetrahydrofuran and refluxed for 1 hour. The reaction mixture was cooled to room temperature and concetrated in vacuo. The resultant residue was purified by silica gel column chromatography (10% ethyl acetate/hexane) to obtain 0.5 g of the titled compound as pale yellow crystals.

Melting point: 122°-123° C.

$^1$H-NMR(90 MHz, CDCl$_3$)δ: 1.29(d,J=7 Hz,6H), 1.37(t,J=7 Hz,3H), 2.49(s,6H), 3.14(m,1H), 4.27(q,J=7 Hz,2H), 6.45(d,J=16 Hz,1H), 7.58(s,1H), 6.94–8.04(m,3H), 8.19(d,J=16 Hz,1H).

(b) (E)-3-(3-isopropyl-4-hydroxy-5-methyl-1-naphthyl)propenoic acid

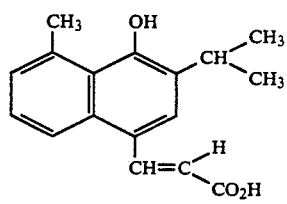

0.5 g of ethyl (E)-3-(4-acetoxy-3-isopropyl-5-methyl-1-naphthyl)propenoate was dissolved in 50 ml of ethanol, to which a potassium hydroxide aqueous solution (potassium hydroxide 1.6 g/water 10 ml) was added, followed by refluxing for 30 minutes. The solution was cooled to 0° C. and water was added. Dilute hydrochloric acid was added to make the aqueous phase acidic and extracted with ethyl acetate. The organic phase was washed with brine, dried with anhydrous magnesium sulfate, and concentrated in vacuo. The residue was purified by silica gel column chromatography (40% ethyl acetate/hexane) and the resultant crystals were recrystallized from a mixed solvent of isopropyl ether and ethyl acetate (1:1) and washed with isopropyl ether and hexane (3:7) to obtain 0.19 g of the titled compound as yellow needle.

Melting point: 171°-174° C.

$^1$H-NMR(90 MHz, DMSO-d$_6$)δ: 1.27(d,J=7 Hz,6H), 2.50(s,3H), 3.55(m,1H), 6.49(d,J=16 Hz,1H), 7.23–7.51(m,1H), 7.77(s,1H), 7.87–8.15(m,2H), 8.31(d,J=16 Hz, 1H), 9.50(br.s,1H).

EXAMPLE 30

Ethyl (E)-3-(5-ethyl-4-hydroxy-3-methoxy-1-naphthyl)-propenoate

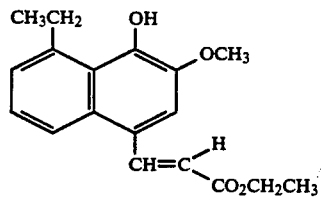

To a solution of 1.3 g of ethyl (E)-3-(5-ethyl-3-methoxy-4-methoxymethoxy-1-naphthyl)propenoate in ethanol (10 ml) was added 1 ml of concentrated hydrochloric acid and stirred at room temperature for 2 hours. Water was added to the reaction mixture and extracted with ethyl acetate. The organic layer was washed with water and brine and dried over anhydrous magnesium sulfate. After evaporation, hexane was added for crystallization to obtain 0.76 g of the titled compound as pale yellow crystals.

Melting point: 75°-76° C.

$^1$H-NMR(90 MHz, CDCl$_3$): 1.31(t,J=7 Hz,3H), 1.37(t,J=7 Hz,3H), 3.33(q,J=7 Hz,2H), 4.00(s,3H), 4.27(q,J=7 Hz,2H), 6.35(d,J=15 Hz,1H), 6.60(s,1H), 7.09–7.36(m,2H), 7.47(s,1H), 7.91(dd,J=2 Hz, 8 Hz,1H), 8.44(d,J=15 Hz,1H).

EXAMPLE 31

Ethyl (E)-3-(4-hydroxy-3-methyl-1-naphthyl)-propenoate

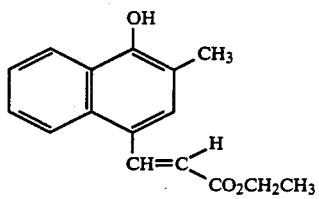

In the same manner as in Example 30, the titled compound was obtained, as reddish orange crystals, from ethyl (E)-3-(4-methoxymethoxy-3-methyl-1-naphthyl)-propenoate.

Melting point: 122°-124° C.

$^1$H-NMR(90 MHz, CDCl$_3$): 1.36(t,J=7 Hz,3H), 2.43(s,3H), 4.27(q,J=7 Hz,2H), 6.41(d,J=15 Hz,1H), 7.19–7.67(m,2H), 7.60(s,1H), 7.87–8.39(m,2H), 8.44(d,J=15 Hz,1H).

EXAMPLE 32

(E)-1-[3-(5-ethyl-4-hydroxy-3-methoxy-1-naphthyl)-1-oxo-2-propenyl]piperidine

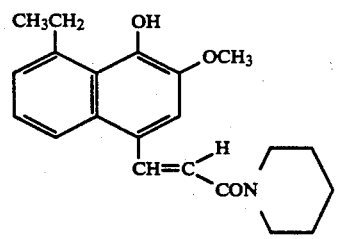

(a) (E)-1-[3-(5-ethyl-3-methoxy-4-methoxymethoxy-1-naphthyl)-1-oxo-2-propenyl]piperidine

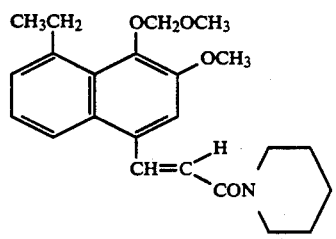

0.15 g of 60% sodium hydride was suspended in 20 ml of N,N-dimethylformamide, to which 1.15 g of N-(diethoxyphosphoryl)acetylpiperidine was gradually added at room temperature. After stirring for 10 minutes, a solution of 800 mg of 5-ethyl-3-methoxy-4-methoxymethoxy-1-naphthalenecarbaldehyde in N,N-dimethylformamide (10 ml) was gradually added. After stirring for 20 minutes, water was added, followed by extraction with ethyl acetate. The combined extracts were washed with water and dried over anhydrous magnesium sulfate. After removal of the solvent, the resultant residue was purified by silica gel column chromatography (30% ethyl acetate/hexane) to obtain 1.1 g of the titled compound as pale yellow crystals.

Melting point: 85°–86° C.

$^1$H-NMR(90 MHz, CDCl$_3$): 1.28(t,J=7 Hz,3H), 1.44–1.80(m,6H), 3.34(q,J=7 Hz,2H), 3.56(s,3H), 3.44–3.80(m,4H), 3.98(s,3H), 5.16(s,2H), 6.76(d,J=15.4 Hz,1H), 7.16–7.32(m,2H), 7.38(s,1H), 7.80–8.00(m,1H), 8.32(d,J=15.4 Hz,1H).

(b) (E)-1-[3-(5-ethyl-4-hydroxy-3-methoxy-1-naphthyl)-1-oxo-2-propenyl]piperidine

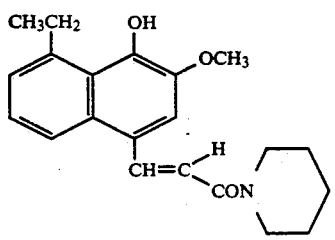

960 mg of (E)-1-[3-(5-ethyl-3-methoxy-4-methoxymethoxy-1-naphthyl)-1-oxo-2-propenyl]piperidine was dissolved in 50 ml of acetone, to which 1 ml of concentrated hydrochloric acid was gradually added at room temperature. After stirring at room temperature for 5 hours, the reaction mixture was slowly poured into water. The resultant crystals were collected by filtration, washed with water and dried to obtain 760 mg of the titled compound as yellow crystals.

Melting point: 176°–179° C.

$^1$H-NMR(90 MHz, CDCl$_3$): 1.30(t,J=7 Hz,3H), 1.42–1.80(m,6H), 3.32 (q,J=7 Hz,2H), 3.44–3.78(m,4H), 4.00(s,3H), 6.52(s,1H), 6.72(d,J=15.4 Hz,1H), 7.08–7.28(m,2H), 7.36(s,1H), 7.88(dd,J=2.6 Hz,7.7 Hz,1H), 8.32(d,J=15.4 Hz,1H).

EXAMPLE 33 and 34

5-ethyl-3-methoxy-4-methoxymethoxy-1naphthalene-carbaldehyde was reacted with a suitable Wittig agent. The product was treated in the same way as shown in Example 1.

EXAMPLE 36 to 41

The aldehyde obtained in Reference Examples 23, 24, 22, 12, 16 and 5 and ethyl diethylphosphonoacetate were treated in the same way as shown in Example 1.

Table 5 shows the results of Examples 33, 34 and 36 to 41.

EXAMPLE 35

(E)-2-cyclopentyl-3-(4-hydroxy-3-methoxy-5-methyl-1-naphthyl)propenic acid

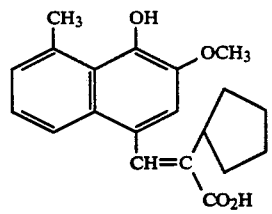

When 3-methoxy-4-methoxymethoxy-5-methyl-1-naphthalene carbaldehyde obtained in Reference Example 9 and triethyl 2-phosphono cyclopentyl acetate were processed in the same procedures as those in Example 1, the above-captioned compound was obtained as yellow crystals.

m.p. ;173°~175° C.

$^1$H-NMR(90 MHz, DMSO-d$_6$)δ; 1.3~2.1(m,8H), 2.7~3.1(m,1H), 2.85 (s, 3H), 3.86(s,3H), 6.98~7.58(m,4H), 7.83(s,1H), 8.99(s,1H), 12.41(br.s,1H)

TABLE 5

| No. | chemical formula | appearance | NMR data | (90 MHz) | m.p.(°C.) |
|---|---|---|---|---|---|
| 33 | CH₃CH₂ at 8-position, OH, OCH₃ at 2-position, CH=C(CH₂CH₂OCH₃)(CO₂H) at 4-position on naphthalene | light yellow crystals | 1.32(t, J=7Hz, 3H), 2.74(t, J=7Hz, 2H), 3.32(s, 3H), 3.33(q, J=7Hz, 2H), 3.62(t, J=7Hz, 2H), 3.98(s, 3H), 6.45(s, 1H), 7.10~7.54(m, 1H), 7.54~7.70(m, 1H), 7.72(s, 1H), 8.38(s, 1H) | (CDCl₃) | 157~158 |
| 34 | CH₃CH₂ at 8-position, OH, OCH₃ at 2-position, CH=C(CH₂-thienyl)(CO₂H) at 4-position on naphthalene | light yellow crystals | 1.24(t, J=7Hz, 3H), 3.10~3.44(m, 2H) 3.66(s, 3H), 3.85(s, 2H), 6.68~7.65(m, 7H), 8.14(s, 1H), 9.17(s, 1H), 12.67(br.s, 1H) | (DMSO-d₆) | 160~163 |
| 36 | CH₃OCH₂CH₂CH₂ at 8-position, OH, OCH₃ at 2-position, CH=CHCO₂H at 4-position on naphthalene | yellow crystals | 1.72~2.02(m, 2H), 3.15~3.44(m, 4H), 3.21(s, 3H), 3.94(s, 3H), 6.50(d, J=16Hz, 1H), 7.04~7.36(m, 2H), 7.69~7.96(m, 2H), 8.27(d, J=16Hz, 1H), 9.43(s, 1H), 12.28(br.s, 1H) | (DMSO-d₆) | 186~188 decomposition |
| 38 | OH, OCH₃ at 2-position, CH₃CH₂ at 5-position, CH=CHCO₂H at 4-position on naphthalene | light yellow crystals | 1.36(t, J=7Hz, 3H), 3.11(q, J=7Hz, 2H), 3.99(s, 3H), 6.16(d, J=16Hz, 1H), 7.14~7.46(m, 3H), 8.05(dd, J=3Hz, 7Hz, 1H), 8.64(d, J=16Hz, 1H) | (CDCl₃) | 168~169 |
| 37 | OH, OCH₃ at 2-position, CH₃CH₂ at 6-position, CH=CHCO₂H at 4-position on naphthalene | yellow crystals | 1.30(t, J=7Hz, 3H), 2.77(q, J=7Hz, 2H), 3.98(s, 3H), 6.37(d, J=16Hz, 1H), 7.18~7.38(m, 1H), 7.50(s, 1H), 7.82(br.s, 1H), 8.06(d, J=7Hz, 1H), 8.44(d, J=16Hz, 1H) | (CDCl₃-DMSO-d₆) | 161~162 |
| 39 | CH₃CH₂ at 8-position, OH, OCH₂CH₂OCH₃ at 2-position, CH=C(H)(CO₂H) at 4-position on naphthalene | yellow crystals | 1.32(t, J=7Hz, 3H), 3.34(q, J=7Hz, 2H), 3.48(s, 3H), 3.56~3.82(m, 2H), 4.10~4.36(m, 2H), 6.36(d, J=15Hz, 1H), 7.14~7.50(m, 2H), 7.56(s, 1H), 7.94(d, J=7Hz, 1H), 8.52(d, J=15Hz, 1H) | (CDCl₃) | 142~143 |
| 40 | CH₃CH₂ at 8-position, OH, OCH₂CH₂CH₂CH₂CH₃ at 2-position, CH=C(H)(CO₂H) at 4-position on naphthalene | yellow crystals | 0.80~1.10(m, 3H), 1.16~1.62(m, 7H), 1.62~2.04(m, 2H), 3.32(q, J=7Hz, 2H), 4.16(t, J=7Hz, 2H), 6.36(d, J=15Hz, 2H), 6.62(br.s, 1H), 7.12~7.42(m, 2H), 7.50(s, 1H), 7.92(dd, J=2.6Hz, 7Hz, 1H), 8.56(d, J=15Hz, 1H) | (CDCl₃) | 137~138 |

TABLE 5-continued

| No. | chemical formula | appearance | NMR data | (90 MHz) | m.p.(°C) |
|---|---|---|---|---|---|
| 41 | 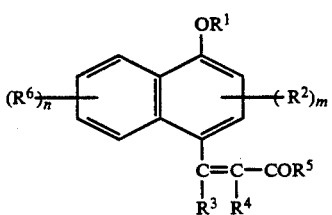 | yellow crystals | 1.30(t, J=7Hz, 3H), 3.30(q, J=7Hz, 2H), 5.20(s, 2H), 6.30(d, J=15Hz, 1H), 7.10~7.70(m, 8H), 7.90(dd, J=2.6Hz, 7Hz, 1H), 8.50(d, J=15Hz, 1H) | (CDCl$_3$) | 172~174 |

We claim:

1. A naphthalene derivative having the formula and a pharmacologically acceptable salt thereof:

wherein R$^1$ represents a hydrogen atom, a lower alkyl group or an acyl group;

R$^2$ independently represents a hydrogen atom, a lower alkyl group, a lower alkoxy group, a halogen atom, a cycloalkyl group, a cycloalkylalkyl group, a hydroxyl group, an aryl group which may be substituted, an arylalkyl group whose aryl group may be substituted, a heteroaryl group, or a heteroarylalkyl group;

R$^3$ and R$^4$ are the same or different and represent a lower alkyl group, a lower alkenyl group, an aryl group which may have a substituent, an arylalkyl group whose aryl group may be substituted, an arylalkenyl group whose aryl group may be substituted, a cycloalkyl group, an alkoxyalkyl group, a heteroaryl group, a heteroarylalkyl group, a carboxyl group or R$^3$ is a hydrogen atom, a carboxyalkyl group, an aminoalkyl group, or a cyano group; provided R$^3$ is other than hydrogen when R$^4$ is lower alkyl;

R$^5$ represents a group of the formula, —OR$^7$, (wherein R$^7$ represents a hydrogen atom or a lower alkyl group), or a group of the formula, $$-N-R^8,$$
$$\phantom{-N-}R^9$$

(wherein R$^8$ and R$^9$ are the same or different and represent a hydrogen atom or a lower alkyl group, or R$^8$ and R$^9$ can form, along with the nitrogen atom bonded with R$^8$ and R$^9$, a ring which may contain an oxygen atom);

R$^6$ independently represents a hydrogen atom, a halogen atom, a lower alkyl group, a lower alkoxy group, a hydroxyl group, an amino group, an arylalkyl group, or an aryl group; and m is 0 or an integer of from 1 to 2, and n is 0 or an integer of from 1 to 4.

2. The naphthalene derivative and the salt as claimed in claim 1, in which n is 1 and R6 is a lower alkyl attached to the 5-position of the naphthalne ring.

3. The naphthalene derivative and the salt as claimed in claim 1, in which m is 1 and R2 is a lower alkoxy attached to the 3-position of the naphthalene ring.

4. The naphthalene derivative and the salt as claimed in claim 1, in which n is 1, R6 is a lower alkyl attached to the 5-position of the naphthalene ring, m is 1 and R2 is a lower alkoxy attached to the 3-position of the naphthalene ring.

5. The naphthalene derivative and the salt as claimed in claim 1, in which R3 is hydrogen and R4 is a lower alkyl.

6. The naphthalene derivative and the salt as claimed in claim 1, in which n is 1, R6 is a lower alkyl attached to the 5-position of the naphthalene ring, m is 1 and R2 is a lower alkoxy attached to the 3-position of the naphthalene ring, R3 is hydrogen and R4 is a lower alkyl.

7. The naphthalene derivative and the salt as claimed in claim 1, in which n is 1, R6 is ethyl attached to the 5-position of the naphthalene ring.

8. The naphthalene derivative and the salt as claimed in claim 1, in which n is 1, R6 is ethyl attached to the 5-position of the naphthalene ring, m is 1 and R2 is methoxy attached to the 3-position of the naphthalene ring.

9. The naphthalene derivative and the salt as claimed in claim 1, in which n is 1, R6 is ethyl attached to the 5-position of the naphthalene ring, m is 1 and R2 is methoxy attached to the 3-position of the naphthalene ring, R3 is hydrogen and R4 is a lower alkyl.

10. The naphthalene derivative and the salt as claimed in claim 1, in which R1 is hydrogen, a lower alkyl or an acyl.

11. The naphthalene derivative and the salt as claimed in claim 1, in which R1 is an acyl.

12. The naphthalene derivative and the salt as claimed in claim 1, in which n is 1, R6 is a lower alkyl attached to the 5-position of the naphthalene ring, m is 1, R2 is a lower alkoxy attached to the 3-position of the naphthalene ring, R3 is hydrogen, R4 is a lower alkyl and R1 is hydrogen.

13. The naphthalene derivative and the salt as claimed in claim 1, in which n is 1, R6 is a lower alkyl attached to the 5-position of the naphthalene ring, m is 1, R2 is a lower alkoxy attached to the 3-position of the naphthalene ring, R3 is hydrogen, R4 is a lower alkyl and R1 is an acyl.

14. The naphthalene derivative and the salt as claimed in claim 1, in which n is 1, R6 is a lower alkyl attached to the 5-position of the naphthalene ring, m is 1, R2 is a lower alkoxy attached to the naphthalene ring, R3 is hydrogen, R4 is a lower alkyl and R1 is acetyl.

15. The naphthalene derivative and the salt as claimed in claim 1, in which the naphthalene ring has one or more lower alkyl at the 5-, 7- and 8-positions.

16. A pharmaceutical composition which comprises a therapeutically effective amount of the naphthalene derivative defined in claim 1 or a pharmacologically acceptable salt thereof and a pharmacologically acceptable carrier.

17. The composition as claimed in claim 16, which is to treat a disease for which an inhibitory action on the production of IL-1 is effective.

18. A method for treating a desease for which an inhibitory action on the production of IL-1 is effective, which comprises administering to a human being suffering from the disease a therapeutically effective amount of the naphthalene derivative defined in claim 1 or a pharmacologically acceptable salt thereof.

19. The method as claimed in claim 18, in which the disease is an autoimmune disease.

20. The method as claimed in claim 18, in which the disease is chronic articular rheumatism, systematic lupus erythromatodes, systematic scleroderm, Bechet's disease, periarteritis nodosa, ulcerative colitis, chronic active hepatitis or glomerulonephritis.

21. The method as claimed in claim 18, in which the disease is an intractable disease based on the morbid states of inflammatory symptoms.

22. The method as claimed in claim 18, in which the disease is arthritis deformans, gout, atherosclerosis, psoriasis, atopic dermatitis, lung diseses accompanied by granuloma or an encephalites.

* * * * *